(12) United States Patent
Shelton, IV et al.

(10) Patent No.: US 9,974,529 B2
(45) Date of Patent: May 22, 2018

(54) SURGICAL INSTRUMENT

(71) Applicant: Ethicon Endo-Surgery, Inc., Cincinnati, OH (US)

(72) Inventors: Frederick E. Shelton, IV, Hillsboro, OH (US); Chester O. Baxter, III, Loveland, OH (US); Steven G. Hall, Cincinnati, OH (US); Andrew Yoo, Princeton Junction, NJ (US); Edward G. Chekan, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 229 days.

(21) Appl. No.: 14/703,109

(22) Filed: May 4, 2015

(65) Prior Publication Data
US 2015/0230783 A1 Aug. 20, 2015

Related U.S. Application Data

(63) Continuation of application No. 13/181,798, filed on Jul. 13, 2011, now Pat. No. 9,113,884.

(60) Provisional application No. 61/452,432, filed on Mar. 14, 2011.

(51) Int. Cl.
*A61B 17/00* (2006.01)

(52) U.S. Cl.
CPC ............ *A61B 17/00234* (2013.01); *A61B 2017/00353* (2013.01); *A61B 2560/0443* (2013.01)

(58) Field of Classification Search
CPC .......................... A61B 17/1155; A61B 17/105
USPC ............... 227/19, 176.1, 179.1, 180.1, 181.1
See application file for complete search history.

(56) References Cited

U.S. PATENT DOCUMENTS

| 2,224,882 A | 12/1940 | Peck |
| 2,742,955 A | 4/1956 | Dominguez |
| 3,166,072 A | 1/1965 | Sullivan, Jr. |
| 3,266,494 A | 8/1966 | Brownrigg et al. |
| 3,551,987 A | 1/1971 | Wilkinson |
| 3,744,495 A | 7/1973 | Johnson |
| 3,746,002 A | 7/1973 | Haller |
| 3,863,639 A | 2/1975 | Kleaveland |
| 4,190,042 A | 2/1980 | Sinnreich |
| 4,198,982 A | 4/1980 | Fortner et al. |

(Continued)

FOREIGN PATENT DOCUMENTS

| AU | 2008207624 A1 | 3/2009 |
| AU | 2010214687 A1 | 9/2010 |

(Continued)

OTHER PUBLICATIONS

International Preliminary Report on Patentability for PCT/US2012/028886, dated Sep. 17, 2013 (14 pages).

(Continued)

*Primary Examiner* — Nathaniel Chukwurah

(57) ABSTRACT

A surgical instrument is disclosed. The surgical instrument includes an actuation system, a drive system, and a tool head. The drive system is coupled to the actuation system and includes a rotatable shaft which defines a longitudinal axis. The tool head is coupled to the drive system and includes an annular cartridge and a pliable bunchable ring. The annular cartridge includes a plurality of staples. The pliable bunchable ring surrounds the annular cartridge. The surgical instrument is configured to drive the staples through the pliable bunchable ring substantially transverse to the longitudinal axis.

18 Claims, 51 Drawing Sheets

(56) References Cited

U.S. PATENT DOCUMENTS

| | | |
|---|---|---|
| 4,207,898 A | 6/1980 | Becht |
| 4,274,398 A | 6/1981 | Scott, Jr. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,573,468 A | 3/1986 | Conta et al. |
| 4,605,004 A | 8/1986 | Di Giovanni et al. |
| 4,654,028 A | 3/1987 | Suma |
| 4,655,222 A | 4/1987 | Florez et al. |
| 4,700,703 A | 10/1987 | Resnick et al. |
| 4,744,363 A | 5/1988 | Hasson |
| 4,773,420 A | 9/1988 | Green |
| 4,809,695 A | 3/1989 | Gwathmey et al. |
| 4,844,068 A | 7/1989 | Arata et al. |
| 4,873,977 A | 10/1989 | Avant et al. |
| 4,893,622 A | 1/1990 | Green et al. |
| 4,903,697 A | 2/1990 | Resnick et al. |
| 4,909,789 A | 3/1990 | Taguchi et al. |
| 4,930,674 A | 6/1990 | Barak |
| 4,984,564 A | 1/1991 | Yuen |
| 5,002,553 A | 3/1991 | Shiber |
| 5,027,834 A | 7/1991 | Pruitt |
| 5,071,430 A | 12/1991 | de Salis et al. |
| 5,074,454 A | 12/1991 | Peters |
| 5,084,057 A | 1/1992 | Green et al. |
| 5,104,025 A | 4/1992 | Main et al. |
| 5,104,397 A | 4/1992 | Vasconcelos et al. |
| 5,108,368 A | 4/1992 | Hammerslag et al. |
| 5,116,349 A | 5/1992 | Aranyi |
| 5,122,156 A | 6/1992 | Granger et al. |
| 5,139,513 A | 8/1992 | Segato |
| 5,141,144 A | 8/1992 | Foslien et al. |
| 5,156,609 A | 10/1992 | Nakao et al. |
| 5,158,567 A | 10/1992 | Green |
| 5,171,247 A | 12/1992 | Hughett et al. |
| 5,171,249 A | 12/1992 | Stefanchik et al. |
| 5,195,505 A | 3/1993 | Josefsen |
| 5,197,649 A | 3/1993 | Bessler et al. |
| 5,205,459 A | 4/1993 | Brinkerhoff et al. |
| 5,211,655 A | 5/1993 | Hasson |
| 5,222,963 A | 6/1993 | Brinkerhoff et al. |
| 5,222,975 A | 6/1993 | Crainich |
| 5,234,447 A | 8/1993 | Kaster et al. |
| 5,236,440 A | 8/1993 | Hlavacek |
| 5,258,009 A | 11/1993 | Conners |
| 5,282,829 A | 2/1994 | Hermes |
| 5,285,945 A | 2/1994 | Brinkerhoff et al. |
| 5,304,204 A | 4/1994 | Bregen |
| 5,309,927 A | 5/1994 | Welch |
| 5,312,023 A | 5/1994 | Green et al. |
| 5,314,445 A | 5/1994 | Heidmueller née Degwitz et al. |
| 5,330,502 A | 7/1994 | Hassler et al. |
| 5,333,772 A | 8/1994 | Rothfuss et al. |
| 5,336,232 A | 8/1994 | Green et al. |
| 5,342,385 A | 8/1994 | Norelli et al. |
| 5,342,395 A | 8/1994 | Jarrett et al. |
| 5,342,396 A | 8/1994 | Cook |
| 5,346,115 A * | 9/1994 | Perouse ............. A61B 17/1152 227/179.1 |
| 5,350,400 A | 9/1994 | Esposito et al. |
| 5,354,250 A | 10/1994 | Christensen |
| 5,354,303 A | 10/1994 | Spaeth et al. |
| 5,358,506 A | 10/1994 | Green et al. |
| 5,366,479 A | 11/1994 | McGarry et al. |
| 5,374,277 A | 12/1994 | Hassler |
| 5,375,588 A | 12/1994 | Yoon |
| 5,383,880 A | 1/1995 | Hooven |
| 5,383,888 A | 1/1995 | Zvenyatsky et al. |
| 5,383,895 A | 1/1995 | Holmes et al. |
| 5,391,180 A | 2/1995 | Tovey et al. |
| 5,395,030 A | 3/1995 | Kuramoto et al. |
| 5,395,384 A | 3/1995 | Duthoit |
| 5,404,870 A | 4/1995 | Brinkerhoff et al. |
| 5,405,072 A | 4/1995 | Zlock et al. |
| 5,405,344 A | 4/1995 | Williamson et al. |
| 5,405,360 A | 4/1995 | Tovey |
| 5,411,508 A | 5/1995 | Bessler et al. |
| 5,413,272 A | 5/1995 | Green et al. |
| 5,413,573 A | 5/1995 | Koivukangas |
| 5,415,334 A | 5/1995 | Williamson, IV et al. |
| 5,417,361 A | 5/1995 | Williamson, IV |
| 5,425,745 A | 6/1995 | Green et al. |
| 5,441,494 A | 8/1995 | Ortiz |
| 5,445,644 A | 8/1995 | Pietrafitta et al. |
| 5,449,365 A | 9/1995 | Green et al. |
| 5,452,837 A | 9/1995 | Williamson, IV et al. |
| 5,474,057 A | 12/1995 | Makower et al. |
| 5,476,479 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,490,819 A | 2/1996 | Nicholas et al. |
| 5,497,933 A | 3/1996 | DeFonzo et al. |
| 5,503,320 A | 4/1996 | Webster et al. |
| 5,503,635 A | 4/1996 | Sauer et al. |
| 5,505,363 A | 4/1996 | Green et al. |
| 5,507,426 A | 4/1996 | Young et al. |
| 5,509,596 A | 4/1996 | Green et al. |
| 5,511,564 A | 4/1996 | Wilk |
| 5,514,157 A | 5/1996 | Nicholas et al. |
| 5,520,609 A | 5/1996 | Moll et al. |
| 5,520,678 A | 5/1996 | Heckele et al. |
| 5,527,264 A | 6/1996 | Moll et al. |
| 5,529,235 A | 6/1996 | Boiarski et al. |
| 5,531,856 A | 7/1996 | Moll et al. |
| 5,533,661 A | 7/1996 | Main et al. |
| 5,535,934 A | 7/1996 | Boiarski et al. |
| 5,540,375 A | 7/1996 | Bolanos et al. |
| 5,542,594 A | 8/1996 | McKean et al. |
| 5,549,621 A | 8/1996 | Bessler et al. |
| 5,549,637 A | 8/1996 | Crainich |
| 5,551,622 A | 9/1996 | Yoon |
| 5,553,765 A | 9/1996 | Knodel et al. |
| 5,554,169 A | 9/1996 | Green et al. |
| 5,556,416 A | 9/1996 | Clark et al. |
| 5,558,665 A | 9/1996 | Kieturakis |
| 5,560,530 A | 10/1996 | Bolanos et al. |
| 5,560,532 A | 10/1996 | DeFonzo et al. |
| 5,562,241 A | 10/1996 | Knodel et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,571,285 A | 11/1996 | Chow et al. |
| 5,575,803 A | 11/1996 | Cooper et al. |
| 5,575,805 A | 11/1996 | Li |
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,607,450 A | 3/1997 | Zvenyatsky et al. |
| 5,609,285 A | 3/1997 | Grant et al. |
| 5,613,937 A | 3/1997 | Garrison et al. |
| 5,615,820 A | 4/1997 | Viola |
| 5,618,303 A | 4/1997 | Marlow et al. |
| 5,618,307 A | 4/1997 | Donlon et al. |
| 5,620,452 A | 4/1997 | Yoon |
| 5,628,446 A | 5/1997 | Geiste et al. |
| 5,628,743 A | 5/1997 | Cimino |

(56) References Cited

U.S. PATENT DOCUMENTS

| | | |
|---|---|---|
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,651,491 A | 7/1997 | Heaton et al. |
| 5,651,762 A | 7/1997 | Bridges |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,681,341 A | 10/1997 | Lunsford et al. |
| 5,683,349 A | 11/1997 | Makower et al. |
| 5,685,474 A | 11/1997 | Seeber |
| 5,685,826 A | 11/1997 | Bonutti |
| 5,690,269 A | 11/1997 | Bolanos et al. |
| 5,692,668 A | 12/1997 | Schulze et al. |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,409 A | 12/1997 | Rayburn et al. |
| 5,704,534 A | 1/1998 | Huitema et al. |
| 5,707,392 A | 1/1998 | Kortenbach |
| 5,709,706 A | 1/1998 | Kienzle et al. |
| 5,711,472 A | 1/1998 | Bryan |
| 5,713,505 A | 2/1998 | Huitema |
| 5,715,987 A | 2/1998 | Kelley et al. |
| 5,718,360 A | 2/1998 | Green et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,874 A | 4/1998 | Measamer et al. |
| 5,738,629 A | 4/1998 | Moll et al. |
| 5,741,271 A | 4/1998 | Nakao et al. |
| 5,743,456 A | 4/1998 | Jones et al. |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,752,970 A | 5/1998 | Yoon |
| 5,758,814 A | 6/1998 | Gallagher et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,779,130 A | 7/1998 | Alesi et al. |
| 5,779,131 A | 7/1998 | Knodel et al. |
| 5,779,132 A | 7/1998 | Knodel et al. |
| 5,782,397 A | 7/1998 | Koukline |
| 5,782,859 A | 7/1998 | Nicholas et al. |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,797,536 A | 8/1998 | Smith et al. |
| 5,797,537 A | 8/1998 | Oberlin et al. |
| 5,797,538 A | 8/1998 | Heaton et al. |
| 5,797,959 A | 8/1998 | Castro et al. |
| 5,799,857 A | 9/1998 | Robertson et al. |
| 5,807,376 A | 9/1998 | Viola et al. |
| 5,807,378 A | 9/1998 | Jensen et al. |
| 5,810,721 A | 9/1998 | Mueller et al. |
| 5,810,855 A | 9/1998 | Rayburn et al. |
| 5,814,055 A | 9/1998 | Knodel et al. |
| 5,814,057 A | 9/1998 | Oi et al. |
| 5,817,084 A | 10/1998 | Jensen |
| 5,820,009 A | 10/1998 | Melling et al. |
| 5,826,776 A | 10/1998 | Schulze et al. |
| 5,836,503 A | 11/1998 | Ehrenfels et al. |
| 5,839,369 A | 11/1998 | Chatterjee et al. |
| 5,839,639 A | 11/1998 | Sauer et al. |
| 5,843,096 A | 12/1998 | Igaki et al. |
| 5,855,311 A | 1/1999 | Hamblin et al. |
| 5,860,581 A | 1/1999 | Robertson et al. |
| 5,865,361 A | 2/1999 | Milliman et al. |
| 5,871,135 A | 2/1999 | Williamson, IV et al. |
| 5,901,895 A | 5/1999 | Heaton et al. |
| 5,906,577 A | 5/1999 | Beane et al. |
| 5,906,625 A | 5/1999 | Bito et al. |
| 5,911,353 A | 6/1999 | Bolanos et al. |
| 5,915,616 A | 6/1999 | Viola et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,947,984 A | 9/1999 | Whipple |
| 5,951,576 A | 9/1999 | Wakabayashi |
| 5,954,259 A | 9/1999 | Viola et al. |
| 5,964,774 A | 10/1999 | McKean et al. |
| 5,997,528 A | 12/1999 | Bisch et al. |
| 6,003,517 A | 12/1999 | Sheffield et al. |
| 6,010,054 A | 1/2000 | Johnson et al. |
| 6,017,356 A | 1/2000 | Frederick et al. |
| 6,024,748 A | 2/2000 | Manzo et al. |
| 6,032,849 A | 3/2000 | Mastri et al. |
| 6,053,390 A | 4/2000 | Green et al. |
| RE36,720 E | 5/2000 | Green et al. |
| 6,056,735 A | 5/2000 | Okada et al. |
| 6,063,025 A | 5/2000 | Bridges et al. |
| 6,063,097 A | 5/2000 | Oi et al. |
| 6,083,234 A | 7/2000 | Nicholas et al. |
| 6,083,242 A | 7/2000 | Cook |
| 6,099,551 A | 8/2000 | Gabbay |
| 6,102,271 A | 8/2000 | Longo et al. |
| 6,117,158 A | 9/2000 | Measamer et al. |
| 6,119,913 A | 9/2000 | Adams et al. |
| 6,126,058 A | 10/2000 | Adams et al. |
| 6,142,933 A | 11/2000 | Longo et al. |
| 6,159,146 A | 12/2000 | El Gazayerli |
| 6,159,200 A | 12/2000 | Verdura et al. |
| 6,162,208 A | 12/2000 | Hipps |
| 6,165,188 A | 12/2000 | Saadat et al. |
| 6,171,330 B1 | 1/2001 | Benchetrit |
| 6,174,318 B1 | 1/2001 | Bates et al. |
| 6,193,129 B1 | 2/2001 | Bittner et al. |
| 6,202,914 B1 | 3/2001 | Geiste et al. |
| 6,214,028 B1 | 4/2001 | Yoon et al. |
| 6,221,007 B1 | 4/2001 | Green |
| 6,231,565 B1 | 5/2001 | Tovey et al. |
| 6,234,178 B1 | 5/2001 | Goble et al. |
| 6,241,139 B1 | 6/2001 | Milliman et al. |
| 6,248,117 B1 | 6/2001 | Blatter |
| 6,250,532 B1 | 6/2001 | Green et al. |
| 6,254,534 B1 | 7/2001 | Butler et al. |
| 6,258,107 B1 | 7/2001 | Balázs et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,309,403 B1 | 10/2001 | Minor et al. |
| 6,315,184 B1 | 11/2001 | Whitman |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,338,737 B1 | 1/2002 | Toledano |
| 6,346,077 B1 | 2/2002 | Taylor et al. |
| 6,352,503 B1 | 3/2002 | Matsui et al. |
| 6,364,888 B1 | 4/2002 | Niemeyer et al. |

(56) References Cited

U.S. PATENT DOCUMENTS

| | | | |
|---|---|---|---|
| 6,387,113 B1 | 5/2002 | Hawkins et al. | |
| 6,391,038 B2 | 5/2002 | Vargas et al. | |
| 6,398,797 B2 | 6/2002 | Bombard et al. | |
| 6,402,766 B2 | 6/2002 | Bowman et al. | |
| 6,402,780 B2 * | 6/2002 | Williamson, IV | A61B 17/0469 606/153 |
| RE37,814 E | 8/2002 | Allgeyer | |
| 6,436,110 B2 | 8/2002 | Bowman et al. | |
| 6,436,122 B1 | 8/2002 | Frank et al. | |
| 6,440,146 B2 | 8/2002 | Nicholas et al. | |
| 6,443,973 B1 | 9/2002 | Whitman | |
| 6,447,523 B1 | 9/2002 | Middleman et al. | |
| 6,450,391 B1 | 9/2002 | Kayan et al. | |
| 6,458,077 B1 | 10/2002 | Boebel et al. | |
| 6,488,196 B1 | 12/2002 | Fenton, Jr. | |
| 6,488,197 B1 | 12/2002 | Whitman | |
| 6,491,201 B1 | 12/2002 | Whitman | |
| 6,491,701 B2 | 12/2002 | Tierney et al. | |
| 6,494,885 B1 | 12/2002 | Dhindsa | |
| 6,503,257 B2 | 1/2003 | Grant et al. | |
| 6,503,259 B2 | 1/2003 | Huxel et al. | |
| 6,505,768 B2 | 1/2003 | Whitman | |
| 6,510,854 B2 | 1/2003 | Goble | |
| 6,517,528 B1 | 2/2003 | Pantages et al. | |
| 6,517,565 B1 | 2/2003 | Whitman et al. | |
| 6,517,566 B1 | 2/2003 | Hovland et al. | |
| 6,533,157 B1 | 3/2003 | Whitman | |
| 6,543,456 B1 | 4/2003 | Freeman | |
| 6,551,333 B2 | 4/2003 | Kuhns et al. | |
| 6,569,171 B2 | 5/2003 | DeGuillebon et al. | |
| 6,578,751 B2 | 6/2003 | Hartwick | |
| 6,582,364 B2 | 6/2003 | Butler et al. | |
| 6,588,643 B2 | 7/2003 | Bolduc et al. | |
| 6,592,597 B2 | 7/2003 | Grant et al. | |
| 6,601,749 B2 | 8/2003 | Sullivan et al. | |
| 6,605,078 B2 | 8/2003 | Adams | |
| 6,616,686 B2 | 9/2003 | Coleman et al. | |
| 6,619,529 B2 | 9/2003 | Green et al. | |
| 6,629,630 B2 | 10/2003 | Adams | |
| 6,629,988 B2 | 10/2003 | Weadock | |
| 6,638,285 B2 | 10/2003 | Gabbay | |
| 6,638,297 B1 | 10/2003 | Huitema | |
| 6,644,532 B2 | 11/2003 | Green et al. | |
| 6,645,201 B1 | 11/2003 | Utley et al. | |
| 6,656,193 B2 | 12/2003 | Grant et al. | |
| 6,666,854 B1 | 12/2003 | Lange | |
| 6,681,978 B2 | 1/2004 | Geiste et al. | |
| 6,681,979 B2 | 1/2004 | Whitman | |
| 6,692,507 B2 | 2/2004 | Pugsley et al. | |
| 6,695,199 B2 | 2/2004 | Whitman | |
| 6,698,643 B2 | 3/2004 | Whitman | |
| 6,699,235 B2 | 3/2004 | Wallace et al. | |
| 6,716,232 B1 | 4/2004 | Vidal et al. | |
| 6,716,233 B1 | 4/2004 | Whitman | |
| 6,722,552 B2 | 4/2004 | Fenton, Jr. | |
| 6,723,087 B2 | 4/2004 | O'Neill et al. | |
| 6,726,697 B2 | 4/2004 | Nicholas et al. | |
| 6,736,825 B2 | 5/2004 | Blatter et al. | |
| 6,755,338 B2 | 6/2004 | Hahnen et al. | |
| 6,769,590 B2 | 8/2004 | Vresh et al. | |
| 6,769,594 B2 | 8/2004 | Orban, III | |
| 6,780,151 B2 | 8/2004 | Grabover et al. | |
| 6,786,382 B1 | 9/2004 | Hoffman | |
| 6,786,896 B1 | 9/2004 | Madani et al. | |
| 6,793,652 B1 | 9/2004 | Whitman et al. | |
| 6,805,273 B2 | 10/2004 | Bilotti et al. | |
| 6,817,508 B1 | 11/2004 | Racenet et al. | |
| 6,817,509 B2 | 11/2004 | Geiste et al. | |
| 6,821,284 B2 | 11/2004 | Sturtz et al. | |
| 6,827,712 B2 | 12/2004 | Tovey et al. | |
| 6,830,174 B2 | 12/2004 | Hillstead et al. | |
| 6,835,199 B2 | 12/2004 | McGuckin, Jr. et al. | |
| 6,843,403 B2 | 1/2005 | Whitman | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| RE38,708 E | 3/2005 | Bolanos et al. | |
| 6,866,178 B2 | 3/2005 | Adams et al. | |
| 6,866,671 B2 | 3/2005 | Tierney et al. | |
| 6,872,214 B2 | 3/2005 | Sonnenschein et al. | |
| 6,874,669 B2 | 4/2005 | Adams et al. | |
| 6,877,647 B2 | 4/2005 | Green et al. | |
| 6,905,057 B2 | 6/2005 | Swayze et al. | |
| 6,913,608 B2 | 7/2005 | Liddicoat et al. | |
| 6,913,613 B2 | 7/2005 | Schwarz et al. | |
| 6,936,042 B2 | 8/2005 | Wallace et al. | |
| 6,939,358 B2 | 9/2005 | Palacios et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,851 B2 | 11/2005 | Heinrich | |
| 6,960,220 B2 | 11/2005 | Marino et al. | |
| 6,964,363 B2 | 11/2005 | Wales et al. | |
| 6,971,988 B2 | 12/2005 | Orban, III | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,981,978 B2 | 1/2006 | Gannoe | |
| 6,986,451 B1 | 1/2006 | Mastri et al. | |
| 6,988,650 B2 | 1/2006 | Schwemberger et al. | |
| 7,000,818 B2 | 2/2006 | Shelton, IV et al. | |
| 7,000,819 B2 | 2/2006 | Swayze et al. | |
| 7,001,408 B2 | 2/2006 | Knodel et al. | |
| 7,032,798 B2 | 4/2006 | Whitman et al. | |
| 7,032,799 B2 | 4/2006 | Viola et al. | |
| 7,044,352 B2 | 5/2006 | Shelton, IV et al. | |
| 7,044,353 B2 | 5/2006 | Mastri et al. | |
| 7,052,454 B2 | 5/2006 | Taylor | |
| 7,055,731 B2 | 6/2006 | Shelton, IV et al. | |
| 7,056,330 B2 | 6/2006 | Gayton | |
| 7,059,331 B2 | 6/2006 | Adams et al. | |
| 7,063,712 B2 | 6/2006 | Vargas et al. | |
| 7,066,944 B2 | 6/2006 | Laufer et al. | |
| 7,070,083 B2 | 7/2006 | Jankowski | |
| 7,077,856 B2 | 7/2006 | Whitman | |
| 7,080,769 B2 | 7/2006 | Vresh et al. | |
| 7,083,075 B2 | 8/2006 | Swayze et al. | |
| 7,083,626 B2 | 8/2006 | Hart et al. | |
| 7,087,071 B2 | 8/2006 | Nicholas et al. | |
| 7,090,683 B2 | 8/2006 | Brock et al. | |
| 7,094,247 B2 | 8/2006 | Monassevitch et al. | |
| 7,108,701 B2 | 9/2006 | Evens et al. | |
| 7,108,709 B2 | 9/2006 | Cummins | |
| 7,111,769 B2 | 9/2006 | Wales et al. | |
| 7,114,642 B2 | 10/2006 | Whitman | |
| 7,121,446 B2 | 10/2006 | Arad et al. | |
| 7,122,028 B2 | 10/2006 | Looper et al. | |
| 7,128,253 B2 | 10/2006 | Mastri et al. | |
| 7,128,254 B2 | 10/2006 | Shelton, IV et al. | |
| 7,128,748 B2 | 10/2006 | Mooradian et al. | |
| 7,131,445 B2 | 11/2006 | Amoah | |
| 7,134,587 B2 | 11/2006 | Schwemberger et al. | |
| 7,140,527 B2 | 11/2006 | Ehrenfels et al. | |
| 7,147,138 B2 | 12/2006 | Shelton, IV | |
| 7,147,139 B2 | 12/2006 | Schwemberger et al. | |
| 7,147,650 B2 | 12/2006 | Lee | |
| 7,156,863 B2 | 1/2007 | Sonnenschein et al. | |
| 7,159,750 B2 | 1/2007 | Racenet et al. | |
| 7,168,604 B2 | 1/2007 | Milliman et al. | |
| 7,179,267 B2 | 2/2007 | Nolan et al. | |
| 7,182,239 B1 | 2/2007 | Myers | |
| 7,188,758 B2 | 3/2007 | Viola et al. | |
| 7,207,471 B2 | 4/2007 | Heinrich et al. | |
| 7,207,472 B2 | 4/2007 | Wukusick et al. | |
| 7,208,005 B2 | 4/2007 | Frecker et al. | |
| 7,210,609 B2 | 5/2007 | Leiboff et al. | |
| 7,213,736 B2 | 5/2007 | Wales et al. | |
| 7,220,272 B2 | 5/2007 | Weadock | |
| 7,225,964 B2 | 6/2007 | Mastri et al. | |
| 7,229,408 B2 | 6/2007 | Douglas et al. | |
| 7,234,624 B2 | 6/2007 | Gresham et al. | |
| 7,237,708 B1 | 7/2007 | Guy et al. | |
| 7,238,195 B2 | 7/2007 | Viola | |

(56) References Cited

U.S. PATENT DOCUMENTS

| | | | |
|---|---|---|---|
| 7,241,288 B2 | 7/2007 | Braun |
| 7,246,734 B2 | 7/2007 | Shelton, IV |
| 7,252,660 B2 | 8/2007 | Kunz |
| 7,258,262 B2 | 8/2007 | Mastri et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,296,722 B2 | 11/2007 | Ivanko |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,334,718 B2 | 2/2008 | McAlister et al. |
| 7,338,505 B2 | 3/2008 | Belson |
| 7,338,513 B2 | 3/2008 | Lee et al. |
| 7,343,920 B2 | 3/2008 | Toby et al. |
| RE40,237 E | 4/2008 | Bilotti et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,075 B2 | 8/2008 | Holsten et al. |
| 7,407,076 B2 | 8/2008 | Racenet et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,455,682 B2 | 11/2008 | Viola |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,473,221 B2 | 1/2009 | Ewers et al. |
| 7,481,347 B2 | 1/2009 | Roy |
| 7,481,349 B2 | 1/2009 | Holsten et al. |
| 7,481,824 B2 | 1/2009 | Boudreaux et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,517,356 B2 | 4/2009 | Heinrich |
| 7,524,320 B2 | 4/2009 | Tierney et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,556,185 B2 | 7/2009 | Viola |
| 7,559,449 B2 | 7/2009 | Viola |
| 7,559,450 B2 | 7/2009 | Wales et al. |
| 7,559,452 B2 | 7/2009 | Wales et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,624,902 B2 | 12/2009 | Marczyk et al. |
| 7,624,903 B2 | 12/2009 | Green et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,641,095 B2 | 1/2010 | Viola |
| 7,644,848 B2 | 1/2010 | Swayze et al. |
| 7,648,519 B2 | 1/2010 | Lee et al. |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,682,686 B2 | 3/2010 | Curro et al. |
| 7,686,201 B2 | 3/2010 | Csiky |
| 7,686,826 B2 | 3/2010 | Lee et al. |
| 7,691,098 B2 | 4/2010 | Wallace et al. |
| 7,699,204 B2 | 4/2010 | Viola |
| 7,699,844 B2 | 4/2010 | Utley et al. |
| 7,699,859 B2 | 4/2010 | Bombard et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,717,312 B2 | 5/2010 | Beetel |
| 7,717,313 B2 | 5/2010 | Criscuolo et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shelton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,736,306 B2 | 6/2010 | Brustad et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,624 B2 | 6/2010 | Bettuchi |
| 7,744,628 B2 | 6/2010 | Viola |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |

(56) References Cited

U.S. PATENT DOCUMENTS

| | | |
|---|---|---|
| 7,766,210 B2 | 8/2010 | Shelton, IV et al. |
| 7,766,821 B2 | 8/2010 | Brunnen et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,776,060 B2 | 8/2010 | Mooradian et al. |
| 7,780,054 B2 | 8/2010 | Wales |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schell et al. |
| 7,799,039 B2 | 9/2010 | Shelton, IV et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,592 B2 | 11/2010 | Bettuchi et al. |
| 7,824,426 B2 | 11/2010 | Racenet et al. |
| 7,828,189 B2 | 11/2010 | Holsten et al. |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,842,028 B2 | 11/2010 | Lee |
| 7,845,533 B2 | 12/2010 | Marczyk et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,862,502 B2 | 1/2011 | Pool et al. |
| 7,866,527 B2 | 1/2011 | Hall et al. |
| 7,871,418 B2 | 1/2011 | Thompson et al. |
| 7,879,070 B2 | 2/2011 | Ortiz et al. |
| 7,883,461 B2 | 2/2011 | Albrecht et al. |
| 7,891,531 B1 | 2/2011 | Ward |
| 7,891,532 B2 | 2/2011 | Mastri et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,376 B1 | 4/2011 | Knodel et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,934,630 B2 | 5/2011 | Shelton, IV et al. |
| 7,934,631 B2 | 5/2011 | Balbierz et al. |
| 7,938,307 B2 | 5/2011 | Bettuchi |
| 7,942,890 B2 | 5/2011 | D'Agostino et al. |
| 7,950,560 B2 | 5/2011 | Zemlok et al. |
| 7,950,561 B2 | 5/2011 | Aranyi |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,959,051 B2 | 6/2011 | Smith et al. |
| 7,963,432 B2 | 6/2011 | Knodel et al. |
| 7,966,799 B2 | 6/2011 | Morgan et al. |
| 7,967,180 B2 | 6/2011 | Scirica |
| 7,967,181 B2 | 6/2011 | Viola et al. |
| 7,967,791 B2 | 6/2011 | Franer et al. |
| 7,980,443 B2 | 7/2011 | Scheib et al. |
| 7,981,132 B2 | 7/2011 | Dubrul et al. |
| 7,988,026 B2 | 8/2011 | Knodel et al. |
| 7,988,027 B2 | 8/2011 | Olson et al. |
| 7,992,757 B2 | 8/2011 | Wheeler et al. |
| 7,997,469 B2 | 8/2011 | Olson et al. |
| 8,002,696 B2 | 8/2011 | Suzuki |
| 8,002,795 B2 | 8/2011 | Beetel |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,883 B2 | 10/2011 | Stopek |
| 8,028,885 B2 | 10/2011 | Smith et al. |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,043,328 B2 | 10/2011 | Hahnen et al. |
| 8,056,787 B2 | 11/2011 | Boudreaux et al. |
| 8,056,788 B2 | 11/2011 | Mastri et al. |
| 8,066,167 B2 | 11/2011 | Measamer et al. |
| D650,074 S | 12/2011 | Hunt et al. |
| 8,075,476 B2 | 12/2011 | Vargas |
| 8,083,119 B2 | 12/2011 | Prommersberger |
| 8,083,120 B2 | 12/2011 | Shelton, IV et al. |
| 8,091,756 B2 | 1/2012 | Viola |
| 8,097,017 B2 | 1/2012 | Viola |
| 8,100,310 B2 | 1/2012 | Zemlok |
| 8,105,350 B2 | 1/2012 | Lee et al. |
| 8,109,426 B2 | 2/2012 | Milliman et al. |
| 8,113,410 B2 | 2/2012 | Hall et al. |
| 8,114,100 B2 | 2/2012 | Smith et al. |
| 8,123,103 B2 | 2/2012 | Milliman |
| 8,123,767 B2 | 2/2012 | Bauman et al. |
| 8,128,645 B2 | 3/2012 | Sonnenschein et al. |
| 8,136,712 B2 | 3/2012 | Zingman |
| 8,141,762 B2 | 3/2012 | Bedi et al. |
| 8,141,763 B2 | 3/2012 | Milliman |
| 8,152,041 B2 | 4/2012 | Kostrzewski |
| 8,157,145 B2 | 4/2012 | Shelton, IV et al. |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,197 B2 | 4/2012 | Mastri et al. |
| 8,167,185 B2 | 5/2012 | Shelton, IV et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,186,555 B2 | 5/2012 | Shelton, IV et al. |
| 8,186,560 B2 | 5/2012 | Hess et al. |
| 8,191,752 B2 | 6/2012 | Scirica |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,781 B2 | 6/2012 | Baxter et al. |
| 8,210,411 B2 | 7/2012 | Yates et al. |

(56) References Cited

U.S. PATENT DOCUMENTS

| | | |
|---|---|---|
| 8,210,414 B2 | 7/2012 | Bettuchi et al. |
| 8,210,415 B2 | 7/2012 | Ward |
| 8,211,125 B2 | 7/2012 | Spivey |
| 8,215,531 B2 | 7/2012 | Shelton, IV et al. |
| 8,215,533 B2 | 7/2012 | Viola et al. |
| 8,220,688 B2 | 7/2012 | Laurent et al. |
| 8,220,690 B2 | 7/2012 | Hess et al. |
| 8,225,799 B2 | 7/2012 | Bettuchi |
| 8,226,553 B2 | 7/2012 | Shelton, IV et al. |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,899 B2 | 8/2012 | Swensgard et al. |
| 8,245,901 B2 | 8/2012 | Stopek |
| 8,256,654 B2 | 9/2012 | Bettuchi et al. |
| 8,256,655 B2 | 9/2012 | Sniffin et al. |
| 8,257,251 B2 | 9/2012 | Shelton, IV et al. |
| 8,267,300 B2 | 9/2012 | Boudreaux |
| 8,272,553 B2 | 9/2012 | Mastri et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,286,845 B2 | 10/2012 | Perry et al. |
| 8,287,561 B2 | 10/2012 | Nunez et al. |
| 8,292,151 B2 | 10/2012 | Viola |
| 8,292,155 B2 | 10/2012 | Shelton, IV et al. |
| 8,292,157 B2 | 10/2012 | Smith et al. |
| 8,308,040 B2 | 11/2012 | Huang et al. |
| 8,308,042 B2 | 11/2012 | Aranyi |
| 8,308,046 B2 | 11/2012 | Prommersberger |
| 8,317,070 B2 | 11/2012 | Hueil et al. |
| 8,317,074 B2 | 11/2012 | Ortiz et al. |
| 8,322,455 B2 | 12/2012 | Shelton, IV et al. |
| 8,322,589 B2 | 12/2012 | Boudreaux |
| 8,328,062 B2 | 12/2012 | Viola |
| 8,328,063 B2 | 12/2012 | Milliman et al. |
| 8,328,064 B2 | 12/2012 | Racenet et al. |
| 8,333,313 B2 | 12/2012 | Boudreaux et al. |
| 8,348,123 B2 | 1/2013 | Scirica et al. |
| 8,348,129 B2 | 1/2013 | Bedi et al. |
| 8,348,131 B2 | 1/2013 | Omaits et al. |
| 8,348,837 B2 | 1/2013 | Wenchell |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,299 B2 | 1/2013 | Zemlok et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,669 B2 | 3/2013 | Kim |
| 8,403,198 B2 | 3/2013 | Sorrentino et al. |
| 8,408,439 B2 | 4/2013 | Huang et al. |
| 8,408,442 B2 | 4/2013 | Racenet et al. |
| 8,409,079 B2 | 4/2013 | Oakamoto et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,424,740 B2 | 4/2013 | Shelton, IV et al. |
| 8,424,741 B2 | 4/2013 | McGuckin, Jr. et al. |
| 8,444,036 B2 | 5/2013 | Shelton, IV |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,925 B2 | 6/2013 | Hull et al. |
| 8,465,515 B2 | 6/2013 | Drew et al. |
| 8,474,677 B2 | 7/2013 | Woodard, Jr. et al. |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,490,853 B2 | 7/2013 | Criscuolo et al. |
| 8,496,156 B2 | 7/2013 | Sniffin et al. |
| 8,499,993 B2 | 8/2013 | Shelton, IV et al. |
| 8,517,239 B2 | 8/2013 | Scheib et al. |
| 8,517,243 B2 | 8/2013 | Giordano et al. |
| 8,517,244 B2 | 8/2013 | Shelton, IV et al. |
| 8,529,600 B2 | 9/2013 | Woodard, Jr. et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,561,870 B2 | 10/2013 | Baxter, III et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,579,176 B2 | 11/2013 | Smith et al. |
| 8,579,937 B2 | 11/2013 | Gresham |
| 8,584,919 B2 | 11/2013 | Hueil et al. |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,608,044 B2 | 12/2013 | Hueil et al. |
| 8,608,045 B2 | 12/2013 | Smith et al. |
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,736 B2 | 1/2014 | Yates et al. |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,668,130 B2 | 3/2014 | Hess et al. |
| 8,672,207 B2 | 3/2014 | Shelton, IV et al. |
| 8,672,208 B2 | 3/2014 | Hess et al. |
| 8,684,253 B2 | 4/2014 | Giordano et al. |
| 8,695,866 B2 | 4/2014 | Leimbach et al. |
| 8,701,958 B2 | 4/2014 | Shelton, IV et al. |
| 8,708,213 B2 | 4/2014 | Shelton, IV et al. |
| 8,720,766 B2 | 5/2014 | Hess et al. |
| 8,727,197 B2 | 5/2014 | Hess et al. |
| 8,727,961 B2 | 5/2014 | Ziv |
| 8,733,613 B2 | 5/2014 | Huitema et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |

(56) References Cited

U.S. PATENT DOCUMENTS

| | | |
|---|---|---|
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,794,497 B2 | 8/2014 | Zingman |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,814,024 B2 | 8/2014 | Woodard, Jr. et al. |
| 8,820,603 B2 | 9/2014 | Shelton, IV et al. |
| 8,820,605 B2 | 9/2014 | Shelton, IV |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,465 B2 | 12/2014 | Shelton, IV et al. |
| 8,899,466 B2 | 12/2014 | Baxter, III et al. |
| 8,911,471 B2 | 12/2014 | Spivey et al. |
| 8,925,782 B2 | 1/2015 | Shelton, IV |
| 8,925,788 B2 | 1/2015 | Hess et al. |
| 8,926,598 B2 | 1/2015 | Mollere et al. |
| 8,931,682 B2 | 1/2015 | Timm et al. |
| 8,973,803 B2 | 3/2015 | Hall et al. |
| 8,973,804 B2 | 3/2015 | Hess et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,998,058 B2 | 4/2015 | Moore et al. |
| 9,005,230 B2 | 4/2015 | Yates et al. |
| 9,016,542 B2 | 4/2015 | Shelton, IV et al. |
| 9,028,494 B2 | 5/2015 | Shelton, IV et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,044,227 B2 | 6/2015 | Shelton, IV et al. |
| 9,044,228 B2 | 6/2015 | Woodard, Jr. et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,089,330 B2 | 7/2015 | Widenhouse et al. |
| 9,095,339 B2 | 8/2015 | Moore et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,883 B2 | 8/2015 | Aronhalt et al. |
| 9,113,884 B2 | 8/2015 | Shelton, IV et al. |
| 9,119,957 B2 | 9/2015 | Shelton, IV et al. |
| 9,125,654 B2 | 9/2015 | Aronhalt et al. |
| 9,125,662 B2 | 9/2015 | Shelton, IV |
| 9,138,225 B2 | 9/2015 | Huang et al. |
| 9,149,274 B2 | 10/2015 | Spivey et al. |
| 9,211,122 B2 | 12/2015 | Hagerty et al. |
| 2001/0025183 A1 | 9/2001 | Shahidi |
| 2002/0095175 A1 | 7/2002 | Brock et al. |
| 2002/0103494 A1 | 8/2002 | Pacey |
| 2002/0117534 A1 | 8/2002 | Green et al. |
| 2003/0190584 A1 | 10/2003 | Heasley |
| 2003/0220660 A1 | 11/2003 | Kortenbach et al. |
| 2004/0006372 A1 | 1/2004 | Racenet et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0108357 A1 | 6/2004 | Milliman et al. |
| 2004/111081 A1 | 6/2004 | Whitman et al. |
| 2004/0147909 A1 | 7/2004 | Johnston et al. |
| 2004/0158261 A1 | 8/2004 | Vu |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0193177 A1 | 9/2004 | Houghton et al. |
| 2004/0193189 A1 | 9/2004 | Kortenbach et al. |
| 2004/0222268 A1 | 11/2004 | Bilotti et al. |
| 2004/0232201 A1 | 11/2004 | Wenchell et al. |
| 2004/0243147 A1 | 12/2004 | Lipow |
| 2004/0243176 A1 | 12/2004 | Hahnen et al. |
| 2004/0254566 A1 | 12/2004 | Plicchi et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0033357 A1 | 2/2005 | Braun |
| 2005/0059996 A1* | 3/2005 | Bauman .......... A61B 17/072 606/215 |
| 2005/0059997 A1 | 3/2005 | Bauman et al. |
| 2005/0070929 A1 | 3/2005 | Dalessandro et al. |
| 2005/0085693 A1 | 4/2005 | Belson et al. |
| 2005/0103819 A1 | 5/2005 | Racenet et al. |
| 2005/0107824 A1 | 5/2005 | Hillstead et al. |
| 2005/0131390 A1 | 6/2005 | Heinrich et al. |
| 2005/0131457 A1 | 6/2005 | Douglas et al. |
| 2005/0145675 A1 | 7/2005 | Hartwick et al. |
| 2005/0154406 A1 | 7/2005 | Bombard et al. |
| 2005/0177181 A1 | 8/2005 | Kagan et al. |
| 2005/0182298 A1 | 8/2005 | Ikeda et al. |
| 2005/0187576 A1 | 8/2005 | Whitman et al. |
| 2005/0189397 A1 | 9/2005 | Jankowski |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0240222 A1 | 10/2005 | Shipp |
| 2005/0256452 A1 | 11/2005 | DeMarchi et al. |
| 2005/0263563 A1 | 12/2005 | Racenet et al. |
| 2005/0274768 A1 | 12/2005 | Cummins et al. |
| 2005/0283188 A1 | 12/2005 | Loshakove et al. |
| 2006/0011699 A1 | 1/2006 | Olson et al. |
| 2006/0020258 A1 | 1/2006 | Strauss et al. |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0041188 A1 | 2/2006 | Dirusso et al. |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0108393 A1 | 5/2006 | Heinrich et al. |
| 2006/0122636 A1 | 6/2006 | Bailly et al. |

(56) References Cited

U.S. PATENT DOCUMENTS

| | | |
|---|---|---|
| 2006/0161050 A1 | 7/2006 | Butler et al. |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0185682 A1 | 8/2006 | Marczyk |
| 2006/0201989 A1 | 9/2006 | Ojeda |
| 2006/0212069 A1 | 9/2006 | Shelton, IV |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0034668 A1 | 2/2007 | Holsten et al. |
| 2007/0043387 A1 | 2/2007 | Vargas et al. |
| 2007/0055219 A1 | 3/2007 | Whitman et al. |
| 2007/0066981 A1 | 3/2007 | Meagher |
| 2007/0073341 A1 | 3/2007 | Smith |
| 2007/0078484 A1 | 4/2007 | Talarico et al. |
| 2007/0084897 A1 | 4/2007 | Shelton, IV et al. |
| 2007/0093869 A1 | 4/2007 | Bloom et al. |
| 2007/0102472 A1 | 5/2007 | Shelton, IV |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135803 A1 | 6/2007 | Belson |
| 2007/0170225 A1 | 7/2007 | Shelton, IV et al. |
| 2007/0173687 A1 | 7/2007 | Shima et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0219571 A1 | 9/2007 | Balbierz et al. |
| 2007/0221700 A1 | 9/2007 | Ortiz et al. |
| 2007/0225562 A1 | 9/2007 | Spivey et al. |
| 2007/0239028 A1 | 10/2007 | Houser et al. |
| 2007/0244471 A1 | 10/2007 | Malackowski |
| 2007/0246505 A1 | 10/2007 | Pace-Floridia et al. |
| 2007/0270784 A1 | 11/2007 | Smith et al. |
| 2007/0276189 A1 | 11/2007 | Abel et al. |
| 2007/0287993 A1 | 12/2007 | Hinman et al. |
| 2007/0299427 A1 | 12/2007 | Yeung et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041917 A1 | 2/2008 | Racenet et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0083808 A1 | 4/2008 | Scirica |
| 2008/0083813 A1 | 4/2008 | Zemlok et al. |
| 2008/0140115 A1 | 6/2008 | Stopek |
| 2008/0154299 A1 | 6/2008 | Linvneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0197167 A1 | 8/2008 | Viola et al. |
| 2008/0200933 A1 | 8/2008 | Bakos et al. |
| 2008/0242939 A1 | 10/2008 | Johnston |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0255519 A1 | 10/2008 | Piskun et al. |
| 2008/0283570 A1 | 11/2008 | Boyden et al. |
| 2008/0290134 A1 | 11/2008 | Bettuchi et al. |
| 2008/0294179 A1 | 11/2008 | Balbierz et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001130 A1 | 1/2009 | Hess et al. |
| 2009/0005809 A1 | 1/2009 | Hess et al. |
| 2009/0012534 A1 | 1/2009 | Madhani et al. |
| 2009/0048612 A1 | 2/2009 | Farritor et al. |
| 2009/0054908 A1 | 2/2009 | Zand et al. |
| 2009/0078736 A1 | 3/2009 | Van Lue |
| 2009/0088774 A1 | 4/2009 | Swarup et al. |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0149871 A9 | 6/2009 | Kagan et al. |
| 2009/0157087 A1 | 6/2009 | Wei et al. |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0277949 A1 | 11/2009 | Viola et al. |
| 2009/0292176 A1 | 11/2009 | Bonadio et al. |
| 2010/0012704 A1 | 1/2010 | Tarinelli Racenet et al. |
| 2010/0069942 A1 | 3/2010 | Shelton, IV |
| 2010/0072254 A1 | 3/2010 | Aranyi et al. |
| 2010/0087840 A1 | 4/2010 | Ebersole et al. |
| 2010/0108740 A1 | 5/2010 | Pastorelli et al. |
| 2010/0108741 A1 | 5/2010 | Hessler et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0163598 A1 | 7/2010 | Belzer |
| 2010/0193566 A1 | 8/2010 | Schieb et al. |
| 2010/0200637 A1 | 8/2010 | Beetel |
| 2010/0222901 A1 | 9/2010 | Swayze et al. |
| 2010/0228091 A1 | 9/2010 | Widenhouse et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249519 A1 | 9/2010 | Park et al. |
| 2010/0258611 A1 | 10/2010 | Smith et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0305552 A1 | 12/2010 | Shelton, IV et al. |
| 2010/0312261 A1 | 12/2010 | Suzuki et al. |
| 2010/0320252 A1 | 12/2010 | Viola et al. |
| 2010/0331880 A1 | 12/2010 | Stopek |
| 2011/0006101 A1 | 1/2011 | Hall et al. |
| 2011/0011916 A1 | 1/2011 | Levine |
| 2011/0017801 A1 | 1/2011 | Zemlok et al. |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |

(56) References Cited

U.S. PATENT DOCUMENTS

| | | |
|---|---|---|
| 2011/0036887 A1 | 2/2011 | Zemlok et al. |
| 2011/0036891 A1 | 2/2011 | Zemlok et al. |
| 2011/0060363 A1 | 3/2011 | Hess et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0118754 A1 | 5/2011 | Dachs, II et al. |
| 2011/0118778 A1 | 5/2011 | Burbank |
| 2011/0125176 A1 | 5/2011 | Yates et al. |
| 2011/0147433 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0210156 A1 | 9/2011 | Smith et al. |
| 2011/0253765 A1 | 10/2011 | Nicholas et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2012/0029272 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0074200 A1 | 3/2012 | Schmid et al. |
| 2012/0080336 A1 | 4/2012 | Shelton, IV et al. |
| 2012/0080338 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080475 A1 | 4/2012 | Smith et al. |
| 2012/0080478 A1 | 4/2012 | Morgan et al. |
| 2012/0080488 A1 | 4/2012 | Shelton, IV et al. |
| 2012/0080498 A1 | 4/2012 | Shelton, IV et al. |
| 2012/0083835 A1 | 4/2012 | Shelton, IV et al. |
| 2012/0138658 A1 | 6/2012 | Ullrich et al. |
| 2012/0150192 A1 | 6/2012 | Dachs, II et al. |
| 2012/0175398 A1 | 7/2012 | Sandborn et al. |
| 2012/0187179 A1 | 7/2012 | Gleiman |
| 2012/0199632 A1 | 8/2012 | Spivey et al. |
| 2012/0223123 A1 | 9/2012 | Baxter, III et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0273550 A1 | 11/2012 | Scirica |
| 2012/0283707 A1 | 11/2012 | Giordano et al. |
| 2012/0283748 A1 | 11/2012 | Ortiz et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325892 A1 | 12/2012 | Kostrzewski |
| 2013/0018228 A1 | 1/2013 | Armstrong |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0037596 A1 | 2/2013 | Bear et al. |
| 2013/0048697 A1 | 2/2013 | Shelton, IV et al. |
| 2013/0056518 A1 | 3/2013 | Swensgard |
| 2013/0062391 A1 | 3/2013 | Boudreaux et al. |
| 2013/0075449 A1 | 3/2013 | Schmid et al. |
| 2013/0079814 A1 | 3/2013 | Hess et al. |
| 2013/0087597 A1 | 4/2013 | Shelton, IV et al. |
| 2013/0116668 A1 | 5/2013 | Shelton, IV et al. |
| 2013/0116669 A1 | 5/2013 | Shelton, IV et al. |
| 2013/0126582 A1 | 5/2013 | Shelton, IV et al. |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0150832 A1 | 6/2013 | Belson et al. |
| 2013/0153634 A1 | 6/2013 | Carter et al. |
| 2013/0153636 A1 | 6/2013 | Shelton, IV et al. |
| 2013/0153641 A1 | 6/2013 | Shelton, IV et al. |
| 2013/0161375 A1 | 6/2013 | Huitema et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214030 A1 | 8/2013 | Aronhalt et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0248576 A1 | 9/2013 | Laurent et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0270322 A1 | 10/2013 | Scheib et al. |
| 2013/0277412 A1 | 10/2013 | Gresham et al. |
| 2013/0310873 A1 | 11/2013 | Stopek (nee Prommersberger) et al. |
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |

(56) References Cited

U.S. PATENT DOCUMENTS

| | | |
|---|---|---|
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005679 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005708 A1 | 1/2014 | Shelton, IV |
| 2014/0005718 A1 | 1/2014 | Shelton, IV et al. |
| 2014/0008414 A1 | 1/2014 | Shelton, IV et al. |
| 2014/0014705 A1 | 1/2014 | Baxter, III |
| 2014/0042205 A1 | 2/2014 | Baxter, III et al. |
| 2014/0048582 A1 | 2/2014 | Shelton, IV et al. |
| 2014/0061279 A1 | 3/2014 | Laurent et al. |
| 2014/0097227 A1 | 4/2014 | Aronhalt et al. |
| 2014/0103093 A1 | 4/2014 | Koch, Jr. et al. |
| 2014/0107640 A1 | 4/2014 | Yates et al. |
| 2014/0128850 A1 | 5/2014 | Kerr et al. |
| 2014/0151433 A1 | 6/2014 | Shelton, IV et al. |
| 2014/0151434 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0175155 A1 | 6/2014 | Shelton, IV et al. |
| 2014/0191014 A1 | 7/2014 | Shelton, IV |
| 2014/0191015 A1 | 7/2014 | Shelton, IV |
| 2014/0205637 A1 | 7/2014 | Widenhouse et al. |
| 2014/0207166 A1 | 7/2014 | Shelton, IV et al. |
| 2014/0224686 A1 | 8/2014 | Aronhalt et al. |
| 2014/0224857 A1 | 8/2014 | Schmid |
| 2014/0236184 A1 | 8/2014 | Leimbach et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263537 A1 | 9/2014 | Leimbach et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263564 A1 | 9/2014 | Leimbach et al. |
| 2014/0263565 A1 | 9/2014 | Lytle, IV et al. |
| 2014/0263571 A1 | 9/2014 | Morgan et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291381 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0303645 A1 | 10/2014 | Morgan et al. |
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305993 A1 | 10/2014 | Timm et al. |
| 2014/0305994 A1 | 10/2014 | Parihar et al. |
| 2014/0305995 A1 | 10/2014 | Shelton, IV et al. |
| 2014/0309665 A1 | 10/2014 | Parihar et al. |
| 2014/0309666 A1 | 10/2014 | Shelton, IV et al. |
| 2015/0122869 A1 | 5/2015 | Aronhalt et al. |
| 2015/0230784 A1 | 8/2015 | Shelton, IV et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289870 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0305744 A1 | 10/2015 | Moore et al. |
| 2015/0305745 A1 | 10/2015 | Baxter, III et al. |

(56) References Cited

U.S. PATENT DOCUMENTS

| | | |
|---|---|---|
| 2015/0313591 A1 | 11/2015 | Baxter, III et al. |
| 2015/0313594 A1 | 11/2015 | Shelton, IV et al. |
| 2015/0327853 A1 | 11/2015 | Aronhalt et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 1163558 A | 10/1997 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101541251 A | 9/2009 |
| CN | 101675898 A | 3/2010 |
| CN | 101683280 A | 3/2010 |
| CN | 102188270 A | 9/2011 |
| CN | 101534723 B | 1/2012 |
| CN | 101507633 B | 2/2013 |
| CN | 101023879 B | 3/2013 |
| CN | 101401736 B | 6/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20121753 U1 | 4/2003 |
| DE | 10314827 B3 | 4/2004 |
| DE | 10314072 A1 | 10/2004 |
| DE | 202007003114 U1 | 6/2007 |
| DE | 20112837 U1 | 10/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0379721 B1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 B1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |

(56) References Cited

FOREIGN PATENT DOCUMENTS

| | | | |
|---|---|---|---|
| EP | 1256318 | B1 | 5/2001 |
| EP | 0806914 | B1 | 9/2001 |
| EP | 0768840 | B1 | 12/2001 |
| EP | 0908152 | B1 | 1/2002 |
| EP | 0717959 | B1 | 2/2002 |
| EP | 0872213 | B1 | 5/2002 |
| EP | 0862386 | B1 | 6/2002 |
| EP | 0949886 | B1 | 9/2002 |
| EP | 1238634 | A2 | 9/2002 |
| EP | 0858295 | B1 | 12/2002 |
| EP | 0656188 | B1 | 1/2003 |
| EP | 0717960 | B1 | 2/2003 |
| EP | 1284120 | A1 | 2/2003 |
| EP | 1287788 | A1 | 3/2003 |
| EP | 0717966 | B1 | 4/2003 |
| EP | 0869742 | B1 | 5/2003 |
| EP | 0829235 | B1 | 6/2003 |
| EP | 0887046 | B1 | 7/2003 |
| EP | 1323384 | A2 | 7/2003 |
| EP | 0852480 | B1 | 8/2003 |
| EP | 0891154 | B1 | 9/2003 |
| EP | 0813843 | B1 | 10/2003 |
| EP | 0873089 | B1 | 10/2003 |
| EP | 0856326 | B1 | 11/2003 |
| EP | 1374788 | A1 | 1/2004 |
| EP | 0741996 | B1 | 2/2004 |
| EP | 0814712 | B1 | 2/2004 |
| EP | 1402837 | A1 | 3/2004 |
| EP | 0705570 | B1 | 4/2004 |
| EP | 0959784 | B1 | 4/2004 |
| EP | 1407719 | A2 | 4/2004 |
| EP | 1086713 | B1 | 5/2004 |
| EP | 0996378 | B1 | 6/2004 |
| EP | 1426012 | A1 | 6/2004 |
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1459695 | A1 | 9/2004 |
| EP | 1254636 | B1 | 10/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1496805 | A2 | 1/2005 |
| EP | 1520521 | A1 | 4/2005 |
| EP | 1520522 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 0906764 | B1 | 12/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621145 | A2 | 2/2006 |
| EP | 1621151 | A2 | 2/2006 |
| EP | 1034746 | B1 | 3/2006 |
| EP | 1201196 | B1 | 3/2006 |
| EP | 1632191 | A2 | 3/2006 |
| EP | 1647231 | A1 | 4/2006 |
| EP | 1065981 | B1 | 5/2006 |
| EP | 1082944 | B1 | 5/2006 |
| EP | 1230899 | B1 | 5/2006 |
| EP | 1652481 | A2 | 5/2006 |
| EP | 1382303 | B1 | 6/2006 |
| EP | 1253866 | B1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1736105 | A1 | 12/2006 |
| EP | 1011494 | B1 | 1/2007 |
| EP | 1479346 | B1 | 1/2007 |
| EP | 1484024 | B1 | 1/2007 |
| EP | 1749485 | A1 | 2/2007 |
| EP | 1754445 | A2 | 2/2007 |
| EP | 1759812 | A1 | 3/2007 |
| EP | 1767157 | A1 | 3/2007 |
| EP | 1767163 | A1 | 3/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1563793 | B1 | 6/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1815950 | A1 | 8/2007 |
| EP | 1330991 | B1 | 9/2007 |
| EP | 1806103 | B1 | 9/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1679096 | B1 | 11/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1917929 | A1 | 5/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943959 | A1 | 7/2008 |
| EP | 1943962 | A2 | 7/2008 |
| EP | 1943964 | A2 | 7/2008 |
| EP | 1943976 | A2 | 7/2008 |
| EP | 1593337 | B1 | 8/2008 |
| EP | 1970014 | A1 | 9/2008 |
| EP | 1974678 | A2 | 10/2008 |
| EP | 1980213 | A2 | 10/2008 |
| EP | 1759645 | B1 | 11/2008 |
| EP | 1987780 | A2 | 11/2008 |

(56) References Cited

FOREIGN PATENT DOCUMENTS

| | | | |
|---|---|---|---|
| EP | 1990014 | A2 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000102 | A2 | 12/2008 |
| EP | 2005894 | A2 | 12/2008 |
| EP | 2005901 | A1 | 12/2008 |
| EP | 2008595 | A2 | 12/2008 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039308 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 2055243 | A2 | 5/2009 |
| EP | 1550409 | A1 | 6/2009 |
| EP | 1550413 | B1 | 6/2009 |
| EP | 1719461 | B1 | 6/2009 |
| EP | 1834594 | B1 | 6/2009 |
| EP | 1709911 | B1 | 7/2009 |
| EP | 2077093 | A2 | 7/2009 |
| EP | 1745748 | B1 | 8/2009 |
| EP | 2090231 | A1 | 8/2009 |
| EP | 2090237 | A1 | 8/2009 |
| EP | 2090241 | A1 | 8/2009 |
| EP | 2090244 | A2 | 8/2009 |
| EP | 2090245 | A1 | 8/2009 |
| EP | 2090254 | A1 | 8/2009 |
| EP | 2090256 | A2 | 8/2009 |
| EP | 2095777 | A2 | 9/2009 |
| EP | 2098170 | A2 | 9/2009 |
| EP | 2110082 | A1 | 10/2009 |
| EP | 2110084 | A2 | 10/2009 |
| EP | 2111803 | A2 | 10/2009 |
| EP | 1762190 | B8 | 11/2009 |
| EP | 1813208 | B1 | 11/2009 |
| EP | 1908426 | B1 | 11/2009 |
| EP | 2116195 | A1 | 11/2009 |
| EP | 2116197 | A2 | 11/2009 |
| EP | 1607050 | B1 | 12/2009 |
| EP | 1815804 | B1 | 12/2009 |
| EP | 1875870 | B1 | 12/2009 |
| EP | 1878395 | B1 | 1/2010 |
| EP | 2151204 | A1 | 2/2010 |
| EP | 1813211 | B1 | 3/2010 |
| EP | 2165656 | A2 | 3/2010 |
| EP | 2165660 | A2 | 3/2010 |
| EP | 1566150 | B1 | 4/2010 |
| EP | 1813206 | B1 | 4/2010 |
| EP | 1769754 | B1 | 6/2010 |
| EP | 1854416 | B1 | 6/2010 |
| EP | 1911408 | B1 | 6/2010 |
| EP | 2198787 | A1 | 6/2010 |
| EP | 1647286 | B1 | 9/2010 |
| EP | 1825821 | B1 | 9/2010 |
| EP | 1535565 | B1 | 10/2010 |
| EP | 1702570 | B1 | 10/2010 |
| EP | 1785098 | B1 | 10/2010 |
| EP | 2005896 | B1 | 10/2010 |
| EP | 2030578 | B1 | 11/2010 |
| EP | 2036505 | B1 | 11/2010 |
| EP | 2245993 | A2 | 11/2010 |
| EP | 2253280 | A1 | 11/2010 |
| EP | 1627605 | B1 | 12/2010 |
| EP | 2027811 | B1 | 12/2010 |
| EP | 2130498 | B1 | 12/2010 |
| EP | 2263568 | A2 | 12/2010 |
| EP | 1994890 | B1 | 1/2011 |
| EP | 2005900 | B1 | 1/2011 |
| EP | 2283780 | A2 | 2/2011 |
| EP | 2286738 | A2 | 2/2011 |
| EP | 1690502 | B1 | 3/2011 |
| EP | 2292153 | A1 | 3/2011 |
| EP | 1769755 | B1 | 4/2011 |
| EP | 2090240 | B1 | 4/2011 |
| EP | 2305135 | A1 | 4/2011 |
| EP | 2308388 | A1 | 4/2011 |
| EP | 2314254 | A2 | 4/2011 |
| EP | 2316345 | A1 | 5/2011 |
| EP | 2316366 | A2 | 5/2011 |
| EP | 1813205 | B1 | 6/2011 |
| EP | 2090243 | B1 | 6/2011 |
| EP | 2329773 | A1 | 6/2011 |
| EP | 2090239 | B1 | 7/2011 |
| EP | 2340771 | A2 | 7/2011 |
| EP | 2353545 | A1 | 8/2011 |
| EP | 2361562 | A1 | 8/2011 |
| EP | 1836986 | B1 | 11/2011 |
| EP | 1908414 | B1 | 11/2011 |
| EP | 2153781 | B1 | 11/2011 |
| EP | 2389928 | A2 | 11/2011 |
| EP | 1847225 | B1 | 12/2011 |
| EP | 2399538 | A2 | 12/2011 |
| EP | 1785102 | B1 | 1/2012 |
| EP | 2090253 | B1 | 3/2012 |
| EP | 2430986 | A2 | 3/2012 |
| EP | 2446834 | A1 | 5/2012 |
| EP | 2455007 | A2 | 5/2012 |
| EP | 2457519 | A1 | 5/2012 |
| EP | 2462878 | A1 | 6/2012 |
| EP | 2462880 | A2 | 6/2012 |
| EP | 1813204 | B1 | 7/2012 |
| EP | 2189121 | B1 | 7/2012 |
| EP | 2248475 | B1 | 7/2012 |
| EP | 2005895 | B1 | 8/2012 |
| EP | 2090248 | B1 | 8/2012 |
| EP | 2481359 | A1 | 8/2012 |
| EP | 2486862 | A2 | 8/2012 |
| EP | 1908412 | B1 | 9/2012 |
| EP | 1935351 | B1 | 9/2012 |
| EP | 2497431 | A1 | 9/2012 |
| EP | 1550412 | B2 | 10/2012 |
| EP | 1616549 | B1 | 10/2012 |
| EP | 2030579 | B1 | 10/2012 |
| EP | 2090252 | B1 | 10/2012 |
| EP | 2517637 | A1 | 10/2012 |
| EP | 2517638 | A1 | 10/2012 |
| EP | 2517642 | A2 | 10/2012 |
| EP | 2517645 | A2 | 10/2012 |
| EP | 2517649 | A2 | 10/2012 |
| EP | 2517651 | A2 | 10/2012 |
| EP | 2526877 | A1 | 11/2012 |
| EP | 1884206 | B1 | 3/2013 |
| EP | 2090238 | B1 | 4/2013 |
| EP | 1982657 | B1 | 7/2013 |
| EP | 2614782 | A2 | 7/2013 |
| EP | 2090234 | B1 | 9/2013 |
| EP | 2633830 | A1 | 9/2013 |
| EP | 2644124 | A1 | 10/2013 |
| EP | 2644209 | A2 | 10/2013 |
| EP | 2649948 | A1 | 10/2013 |
| EP | 2649949 | A1 | 10/2013 |
| EP | 2700367 | A1 | 2/2014 |
| EP | 1772105 | B1 | 5/2014 |
| EP | 2759267 | A2 | 7/2014 |
| EP | 2446835 | B1 | 1/2015 |
| ES | 2396594 | T3 | 2/2013 |
| FR | 459743 | A | 11/1913 |
| FR | 999646 | A | 2/1952 |
| FR | 1112936 | A | 3/1956 |
| FR | 2598905 | A1 | 11/1987 |
| FR | 2765794 | A | 1/1999 |
| FR | 2815842 | | 10/2000 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2272159 | A | 5/1994 |

(56) References Cited

FOREIGN PATENT DOCUMENTS

| | | |
|---|---|---|
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S47-11908 Y1 | 5/1972 |
| JP | 50-33988 U | 4/1975 |
| JP | S56-112235 A | 9/1981 |
| JP | S585500053 A | 1/1983 |
| JP | S58-501360 A | 8/1983 |
| JP | S59-174920 A | 3/1984 |
| JP | 60-100955 A | 6/1985 |
| JP | 60-212152 A | 10/1985 |
| JP | 61-98249 A | 5/1986 |
| JP | S61502036 A | 9/1986 |
| JP | S62-170011 U | 10/1987 |
| JP | S63-147449 A | 10/1987 |
| JP | S63-59764 A | 3/1988 |
| JP | 63-203149 | 8/1988 |
| JP | H02-279149 A | 11/1990 |
| JP | 3-12126 A | 1/1991 |
| JP | H04-215747 A | 8/1992 |
| JP | H4-131860 U | 12/1992 |
| JP | H05-084252 A | 4/1993 |
| JP | H05-123325 A | 5/1993 |
| JP | 5-212039 A | 8/1993 |
| JP | 6007357 A | 1/1994 |
| JP | H6-30945 A | 2/1994 |
| JP | H06-54857 A | 3/1994 |
| JP | H06-26812 U | 4/1994 |
| JP | H6-121798 A | 5/1994 |
| JP | H6-125913 A | 5/1994 |
| JP | H06-197901 A | 7/1994 |
| JP | H06-237937 A | 8/1994 |
| JP | H06-327684 A | 11/1994 |
| JP | 7-31623 A | 2/1995 |
| JP | 7-51273 A | 2/1995 |
| JP | H7-47070 A | 2/1995 |
| JP | 7-124166 A | 5/1995 |
| JP | H7-163574 A | 6/1995 |
| JP | 07-171163 | 7/1995 |
| JP | 7-255735 A | 10/1995 |
| JP | H7-285089 A | 10/1995 |
| JP | 8-33641 A | 2/1996 |
| JP | 8-33642 A | 2/1996 |
| JP | 8-164141 A | 6/1996 |
| JP | H08-182684 A | 7/1996 |
| JP | H08-507708 A | 8/1996 |
| JP | 8229050 A | 9/1996 |
| JP | H8-336540 A | 12/1996 |
| JP | H08-336544 A | 12/1996 |
| JP | H09-501577 A | 2/1997 |
| JP | H09-164144 A | 6/1997 |
| JP | H10-113352 A | 5/1998 |
| JP | H10-118090 A | 5/1998 |
| JP | H10-512469 A | 12/1998 |
| JP | 2000-14632 A | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-204801 A | 7/2002 |
| JP | 2002-528161 A | 9/2002 |
| JP | 2002-314298 A | 10/2002 |
| JP | 2002369820 A | 12/2002 |
| JP | 2003-500153 A | 1/2003 |
| JP | 2003000603 A | 1/2003 |
| JP | 2003-504104 A | 2/2003 |
| JP | 2003-135473 A | 5/2003 |
| JP | 2003-148903 A | 5/2003 |
| JP | 2003-164066 | 6/2003 |
| JP | 2003-521301 A | 7/2003 |
| JP | 2003-523251 A | 8/2003 |
| JP | 2003-523254 A | 8/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344662 A | 12/2004 |
| JP | 2004-344663 | 12/2004 |
| JP | 2005-028147 A | 2/2005 |
| JP | 2005-28148 | 2/2005 |
| JP | 2005-028149 | 2/2005 |
| JP | 2005-505309 | 2/2005 |
| JP | 2005-505334 | 2/2005 |
| JP | 2005505322 | 2/2005 |
| JP | 2005-80702 | 3/2005 |
| JP | 2005-103280 | 4/2005 |
| JP | 2005-103281 | 4/2005 |
| JP | 2005-511131 | 4/2005 |
| JP | 2005-511137 | 4/2005 |
| JP | 2005103293 | 4/2005 |
| JP | 2005131163 | 5/2005 |
| JP | 2005131164 | 5/2005 |
| JP | 2005131173 | 5/2005 |
| JP | 2005131211 | 5/2005 |
| JP | 2005131212 | 5/2005 |
| JP | 2005-137919 | 6/2005 |
| JP | 2005-144183 | 6/2005 |
| JP | 2005-516714 | 6/2005 |
| JP | 2005137423 | 6/2005 |
| JP | 2005152416 | 6/2005 |
| JP | 2005-521109 | 7/2005 |
| JP | 2005-523105 | 8/2005 |
| JP | 4461008 B2 | 8/2005 |
| JP | 2005524474 | 8/2005 |
| JP | 2005-296412 | 10/2005 |
| JP | 2005-328882 | 12/2005 |
| JP | 2005-335432 | 12/2005 |
| JP | 2005-342267 | 12/2005 |
| JP | 2006-034975 | 2/2006 |
| JP | 2006-34977 | 2/2006 |
| JP | 2006-034978 | 2/2006 |
| JP | 2006-034980 | 2/2006 |
| JP | 2006-506106 | 2/2006 |
| JP | 2006-510879 | 3/2006 |
| JP | 2006-187649 | 7/2006 |
| JP | 2006-218297 | 8/2006 |
| JP | 2006-223872 | 8/2006 |
| JP | 2006-281405 | 10/2006 |
| JP | 2006-289064 | 10/2006 |
| JP | 2006-334412 | 12/2006 |
| JP | 2006-334417 | 12/2006 |
| JP | 2006-346445 | 12/2006 |
| JP | 2007-050253 | 3/2007 |
| JP | 2007-61628 | 3/2007 |
| JP | 2007-083051 | 4/2007 |
| JP | 2007-098130 | 4/2007 |
| JP | 2007-105481 | 4/2007 |
| JP | 3906843 B2 | 4/2007 |
| JP | 2007-117725 | 5/2007 |
| JP | 2007-130471 | 5/2007 |
| JP | 2007-222615 | 6/2007 |
| JP | 3934161 B2 | 6/2007 |
| JP | 2007-203049 | 8/2007 |
| JP | 2007-203051 | 8/2007 |
| JP | 2007-203057 | 8/2007 |

(56) References Cited

FOREIGN PATENT DOCUMENTS

| | | |
|---|---|---|
| JP | 2007-209751 A | 8/2007 |
| JP | 2007-524435 | 8/2007 |
| JP | 2007-229448 | 9/2007 |
| JP | 4001860 B2 | 10/2007 |
| JP | 2007-325922 | 12/2007 |
| JP | 2008-68073 A | 3/2008 |
| JP | 2008-206967 | 9/2008 |
| JP | 2008-212637 | 9/2008 |
| JP | 2008-212638 | 9/2008 |
| JP | 2008-220956 | 9/2008 |
| JP | 2008-259860 A | 10/2008 |
| JP | 2008-264535 A | 11/2008 |
| JP | 2008-283459 A | 11/2008 |
| JP | 2009-502351 A | 1/2009 |
| JP | 2009-506799 A | 2/2009 |
| JP | 2009-507526 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189837 A | 8/2009 |
| JP | 2009-189838 A | 8/2009 |
| JP | 2009-536082 A | 10/2009 |
| JP | 2009-261944 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |
| JP | 2010-504846 A | 2/2010 |
| JP | 2010-505524 A | 2/2010 |
| JP | 2010-069310 A | 4/2010 |
| JP | 2010-088876 A | 4/2010 |
| JP | 2010-098844 A | 4/2010 |
| JP | 4549018 B2 | 9/2010 |
| JP | 2010-540192 A | 12/2010 |
| JP | 4783373 B2 | 7/2011 |
| JP | 5140421 B2 | 2/2013 |
| JP | 5162595 B2 | 3/2013 |
| JP | 2013-128791 A | 7/2013 |
| JP | 5333899 B2 | 11/2013 |
| KR | 20110003229 A | 1/2011 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1333319 A2 | 8/1987 |
| SU | 1022703 A1 | 2/1988 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |

(56) References Cited

FOREIGN PATENT DOCUMENTS

| | | |
|---|---|---|
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/010482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 2003/079909 A3 | 3/2003 |
| WO | WO 03/030743 A2 | 4/2003 |
| WO | WO 03/037193 A1 | 5/2003 |
| WO | WO 2003/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 2003/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 2003/094746 A1 | 11/2003 |
| WO | WO 2003/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A2 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/049852 A2 | 5/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/059233 A2 | 5/2007 |
| WO | WO 2007/074430 A1 | 7/2007 |
| WO | WO 2007/089603 A2 | 8/2007 |
| WO | WO 2007/098220 A2 | 8/2007 |

(56) References Cited

FOREIGN PATENT DOCUMENTS

| | | |
|---|---|---|
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109125 A1 | 9/2008 |
| WO | WO 2008/124748 A1 | 10/2008 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2010/028332 A2 | 3/2010 |
| WO | WO 2010/030434 A1 | 3/2010 |
| WO | WO 2010/050771 A2 | 5/2010 |
| WO | WO 2010/054404 A1 | 5/2010 |
| WO | WO 2010/063795 A1 | 6/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/013103 A1 | 2/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/127462 A1 | 9/2012 |
| WO | WO 2012/143913 A2 | 10/2012 |
| WO | WO 201 2/1 601 6 | 11/2012 |
| WO | WO 2012/148667 A2 | 11/2012 |
| WO | WO 2012/148703 A2 | 11/2012 |
| WO | WO 2013/009699 A2 | 1/2013 |
| WO | WO 2013/036409 A1 | 3/2013 |
| WO | WO 2013/043707 A2 | 3/2013 |
| WO | WO 2013/043717 A1 | 3/2013 |
| WO | WO 2013/043721 A2 | 3/2013 |
| WO | WO 2013/062978 A2 | 5/2013 |
| WO | WO 2013/148762 A2 | 10/2013 |
| WO | WO 2013/167427 A1 | 11/2013 |
| WO | WO 2014/004199 A1 | 1/2014 |

OTHER PUBLICATIONS

International Search Report for PCT/US2012/028886, dated Nov. 23, 2012 (7 pages).

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/ abstract?CRETRY=1&SRETRY=0; [online] accessed: Sep. 22, 2008 (2 pages).

The Sodem Aseptic Battery Transfer Kit, Sodem Systems, (2000), 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print. cfm?ArticleID=17465, accessed Jan. 15, 2008 (5 pages).

Datasheet for Panasonic TK Relays Ultra Low Profile 2 a Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Black Reload with Tri-Staple™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Covidien Brochure, "Endo GIA™ Ultra Universal Stapler," (2010), 2 pages.

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Byrne et al., "Molecular Imprinting Within Hydrogels," Advanced Drug Delivery Reviews, 54 (2002) pp. 149-161.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 30-12.

Hoffman, "Hydrogels for Biomedical Applications," Advanced Drug Delivery Reviews, 54 (2002) pp. 30-12.

Peppas, "Physiologically Responsive Hydrogels," Journal of Bioactive and Compatible Polymers, vol. 6 (Jul. 1991) pp. 241-246.

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

Peppas, Editor "Hydrogels in Medicine and Pharmacy," vol. I, Fundamentals, CRC Press, 1986.

Matsuda, "Thermodynamics of Formation of Porous Polymeric Membrane from Solutions," Polymer Journal, vol. 23, No. 5, pp. 435-444 (1991).

(56) References Cited

OTHER PUBLICATIONS

Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
Http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
"Indian Standard: Automotive Vehicles—Brakes and Braking Systems (IS 11852-1:2001)", Mar. 1, 2001.

\* cited by examiner

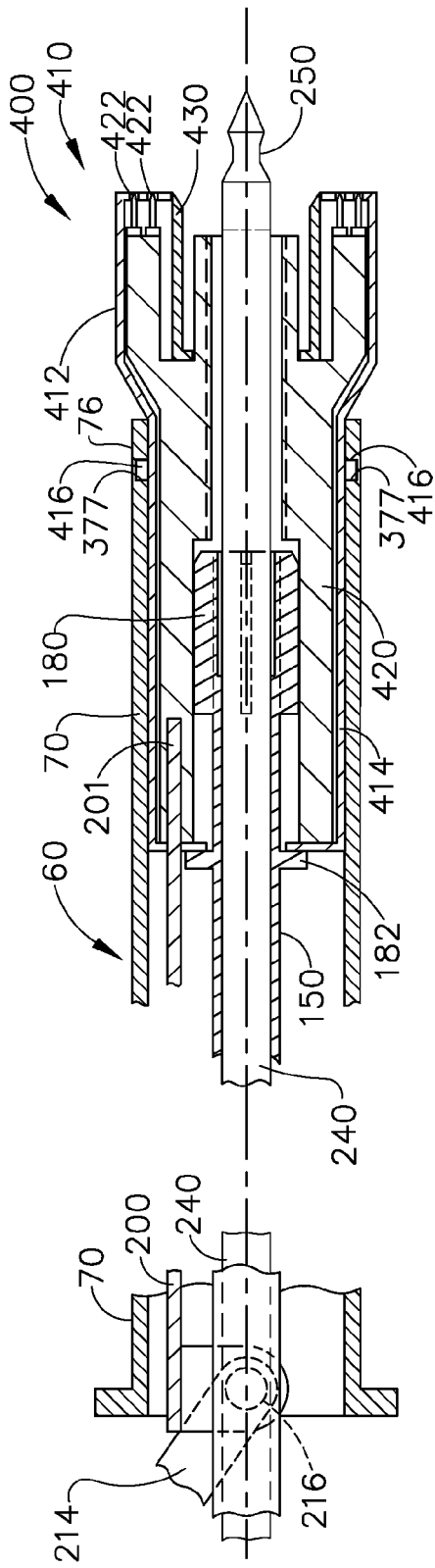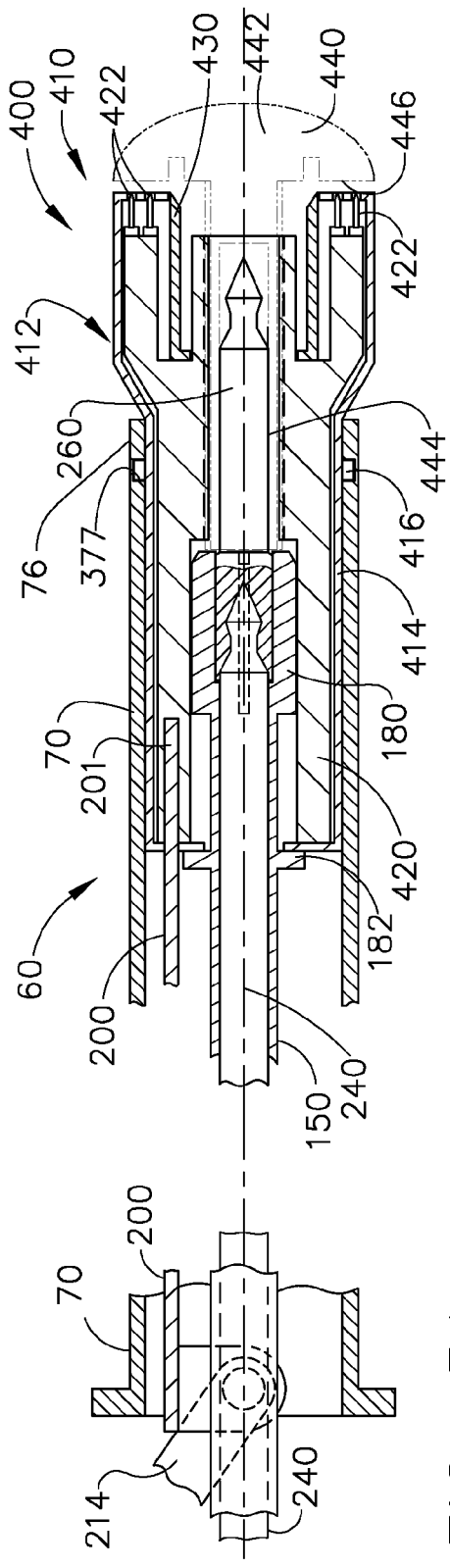

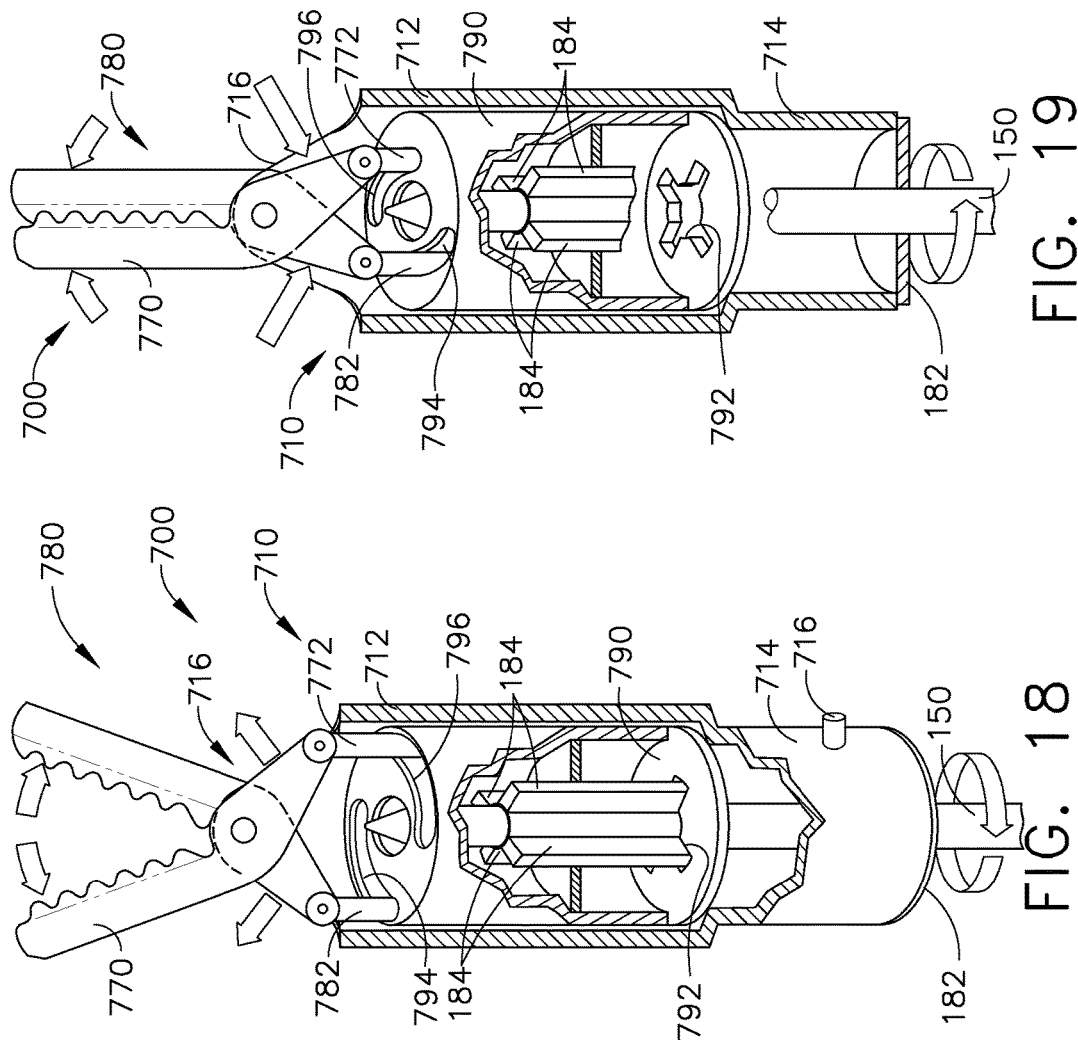

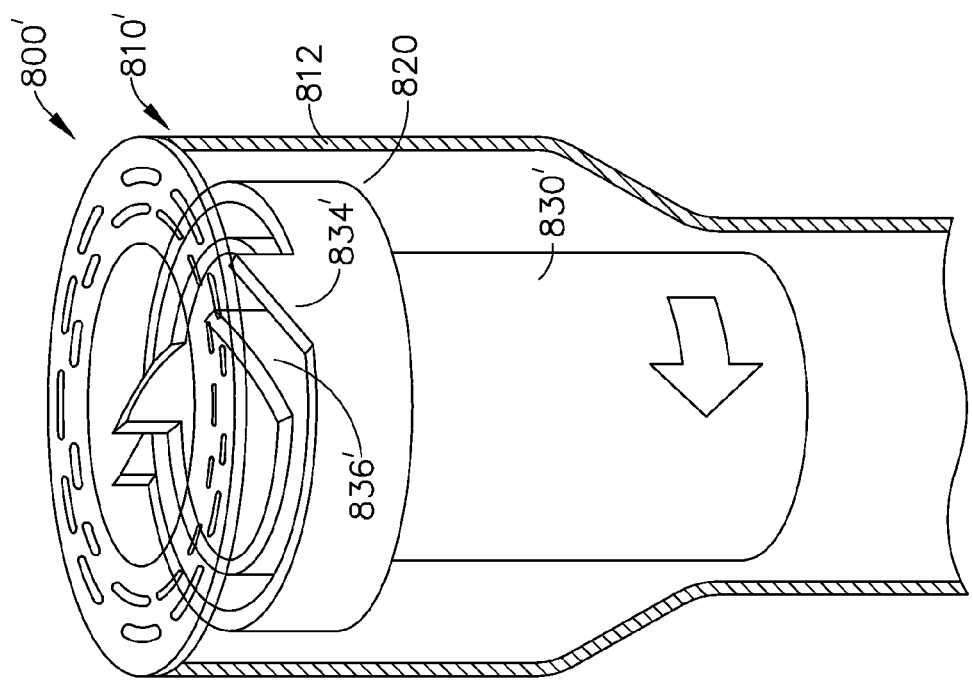
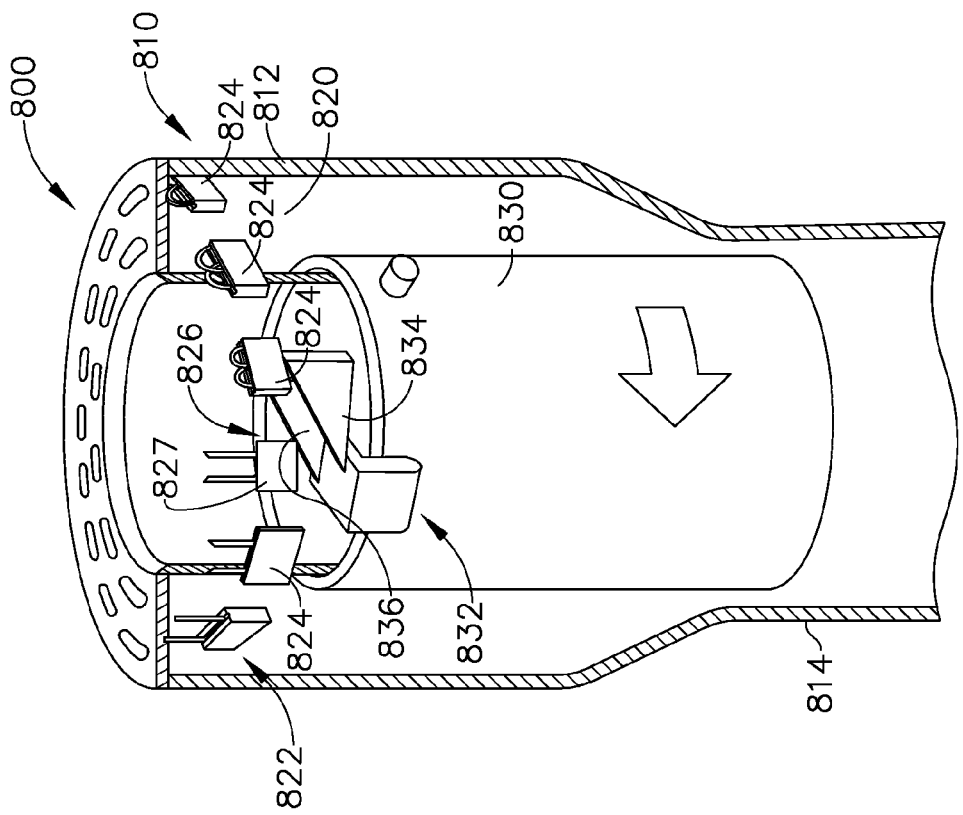

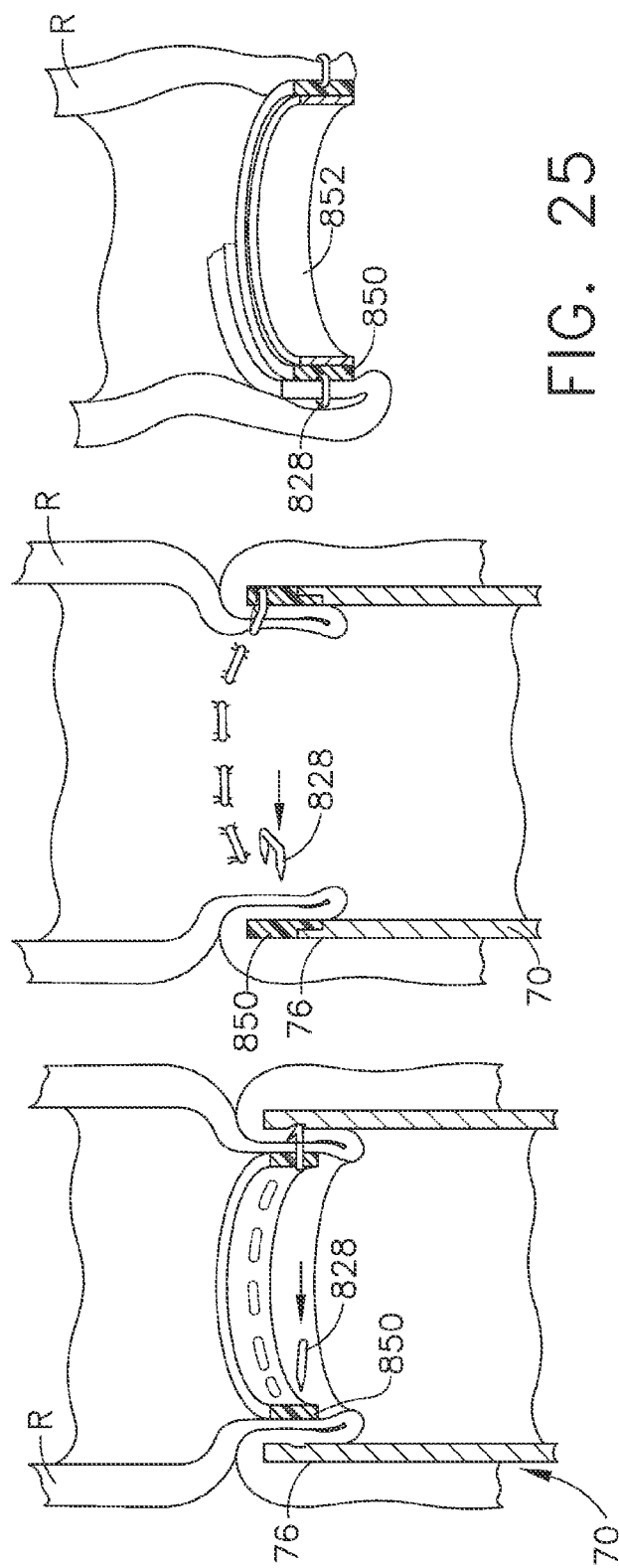

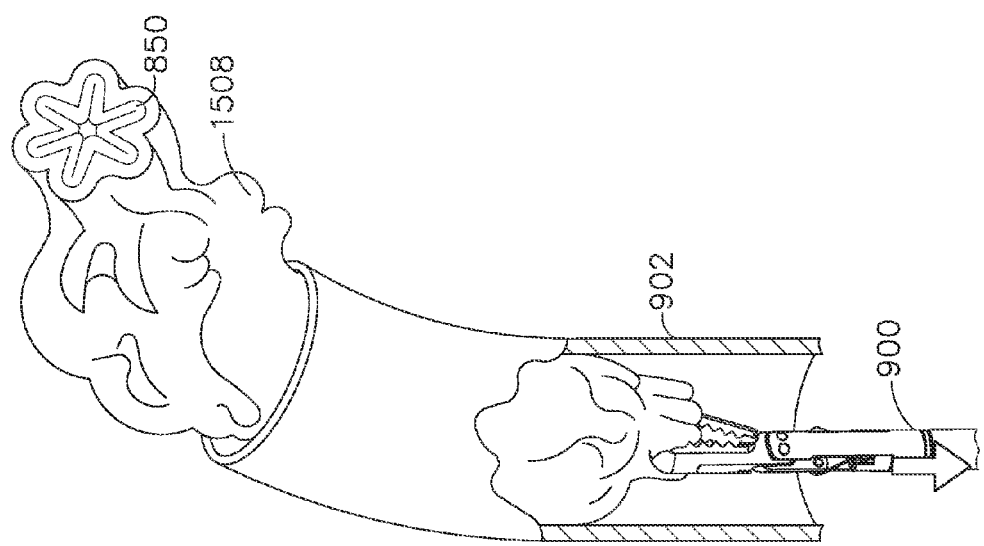
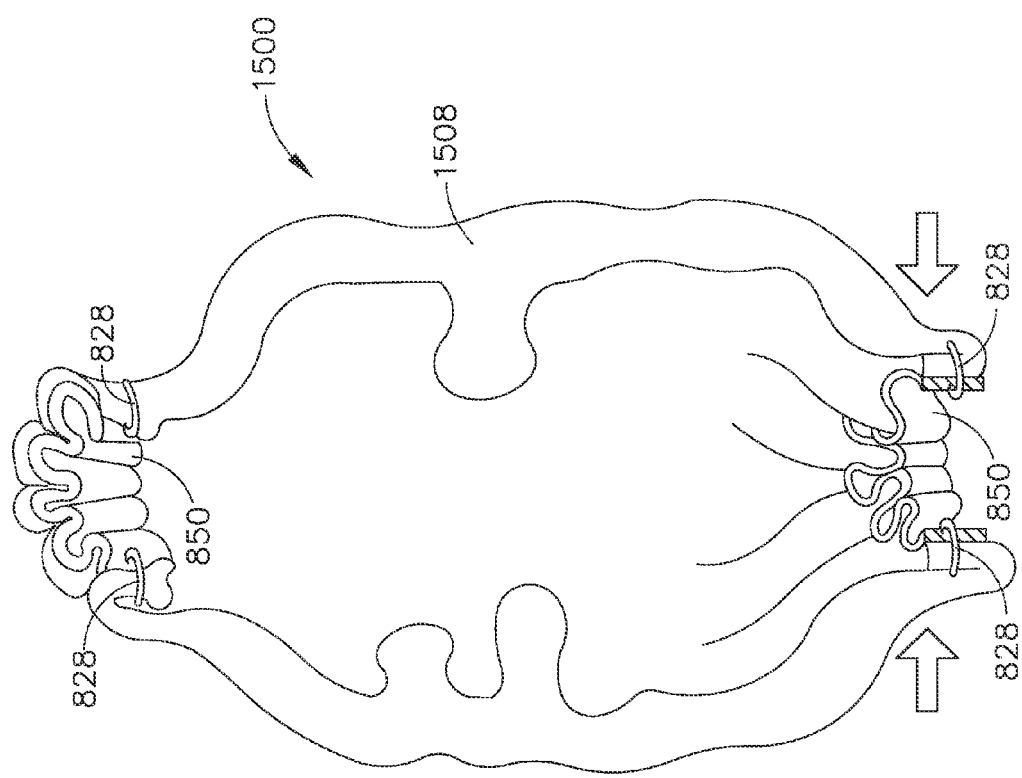

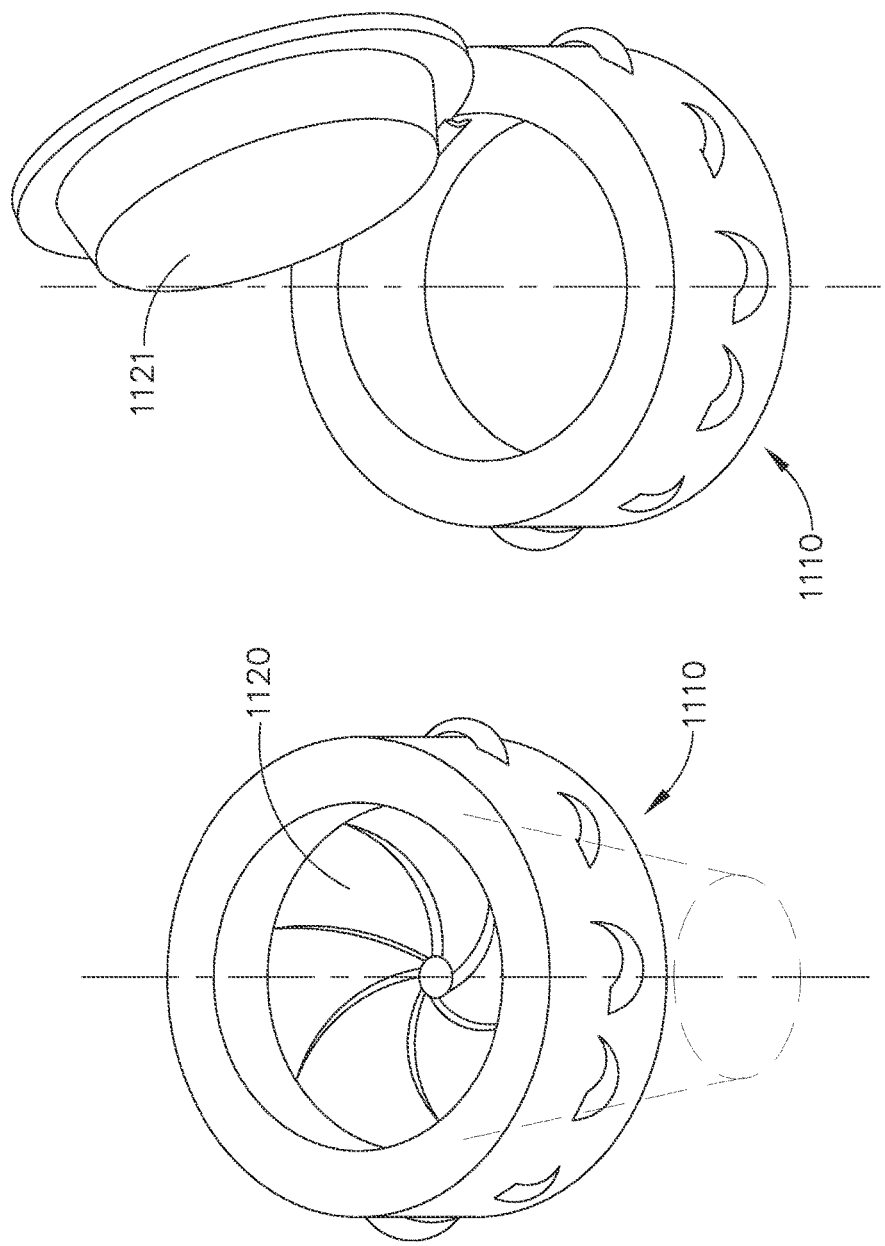

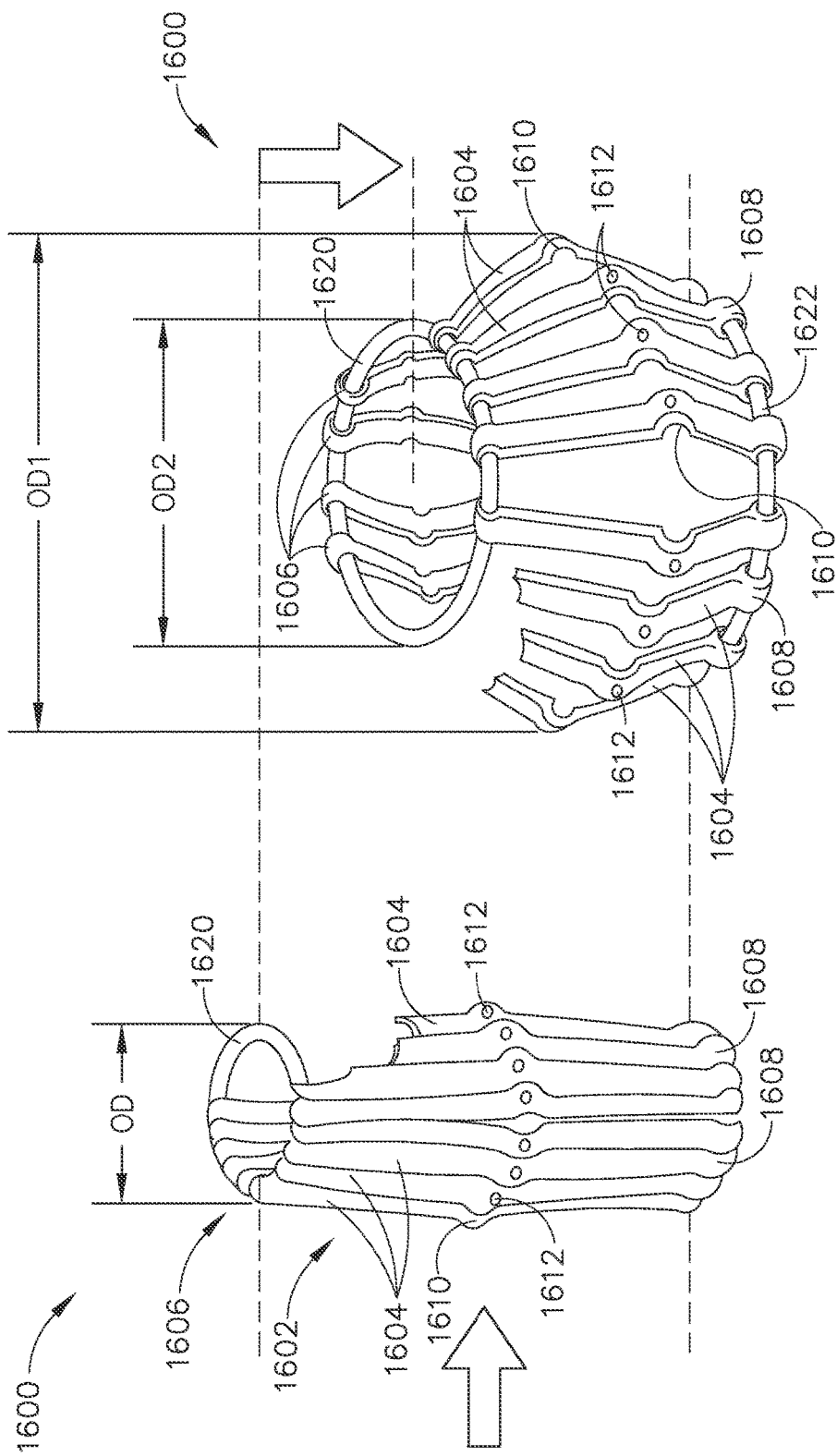

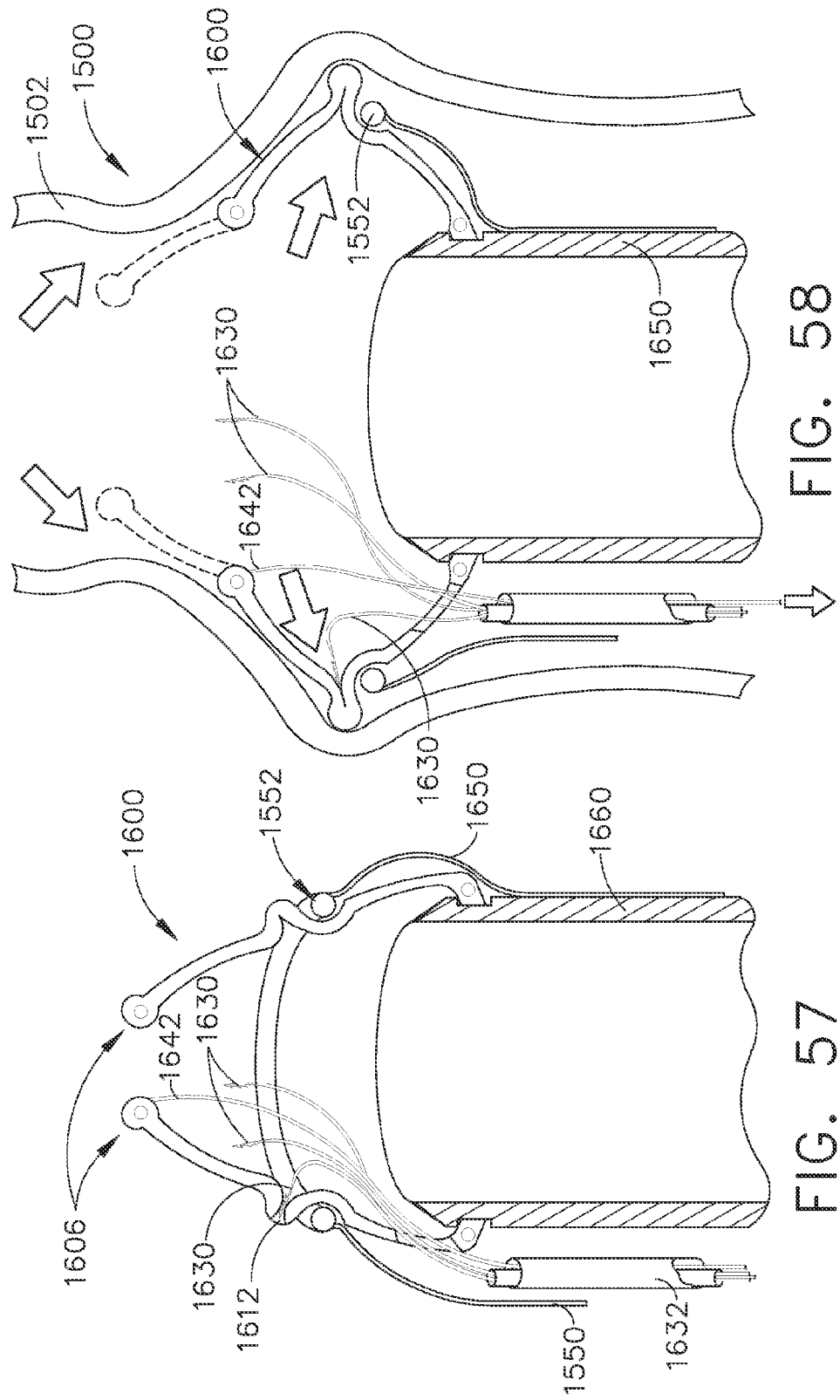

SURGICAL INSTRUMENT

CROSS-REFERENCE TO RELATED APPLICATIONS

This application is a continuation application claiming priority under 35 U.S.C. § 120 to U.S. patent application Ser. No. 13/181,798, entitled MODULAR SURGICAL TOOL SYSTEMS, filed Jul. 13, 2011, now U.S. Patent Application Publication No. 2012/0239010, which claims the benefit of and priority under 35 U.S.C. § 119(e) from U.S. Provisional Patent Application Ser. No. 61/452,432, filed Mar. 14, 2011, entitled SURGICAL STAPLING INSTRUMENTS, the entire disclosures of which are hereby incorporated by reference herein.

FIELD OF THE INVENTION

The present invention generally relates to surgical devices for performing a variety of surgical procedures, and more particularly, to a surgical tool system that comprises a single handle assembly that can be employed with different tool attachments that are capable of performing different surgical procedures and actions.

BACKGROUND

Circular instruments are used to perform a number of surgical procedures. Such procedures often require the use of several different circular instruments that have a desired diametric size, shaft length and shaft geometry. Hospitals require storage space to inventory multiple product codes to satisfy these procedures.

One type of circular instrument that is often used in open and laparoscopic approaches is a circular stapling instrument. In general, a conventional circular stapler typically consists of an elongated shaft that has a proximal actuating mechanism and a distal stapling mechanism mounted to the elongated shaft. Various circular stapling devices are disclosed, for example, in U.S. Pat. Nos. 5,104,025; 5,205,459; 5,285,945; and 5,309,927 which are each herein incorporated by reference in their respective entireties. The distal stapling mechanism commonly consists of a fixed stapling cartridge that contains a plurality of staples configured in a concentric circular array. A round cutting knife is concentrically mounted in the cartridge interior for axial travel therein. Extending axially from the center of the cartridge is a movable trocar or attachment shaft that is adapted to have a staple anvil removably coupled thereto. The anvil is configured to form the ends of the staples as they are driven into it. The distance between a distal face of the staple cartridge and the staple anvil is commonly controlled by an adjustment mechanism that is mounted to the proximal end of the stapler shaft for controlling the axial movement of the trocar. Tissue that is clamped between the staple cartridge and the staple anvil is simultaneously stapled and cut when the actuating mechanism is activated by the surgeon.

Such circular stapling instruments are essential for creating anastomosis within the body when using open or laparoscopic methods. However, such instruments cannot perform other actions or procedures that may also be required to complete a particular operation. Such actions may comprise, for example, grasping and manipulating tissue, cutting tissue without deploying fasteners, dilating colon tissue, safely managing the removal of the transected specimens from the colon, etc. Thus, different types and sizes of instruments must be kept on hand.

Thus, the need exists for a surgical tool system that includes a single handle assembly that can be employed with different tool attachments that are capable of performing different surgical procedures and actions.

There is a further need for a universal port arrangement that can be used to dilate and/or occlude the colon and facilitate the entry and removal of surgical instruments within the colon;

There is a further need for a universal port arrangement that may be selectively employed to sever colon tissue.

Yet another need exists for a universal port arrangement that can facilitate the safe removal of transected colon portions.

The foregoing discussion is intended only to illustrate some of the shortcomings present in the field of the invention at the time, and should not be taken as a disavowal of claim scope.

BRIEF SUMMARY

A surgical instrument is disclosed comprising an actuation system, a drive system coupled to the actuation system, and a tool head coupled to the drive system. The drive system comprises a rotatable shaft which defines a longitudinal axis and an outer casing surrounding the rotatable shaft. The tool head comprises an annular cartridge comprising a plurality of staples and a pliable bunchable ring surrounding the annular cartridge. The surgical instrument is configured to drive the staples through the pliable bunchable ring in a direction which is transverse to the longitudinal axis. The outer casing is configured to deform the staples driven through the pliable bunchable ring.

A surgical instrument is disclosed comprising a pliable bunchable ring and a stapler head surrounded by the pliable bunchable ring. The stapler head comprises a plurality of radial openings, a plurality of staples, and an actuatable drive assembly. The actuatable drive assembly is configured to drive the staples through the openings and through the pliable bunchable ring as the actuatable drive assembly is actuated. The actuatable drive assembly comprises a rotatable driver configured to rotate within the stapler head.

An end effector of a surgical instrument for fastening a lumen is disclosed. The end effector comprises an annular cartridge body, an annular row of fasteners removably stored in the annular cartridge body, an actuatable drive assembly comprising a rotatable driver configured to rotate within the end effector, and a cinching member extending around the annular cartridge body. The fasteners implant the cinching member to the lumen when the fasteners are ejected from the annular cartridge body.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the various forms of the present invention.

FIG. 5 is a cross-sectional view of the shaft assembly and surgical tool head depicted in FIGS. 2 and 4;

FIG. 5A is another cross-sectional view of the shaft assembly and surgical tool head depicted in FIG. 5 with an anvil (shown in phantom lines) attached thereto;

FIG. 18 is a partial cross-sectional view of another surgical tool head embodiment of the present invention with the movable jaws thereof in an open position;

FIG. 19 is another partial cross-sectional view of the surgical tool head embodiment of FIG. 18 with the movable jaws thereof in a closed position;

FIG. 20 is a partial top view of a rotary adapter employed in the surgical tool head of FIGS. 18 and 19;

FIG. 21 is a partial cross-sectional view of another surgical tool head embodiment of the present invention with various component portions thereof omitted for clarity;

FIG. 22 is a partial cross-sectional view of another surgical tool head embodiment of the present invention with various component portions thereof omitted for clarity;

FIG. 23 is a partial cross-sectional view of a modular surgical instrument embodiment wherein the surgical staples have been driven horizontally through an elastic ring supported within the colon;

FIG. 24 is another partial cross-sectional view of a modular surgical instrument embodiment wherein the surgical staples have been driven horizontally through an elastic ring supported on the distal end of a shaft assembly;

FIG. 25 is another partial cross-sectional view illustrating surgical staples that have been driven horizontally through an elastic ring supported within the colon with a metal ring removably inserted into the interior of the elastic ring to prevent the elastic ring from collapsing;

FIG. 26 illustrates a colon portion wherein the elastic rings disclosed in FIGS. 23-25 have been attached to the ends of the colon portion and are in a collapsed state;

FIG. 27 is a partial cross-sectional perspective view of a severed portion of the colon being pulled through a tube inserted through the rectum;

FIG. 33A is a diagrammatical perspective view of the universal port embodiment of FIG. 33;

FIG. 33B is another diagrammatical perspective view of another universal port embodiment of the present invention;

FIG. 55 is a perspective view of a portion of the port of FIG. 54 in a collapsed state;

FIG. 56 is another perspective view of the port of FIGS. 54 and 55 in an expanded state;

FIG. 57 is another partial cross-sectional view of the port and insertion tube embodiments of FIG. 54;

FIG. 58 is another partial cross-sectional view of the port and insertion tube of FIG. 57 inserted into a portion of the colon and illustrating deployment of the tissue retaining barbs into the colon;

FIG. 68 is a partial perspective view of another tissue manipulation device embodiment of the present invention inserted into the colon.

DETAILED DESCRIPTION

Figure 1:
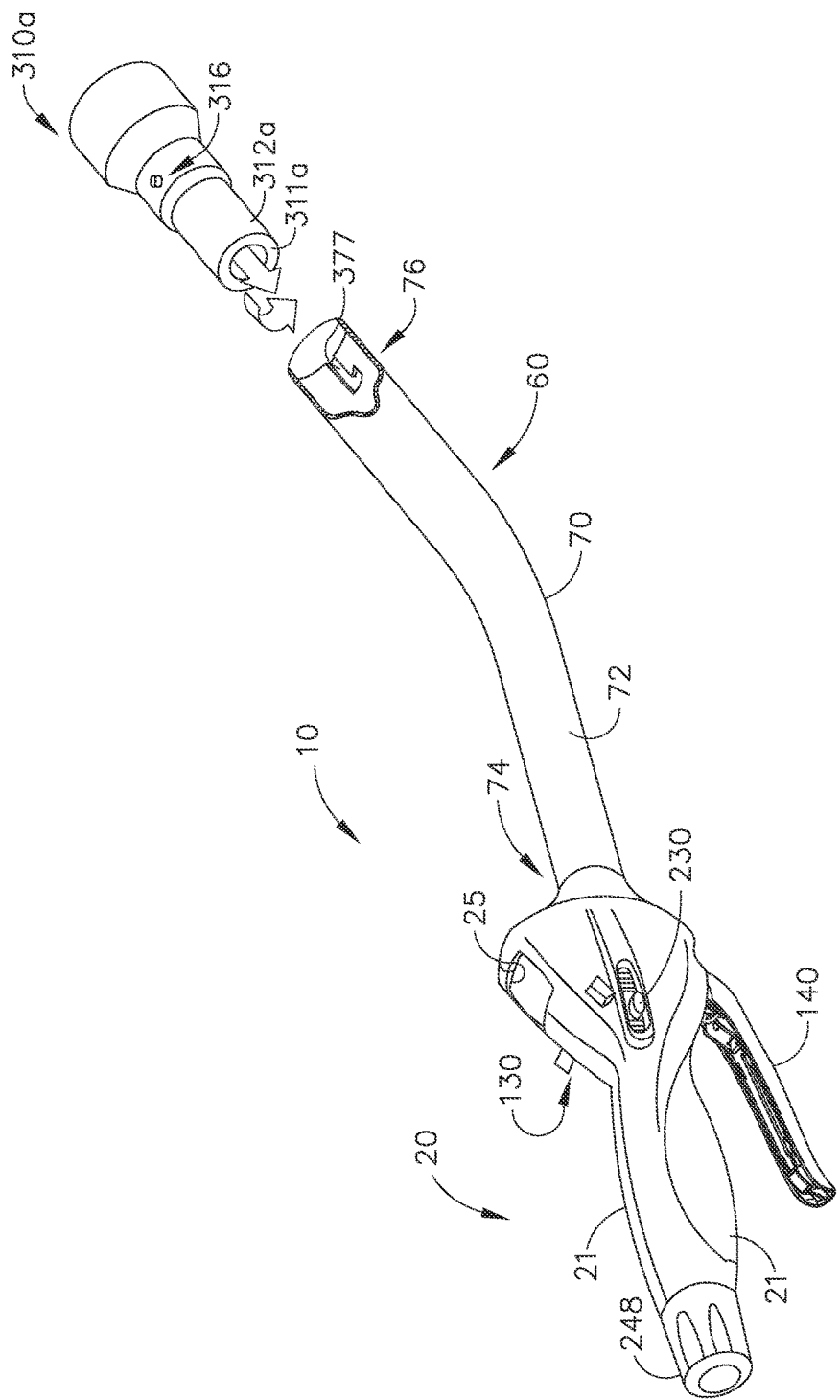
FIG. 1 is an exploded perspective view of one form of a modular surgical instrument of an embodiment of the present invention and a surgical tool head embodiment of the present invention.

The assignee of the present application also owns the following applications which were filed on Jul. 13, 2011, and which are each herein incorporated by reference in their respective entireties:

U.S. patent application Ser. No. 13/181,779, entitled MULTIPLE PART ANVIL ASSEMBLIES FOR CIRCULAR SURGICAL STAPLING DEVICES, now U.S. Patent Application Publication No. 2012/0234892;

U.S. patent application Ser. No. 13/181,801, entitled SPECIMEN RETRACTION DEVICES AND METHODS, now U.S. Pat. No. 8,632,462;

U.S. patent application Ser. No. 13/181,807, entitled MODULAR OCCLUSION AND TISSUE ACQUISITION MECHANISMS FOR CIRCULAR STAPLING DEVICES, now U.S. Pat. No. 8,827,903;

U.S. patent application Ser. No. 13/181,831, entitled TISSUE MANIPULATION DEVICES, now U.S. Pat. No. 8,858,590;

U.S. patent application Ser. No. 13/181,768, entitled COLLAPSIBLE ANVIL PLATE ASSEMBLIES FOR CIRCULAR SURGICAL STAPLING DEVICES, now U.S. Patent Application Publication No. 2012/0234890;

U.S. patent application Ser. No. 13/181,786, entitled CIRCULAR STAPLING DEVICES WITH TISSUE-PUNCTURING ANVIL FEATURES, now U.S. Patent Application Publication No. 2012/0234898;

U.S. patent application Ser. No. 13/181,774, entitled ANVIL ASSEMBLIES WITH COLLAPSIBLE FRAMES FOR CIRCULAR STAPLERS, now U.S. Pat. No. 8,978,955;

U.S. patent application Ser. No. 13/181,842, entitled RECTAL MANIPULATION DEVICES, now U.S. Pat. No. 8,734,478;

U.S. patent application Ser. No. 13/181,836, entitled SURGICAL ACCESS DEVICES WITH ANVIL INTRODUCTION AND SPECIMEN RETRIEVAL STRUCTURES, now U.S. Patent Application Publication No. 2012/0238823; and U.S. patent application Ser. No. 13/181,827, entitled SURGICAL BOWEL RETRACTOR DEVICES, now U.S. Patent Application Publication No. 2012/0238824.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

FIG. 1 illustrates one form of a modular surgical instrument 10 of an embodiment of the present invention. In at least one embodiment, the modular surgical instrument 10 includes a universal actuator handle assembly 20 that is attached to an elongated shaft assembly 60 that is configured for operable attachment to a variety of different surgical tool heads. FIG. 1 illustrates a circular stapling head 310a, the attachment and operation of which will be discussed in further detail below. In the depicted embodiment, the handle assembly 20 operably supports an actuation system generally designated as 100 which is configured to selectively apply various forms of actuation motions to the particular-type of surgical tool head attached thereto. As the present Detailed Description proceeds, those of ordinary skill in the art will appreciate that portions of the various modular surgical instruments disclosed herein may be configured to operably interface with a robotic control system that can provide the requisite actuation motions to the instruments.

In various embodiments, the handle assembly 20 includes two handle case segments 21 that may be interconnected together by suitable fastener arrangements for ease of assembly. The shaft assembly 60 includes an outer shaft casing 70 that is substantially hollow and may be fabricated from two casing segments 72 that are coupled together to form a hollow conduit. The outer shaft casing 70 has a proximal end 74 that is coupled to the handle assembly 20 and an open distal end 76.

The Rotary Drive System

Figure 2:
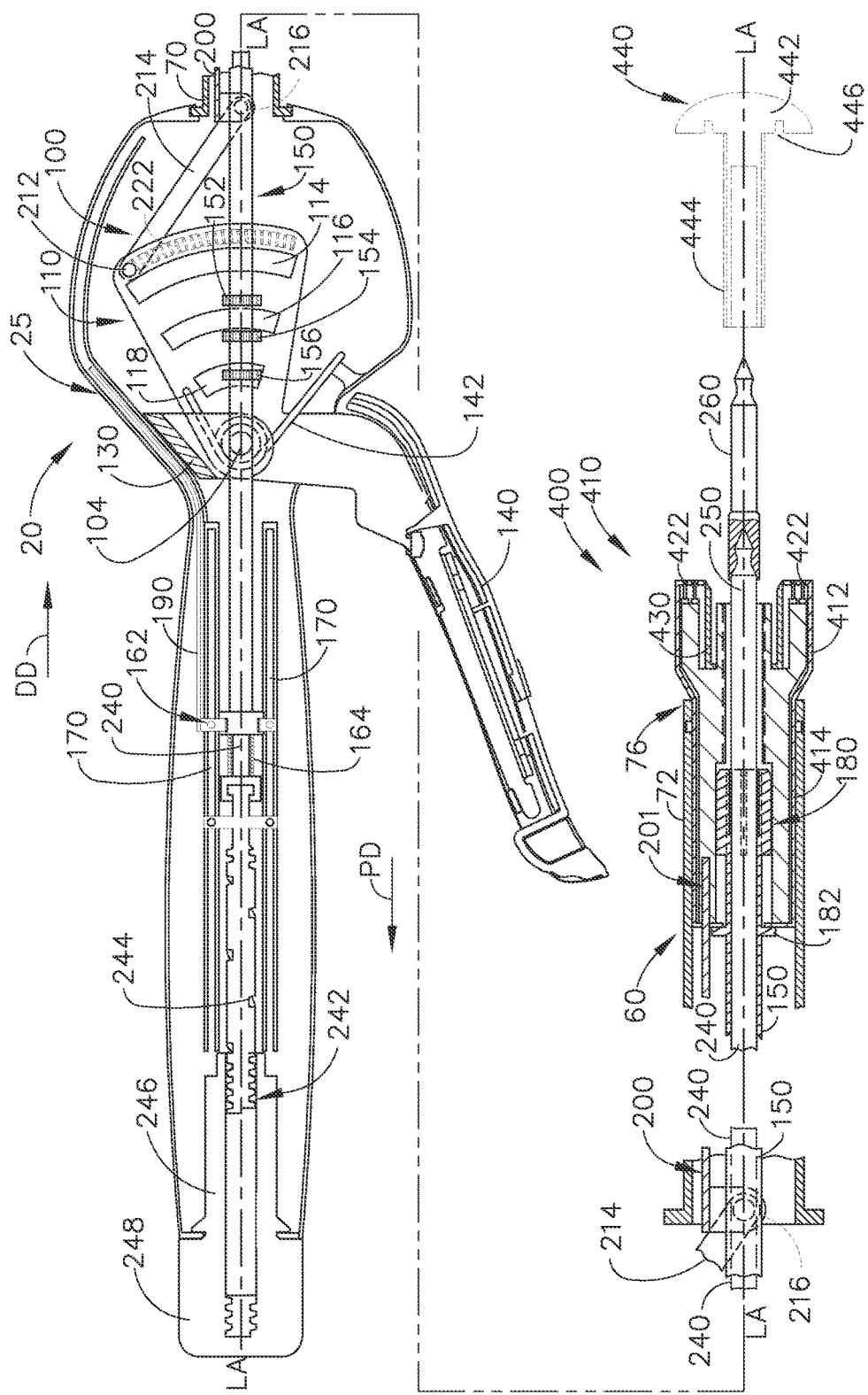
FIG. 2 is a cross-sectional view of one form of a modular surgical instrument embodiment of the present invention attached to a surgical tool head embodiment of the present invention.
Figure 3:
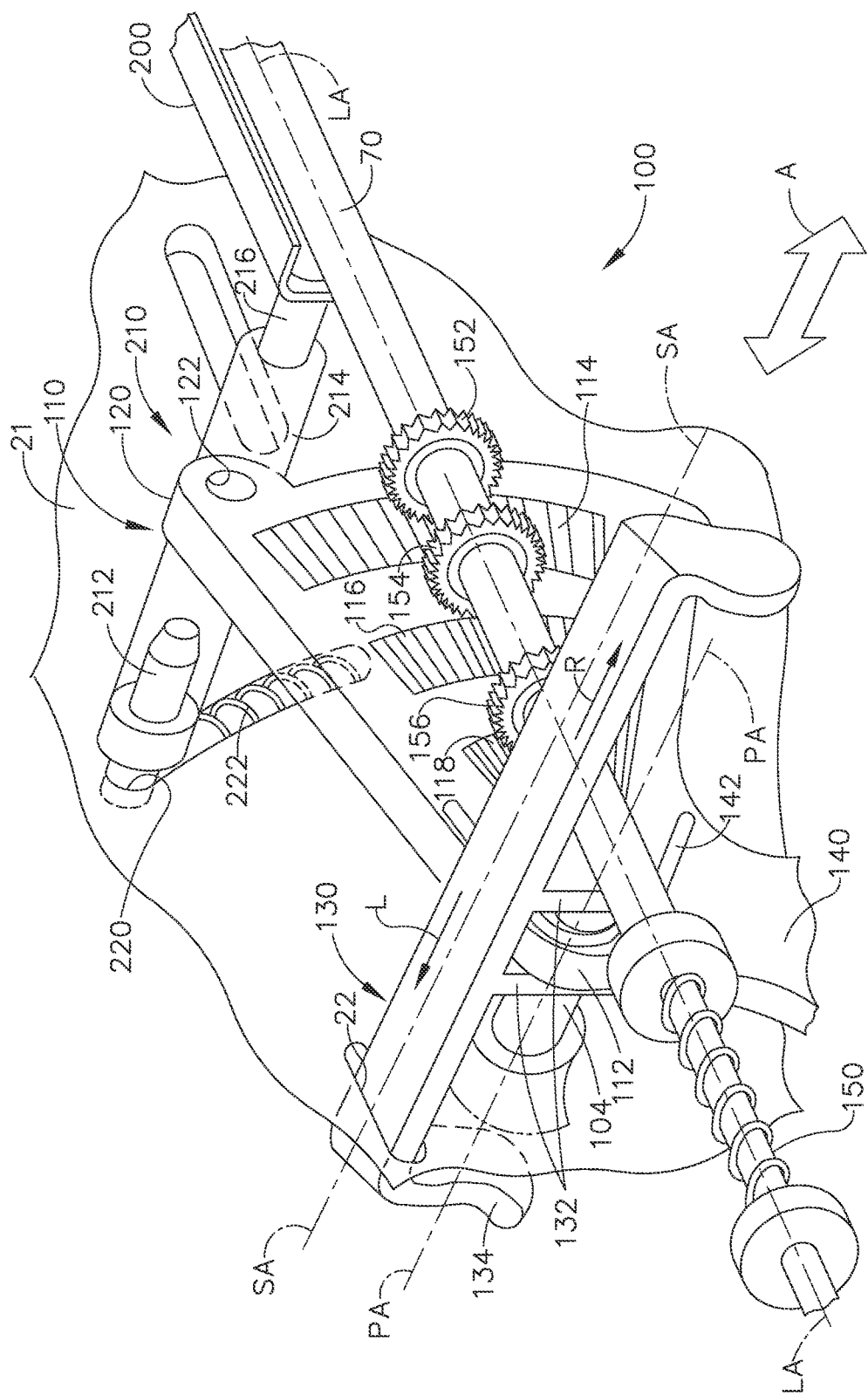
FIG. 3 is a partial perspective view of one embodiment of an actuation system of a modular surgical instrument embodiment of the present invention.

Various embodiments of the modular surgical instrument 10 include a unique and novel transmission or actuation system that facilitates the selective application of a variety of different axial and rotary motions to a particular surgical tool head attached thereto. Referring to FIGS. 2 and 3, one form of actuation system 100 includes a gear plate 110 that is pivotally supported in the handle assembly 20 for selective pivotal travel about a pivot axis PA-PA that is substantially transverse to the instrument's longitudinal axis LA-LA. The gear plate 110 may be pivotally supported within the handle assembly 20 on a pivot shaft 104 that extends between the handle case segments 21. As will be discussed in further detail below, the gear plate 110 is also laterally movable on the pivot shaft 104 from a first rotary drive position to a second axial drive position by a first drive selector switch 130 that is slidably supported between the handle case segments 21. As can be seen in FIG. 3, the first drive selector switch 130 is provided with two downwardly protruding clevis arms 132 that are configured to receive a proximal end portion 112 of the gear plate 110 therebetween. The first drive selector switch 130 extends through slots 22 in the handle case members 21 and have down turned end portions 134 to enable the user to slide the first drive selector switch 130 laterally back and forth (arrow "A" in FIG. 3) within the handle assembly 20 along a selector axis SA-SA that is substantially transverse to the longitudinal axis LA-LA. An "actuator" in the form of a firing trigger 140 is attached to, or otherwise integrally formed with, the gear plate 110 such that the gear plate 110 may be selectively pivoted about the pivot axis PA-PA by squeezing the firing trigger 140 toward the handle assembly 20. The term "actuator" may also encompass a portion of a robotic system configured to apply the requisite actuation motion to the gear plate 110.

Figure 3A:
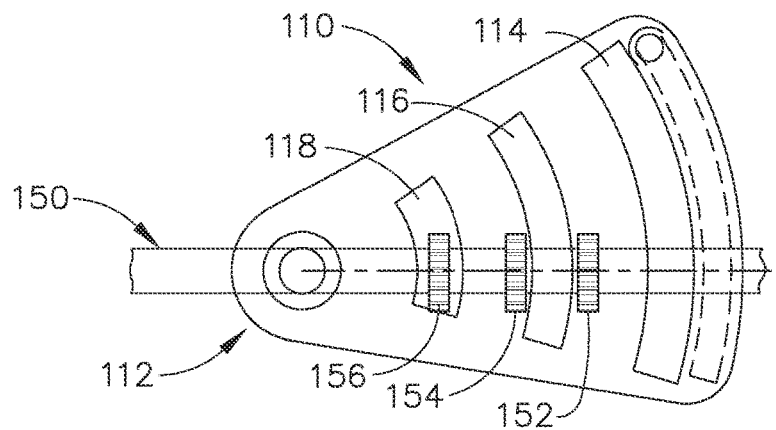
FIGS. 3A-3C are side views of a gear plate embodiment and rotary drive shaft embodiment of the present invention.
Figure 3B:
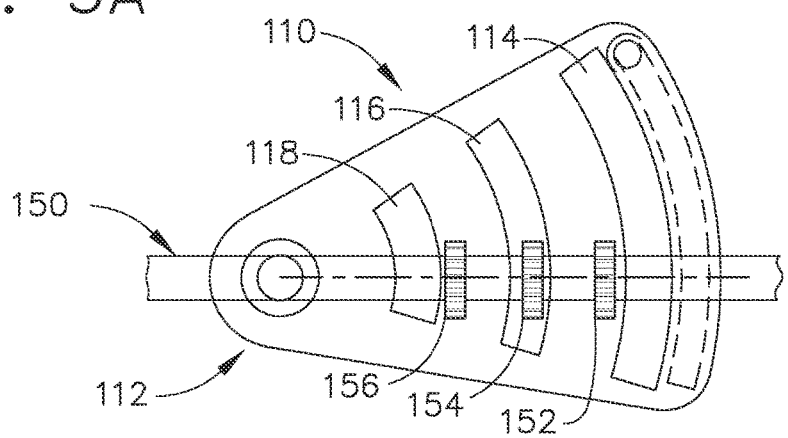
Figure 3C:
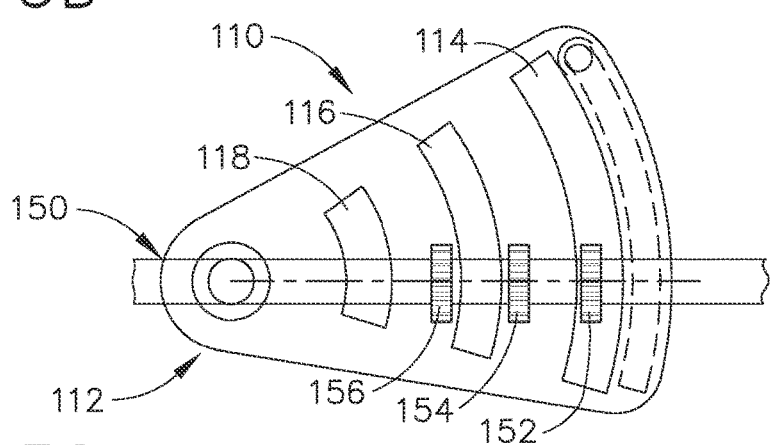

As can be further seen in FIG. 2, the gear plate 110 is configured to operably interact with a rotary drive shaft 150 that extends through the outer shaft casing 70 of the elongated shaft assembly 60 and is rotatably supported therein. In various embodiments the gear plate 110 has a first gear rack 114, a second gear rack 116, and a third gear rack 118 formed thereon. See FIGS. 3A-3C. The rotary drive shaft 150 has a first pinion gear 152 that is adapted for selective meshing engagement with the first gear rack 114 and a second pinion gear 154 that is adapted for selective meshing engagement with the second gear rack 116 and a third pinion gear 156 that is adapted for selective meshing engagement with the third gear rack 118. As will become further apparent as the present Detailed Description proceeds, each gear rack 114, 116, 118 defines a discrete amount of rotary travel that may be applied to the rotary drive shaft 150. For example, the first gear rack 114, when in meshing engagement with the first pinion gear 152, may facilitate an application of a first amount of rotary travel to the rotary drive shaft 150 upon application of an actuation motion to the firing trigger 140. For example, the first gear rack 114 may facilitate a first amount of rotary travel of approximately 0.70" when the firing trigger 140 is pivoted from a starting position to an ending position. The second gear rack 116, when in meshing engagement with the second pinion gear 154, facilitates a second range of rotary travel to the rotary drive shaft 150. For example, the second gear rack 116 may facilitate a second amount of rotary travel of approximately 1.41" when the firing trigger 140 is pivoted from a starting position to an ending or fully depressed position. The third gear rack 118, when in meshing engagement with the third pinion gear 156, facilitates a third amount of rotary travel of approximately 2.11" when the firing trigger 140 is pivoted from a starting position to an ending or fully depressed position. It will be understood, however, that other numbers and lengths of gear rack and pinion gear arrangements could conceivably be employed to provide other ranges of rotary motion without departing from the spirit and scope of the present invention.

Also in various handle assembly embodiments, a torsion spring 142 is employed to bias the firing trigger 140 to the unactuated position shown in FIG. 1. Thus, in various embodiments, once the surgeon releases the firing trigger 140, the spring 142 returns the firing trigger 140 to the unactuated position and, in doing so, applies a reverse rotary motion to the rotary drive shaft 150. Various forms of known trigger safety arrangements such as those disclosed in U.S. Pat. No. 7,506,791, entitled SURGICAL STAPLING INSTRUMENT WITH MECHANICAL MECHANISM FOR LIMITING MAXIMUM TISSUE COMPRESSION, the disclosure of which is herein incorporated by reference in its entirety, may also be employed.

The rotary drive shaft 150 further has a proximal end 160 that is movably supported within the handle assembly for rotary and axial travel therein. In one embodiment, for example, the proximal end 160 of the rotary drive shaft 150 is configured to support a bearing assembly 162 thereon that is constrained to move in axial tracks 170 formed in the handle cases 21. See FIG. 2. The bearing assembly 162 facilitates rotation of the rotary drive shaft 150 about the longitudinal axis LA-LA while also facilitating its axial travel within the handle assembly 20 and the outer shaft casing 70 of the shaft assembly 60. As can be seen in FIG. 2, a compression spring 164 serves to axially bias the rotary drive shaft 150 in the distal direction "DD".

As can also be seen in FIGS. 2-6, the rotary drive shaft 150 is hollow and has a distal end portion 180 that is configured to operationally mate with various forms of surgical tool heads attached thereto. As will be discussed in further detail below, the distal end portion 180 has an actuator flange 182 formed thereon that is oriented for engagement by a proximal end of the particular surgical tool head or adapter arrangement coupled thereto. Thus, when a particular surgical tool head is coupled to the shaft assembly 60, its distal end contacts the actuator flange 182 to bias the rotary drive shaft 150 in the proximal direction.

Figure 4:
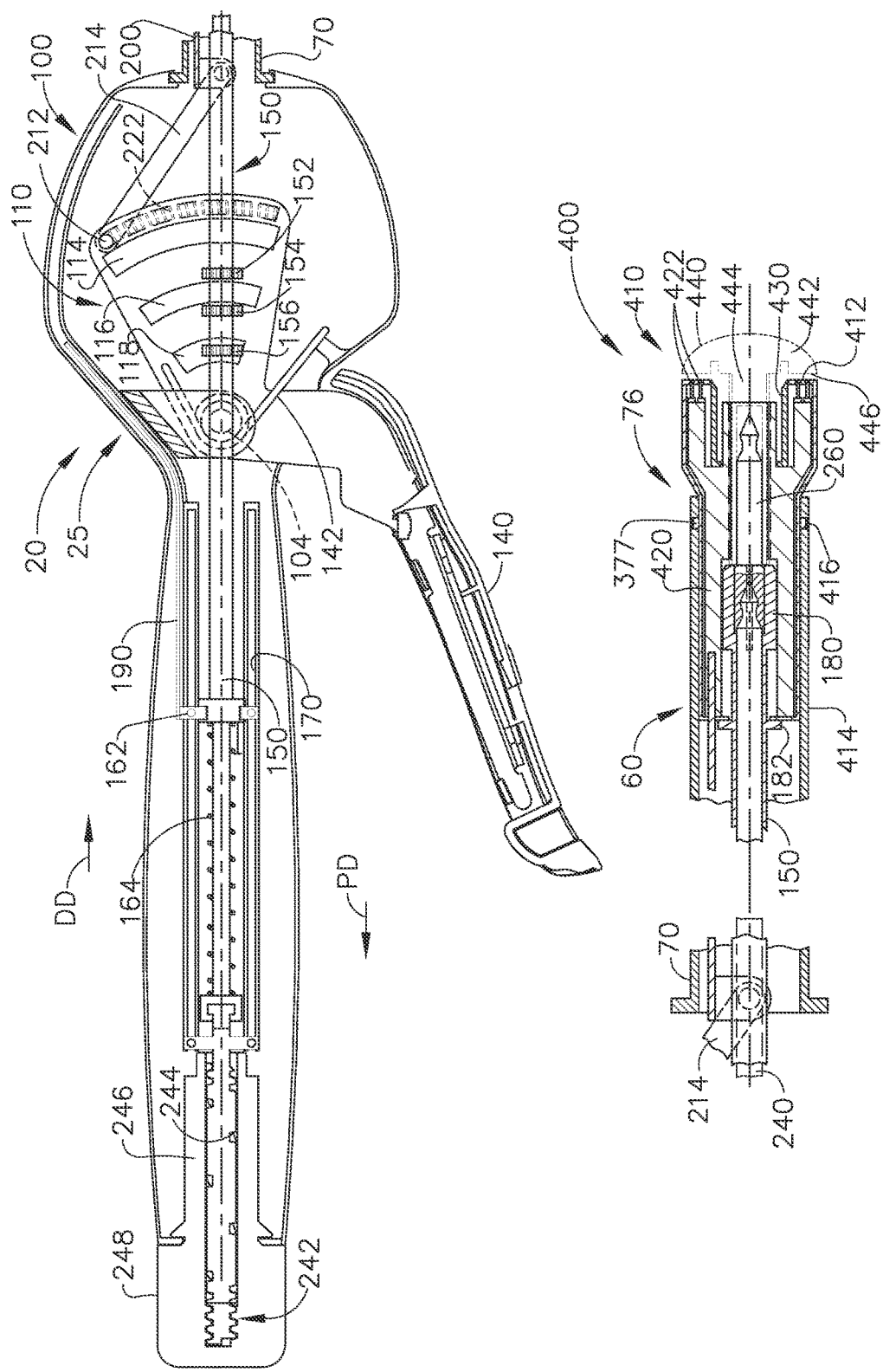
FIG. 4 is another cross-sectional view of the modular surgical instrument embodiment of and surgical tool head of FIG. 2 with an anvil (shown in phantom lines) attached thereto.
Figure 6:
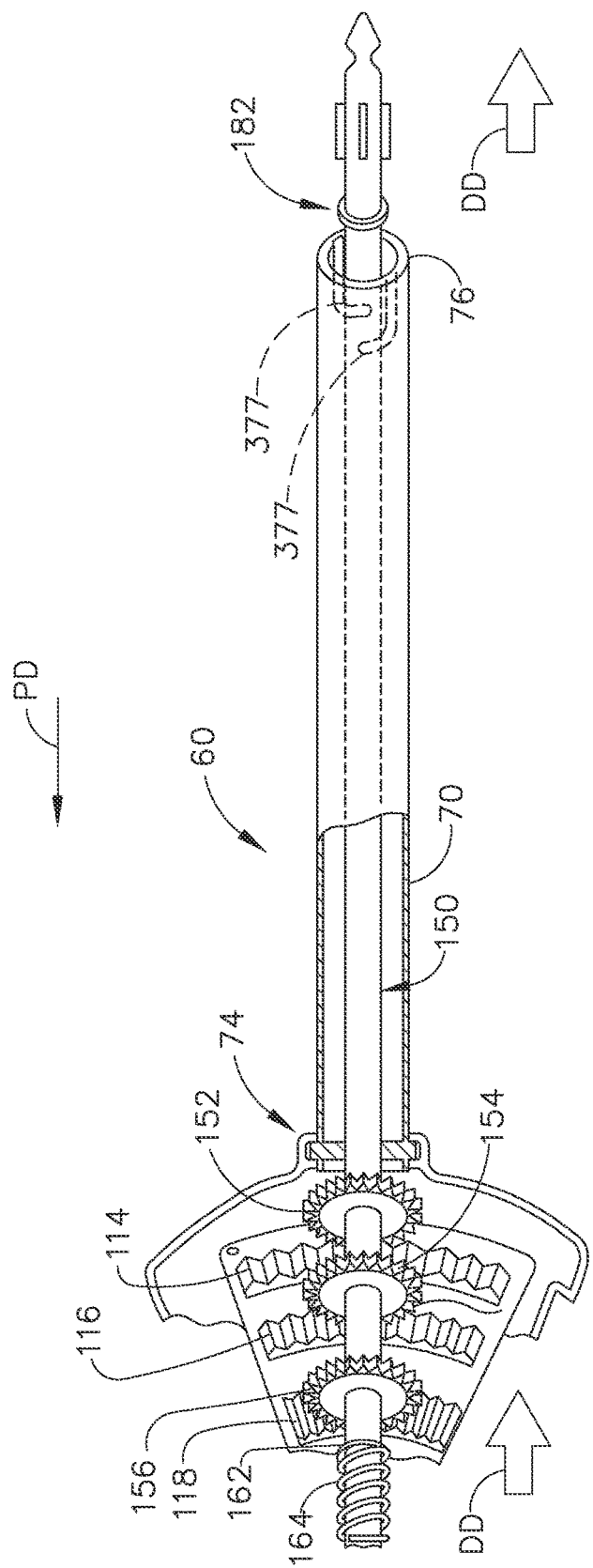
FIG. 6 is a partial cross-sectional view of the handle and shaft assembly of the modular surgical instrument of FIGS. 2 and 4.

Also in various embodiments, the handle assembly 20 may have a window or opening 25 therein (FIG. 1) that facilitates viewing by the surgeon of an indicator member 190. In various embodiments, the indicator member 190 may comprise a tape member that is flexible enough to axially travel back and forth within the handle assembly 20 and be viewable through the window or opening 25. The tape member 190 is attached to the bearing assembly 162 as can be seen in FIGS. 2 and 4 and has indication indicia thereon that corresponds to the gear rack 114, 116, 118 that is engaged with its corresponding pinion gear 152, 154, 156, respectively. For example, the indicator indicia may comprise a picture, drawing, diagram, model identification number, etc. of the particular surgical tool head that requires the corresponding amount of discrete rotary travel of the rotary drive shaft 150 for actuation purposes.

The Axial Drive Systems

The instrument 10 further includes axial drive arrangements for selectively applying axial actuation motions to the various surgical tool heads attached to the shaft assembly 60.

As was discussed above, a first drive selector switch 130 is configured to engage the proximal end portion 112 of the gear plate 110. Such arrangement permits the first drive selector switch 130 to be used to laterally move the gear plate 110 on the pivot shaft 104 between a first rotary drive position wherein an application of an actuation motion to the firing trigger 140 results in the application of a rotary drive motion to the rotary drive shaft 150 and a second axial drive position wherein an application of an actuation motion to the firing trigger 140 results in the application of an axial drive motion to an axial drive bar 200. More specifically and with reference to FIGS. 2-4, the axial drive bar 200 is coupled to an axial drive linkage 210 that is configured to releasably interface with the gear plate 110. As can be seen in FIG. 3, the gear plate 110 has an engagement lug 120 formed thereon that has a hole 122 that is sized to receive a first engagement pin 212 that protrudes from the axial drive linkage 210. The axial drive bar 200 is pinned to a linkage bar 214 by a pin 216 that extends through the linkage bar 214 into a slot 218 in one of the handle cases 21. As can be most particularly seen in FIG. 3, the first engagement pin 212 is also attached to the linkage bar 214 and protrudes therethrough into a second slot 220 in the handle case 21. A compression spring 222 is supported within the slot 220 to bias the pin 212 within the slot 220 to the starting position shown in FIG. 3. The axial drive bar 200 has a distal end 201 that is configured to engage a corresponding portion of the particular surgical tool head that has been coupled to the modular surgical instrument 10 to apply the requisite amount of axial drive motion thereto.

Thus, to actuate the axial drive bar 200, the surgeon laterally moves the first drive selection switch 130 in the "L" direction to bring the pin 212 into the hole 122 in the gear plate attached lug 120. This action also moves the gear plate 110 to the axial drive position wherein all of the gear racks 114, 116, 118 are out of meshing engagement with their corresponding pinion gears 152, 154, 156 on the rotary drive shaft 150 and the gear plate 110 is in driving engagement with the axial drive bar 200. Thereafter, the surgeon may depress the firing trigger 140 to drive the axial drive bar 200 distally within the outer shaft casing 70 of the shaft assembly 60. When the surgeon releases the firing trigger 140, the springs 222 and 142 bias the gear plate 110, axial drive bar 200 and firing trigger 140 back to the starting position.

As will be discussed in further detail below, various of the surgical tool head embodiments of the present invention require rotary actuation motions to be applied to various portions of the tool head that are axially displaced from each other. Such axial displacement can be relatively small and may be accomplished without completely de-meshing one of the pinion gears 152, 154, 156 from its respective rack gear 114, 116, 118 so that activation of the firing trigger 140 results in the application of rotary motion to the rotary drive shaft 150. In at least one embodiment, a second axial drive switch 230 is employed. In various forms, the second axial drive switch 230 comprises a slider switch that can be slid between multiple positions which correspond to various axial positions of the rotary drive shaft 150. The slide switch 230 may include, for example, a clevis-type arrangement that permits the rotary drive shaft 150 to rotate relative thereto and serves to apply an axial motion to the rotary drive shaft 150 to move it axially within the handle assembly 20 and outer casing 70 of the shaft assembly 60. See FIG. 1.

Tool Component Acquisition and Operational Adjustment Drive System

Various embodiments of the modular surgical instrument 10 of the present invention include a tool acquisition shaft 240 that axially extends through the rotary drive shaft 150 and is independently movable relative thereto. In various embodiments, the proximal end portion 242 of the tool acquisition shaft 240 has a series of helical threads 244 thereon that is configured to rotatably interface with a closure nut portion 246 interfacing with an adjustment knob 248 located on the proximal end of the handle assembly 20. Such adjustment knob and closure nut arrangements are known in the art and will not be described in further detail herein. See, e.g., U.S. Pat. No. 7,506,791, the disclosure of which has been herein incorporated by reference. Thus, rotation of the adjustment knob 248 relative to the handle assembly 20 will result in the axial movement of the tool acquisition shaft 240 within the rotary drive shaft 150.

Surgical Tool Heads

As is apparent from the foregoing description, various forms of the modular surgical instrument 10 are well-suited for actuating a variety of different forms of surgical tool heads that may be required, for example, during a single surgical operation—particularly those devices/tool heads that are used to perform different surgical procedures or actions within the colon. Such surgical tool heads may be provided in a kit form wherein the kit includes at least two different surgical tool heads for use with a modular surgical instrument 10. In various embodiments, each surgical tool head has an outer casing that has an attachment stem portion that is sized to be received within the distal end 76 of the outer shaft casing 70 of the shaft assembly 60. The distance in which the attachment stem portion extends into the outer shaft casing 70 will dictate the axial position of the rotary drive shaft 150 and ultimately which pinion gear 152, 154, 156 is brought into meshing engagement with its corresponding gear rack 114, 116, 118 thereby dictating the amount of rotary drive motion applied to the rotary drive shaft 150 upon actuation of the firing trigger 140. Further understanding of this unique feature may be gleaned from reference to FIG. 7.

Figure 7:
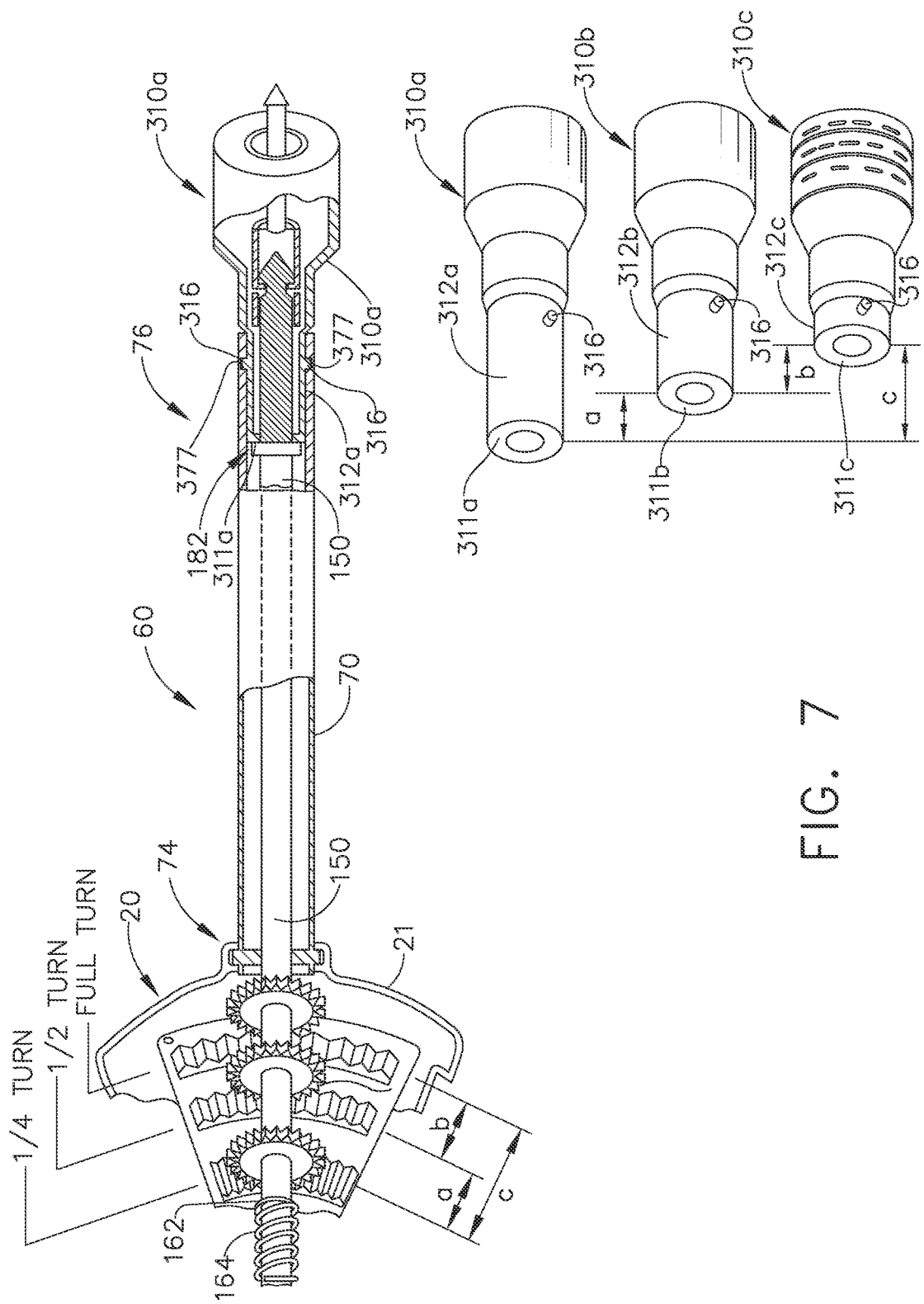
FIG. 7 is another partial cross-sectional view of the handle and shaft assembly of FIG. 6 and three different surgical tool head embodiments of the present invention.
Figure 8:
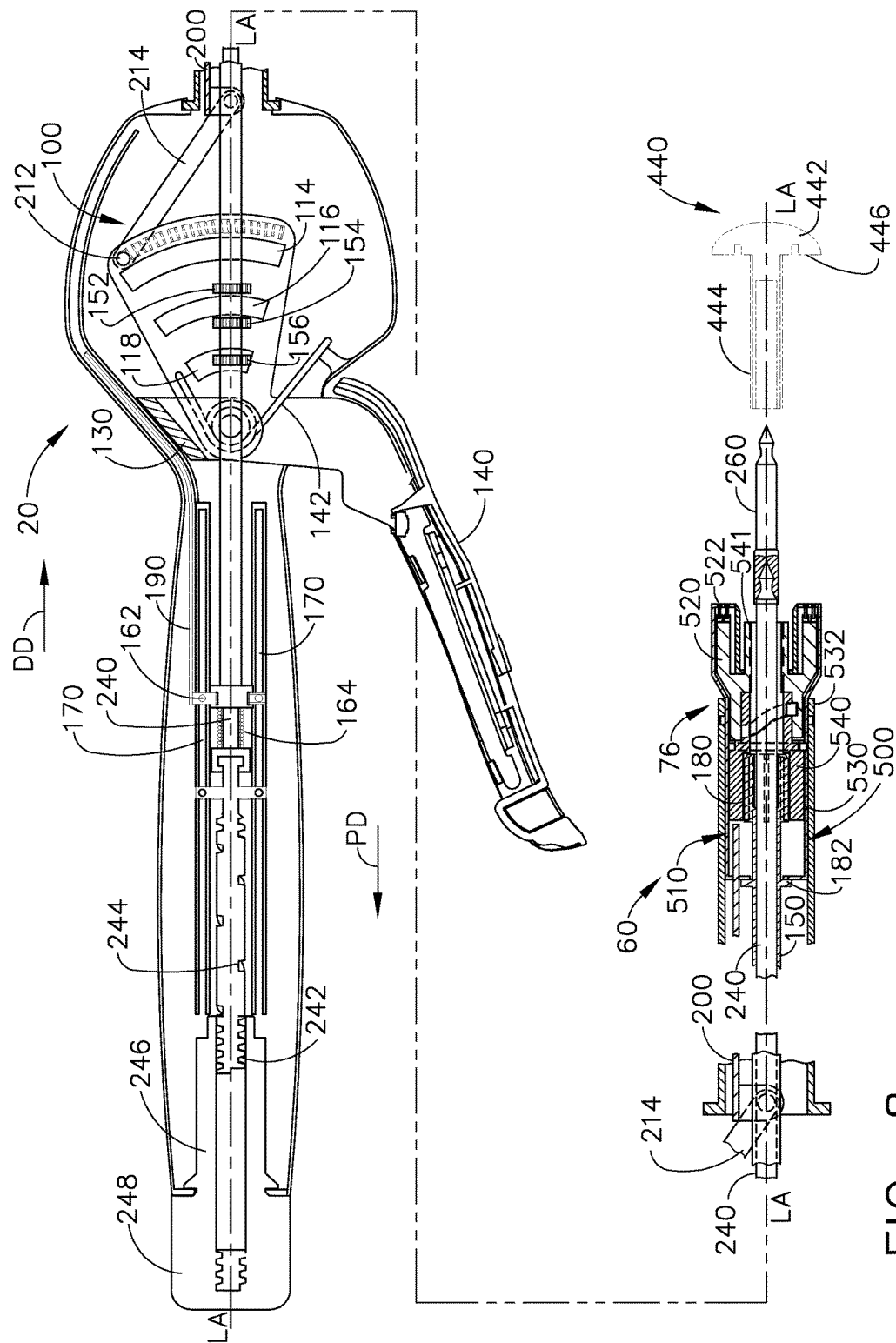
FIG. 8 is a cross-sectional view of one form of a modular surgical instrument embodiment of the present invention attached to another surgical tool head embodiment of the present invention.
Figure 9:
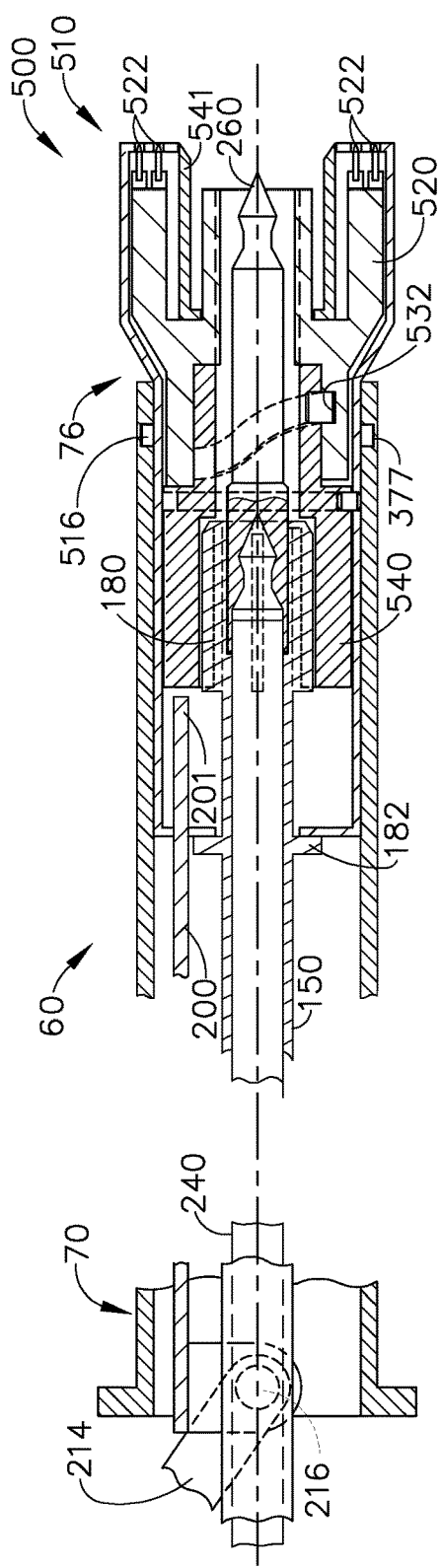
FIG. 9 is a cross-sectional view of the shaft assembly and surgical tool head depicted in FIG. 8.

FIG. 7 illustrates, in general form, three different forms of surgical tool heads 310a, 310b, 310c that each require three different amounts of rotary drive motion for actuation thereof. For example, tool head 310a requires ¼ turn of rotary drive motion to actuate. Tool head 310b requires ½ turn of rotary motion to actuate. Tool head 310c requires one full turn of rotary drive motion to actuate. As can also be seen in that Figure, tool head 310a has an attachment stem 312a that is configured to be inserted into the shaft assembly 60. Thus, when the attachment stem 312a is fully seated in the distal end 76 of the outer shaft casing 70, the end 311a of the attachment stem 310a engages the actuation flange 182 on the rotary drive shaft 150 and biases the rotary drive shaft 150 in the proximal direction "PD" to bring the pinion gear 156 into meshing alignment with its corresponding gear rack 118. Likewise, tool head 310b has an attachment stem 312b that is shorter than attachment stem 312a by distance "a" which corresponds to the distance between the gear rack 118 and 116 as shown. Thus, when the attachment stem 312b is fully seated in the distal end 76 of the outer shaft casing 70, the end 311b of the attachment stem 312b engages the actuation flange 182 and biases the rotary drive shaft 150 in the proximal direction "PD" to bring the pinion gear 154 into meshing alignment with its corresponding gear rack 116. Likewise, tool head 310c has an attachment stem 312c that is shorter than attachment stem 312a by distance "c" which corresponds to the distance between gear racks 118 and 114 and is shorter than attachment stem 312b by distance "b" which corresponds to the distance between the gear racks 116 and 114 as shown. Thus, when the attachment stem 312c is fully seated in the distal end 76 of the outer shaft casing 70, the end 311c of the attachment stem 312a engages the actuation flange 182 on the rotary drive shaft 150 and biases the rotary drive shaft 150 in the proximal direction "PD" to bring the pinion gear 152 into meshing alignment with gear rack 114.

Various surgical tool head embodiments of the present invention also employ a "bayonet-type" attachment configuration to attach the surgical tool head to the shaft assembly 60. In particular, as can be seen in FIG. 7, each of the attachment stems 312a, 312b, and 312c are provided with diametrically-opposed outwardly protruding pins 316. To attach a surgical tool head to the shaft assembly 60, the user aligns the pins 316 with corresponding bayonet-type slots 377 provided in the distal end 76 of the outer shaft casing 70. See FIG. 6. Once the pins 316 are aligned with their respective slots 377, the user inserts the attachment stem portion into the distal end 76 of the outer shaft casing 70 and, when seated therein, rotates the surgical tool head slightly to seat the pins 316 into their respective bayonet slots 377. In alternate embodiments, the pins may be provided on the outer shaft casing and the slots may be provided in the attachment stems.

Referring to FIGS. 2, 4, 5, and 5A, there is shown a surgical tool head 400 that may be effectively used in connection with the various embodiments of the surgical instruments 10 of the present invention. In this embodiment, the surgical tool head 400 comprises a circular stapler head 410 that only requires axial actuation motion for cutting and stapling tissue. As can be seen in those Figures, the circular stapler head 410 has an outer casing 412 that has an attachment stem portion 414 that is sized to be seated into the distal end 76 of the outer shaft casing 70. Attachment pins 416 protrude from the attachment stem 414 and are configured to be received within the bayonet slots 377 in the outer shaft casing 70. A circular staple driver 420 is movably supported within the outer casing 412. The staple driver 420 operably supports a plurality of surgical staples 422 therein in a known fashion. A tissue cutting member 430 is concentrically supported with the staple driver 420.

In use, the circular stapler head 410 must be used in conjunction with an anvil 440 to form the staples therein. FIGS. 2, 4, and 5A illustrate (in broken lines) a conventional circular stapler anvil 440. Those of ordinary skill in the art will appreciate, however, that any of the various collapsible anvil arrangements disclosed in the various patent applications identified above that are presently owned by the assignee of the subject application and which have been incorporated by reference, as well as other anvil arrangements, may be employed. The depicted anvil 440 includes an anvil head 442 that is attached to an anvil stem 444. The anvil head 442 has a staple-forming surface 446 formed thereon that is adapted for confronting relationship with the surgical staples in the staple head 410.

Use of the surgical tool head 400 will now be described. Prior to installing the surgical tool head 400 onto the shaft assembly 60 of the modular surgical instrument 10, the user may bias the first drive selector switch 130 to move the gear plate 110 out of driving engagement with the rotary drive shaft 150 and into driving engagement with the axial drive bar 200. Thus, when the attachment stem 414 of the surgical tool head 400 is inserted into the distal end 76 of the outer shaft casing 70, in at least one embodiment, the rotary drive shaft 150 may be biased axially in the proximal direction without regard to the meshing alignment between the pinion gears 152, 154, 156 and the gear racks 114, 116, 118. In such circumstances, the stem 414 of the tool head 400 can contact the flange 182 extending from the rotary drive shaft 150 and push the drive shaft 150 axially against the biasing force applied by spring 164, as described above. In certain other embodiments, the rotary drive shaft 150 may be biased axially in the proximal direction by the attachment stem 414 without first moving the gear plate 110 out of driving engagement with the gears 152, 154, 156. In at least one such embodiment, the proximal end and/or distal end of each gear 152, 154, 156 may each include a beveled and/or radiused surface which can facilitate the alignment and/or realignment of the gears 152, 154, 156 with their respective gear racks 114, 116, 118, in the event that this is desirable. If the axial motion of the drive bar 200 is desired without the rotation of the rotary drive shaft 150, the gear plate 110 can be disengaged from the drive shaft via selector switch 130 as described above. In any event, the attachment stem 414 of the surgical tool head 400 can be seated in the outer shaft casing 70 and locked in position using the bayonet-type connection arrangement described above. Furthermore, when the surgical tool head 400 is attached to the shaft assembly 60, the distal end 201 of the axial drive bar can 200 seatingly engage the circular stapler driver 420. See FIGS. 2, 4, 5, and 5A. Prior to or after securing the tool head 400 to the shaft assembly 60, in certain embodiments, the user can rotate the control knob 248 at the proximal end of the handle assembly 20 to distally advance the distal end 250 of the adjustment shaft 240 and to enable the user to install a trocar shaft extension 260 thereon. In at least one embodiment, the trocar shaft extension 260 is configured to removably snap onto the distal end 250 of the adjustment shaft 240.

In use, the anvil 440 is introduced into the portion of colon to be cut and stapled using any suitable techniques including any conventional surgical techniques, any of the techniques described in the aforementioned patent applications, or any of the techniques disclosed herein. In order to assemble the anvil 440 to the surgical instrument 10, as described above, the user can insert the portion of the modular surgical instrument 10 supporting the surgical tool head 400 into the colon through the patient's anus and into the portion of the colon to be resected. The surgeon can then manipulate the modular surgical instrument 10 to bring the trocar shaft extension 260 into retaining engagement with the anvil stem 444. Once the anvil stem 444 is attached to the trocar shaft extension 260, the user then rotates the adjustment knob 248 to move the anvil head 442 towards the staple head 410 to capture the tissue to be cut and stapled therebetween. Once the surgeon has moved the anvil head 442 into its final position, the user then squeezes the firing trigger 140 which drives the axial drive bar 200 distally. As the axial drive bar 200 is driven distally, the circular staple driver 420 is driven towards the anvil head 442 thereby driving the surgical staples 422 supported therein into forming engagement with the underside 446 of the anvil head 440 and the cutting knife 430 through the captured tissue. Once the cutting and stapling action has been completed, the user may release the firing trigger 140 to permit the springs 222 and 142 to return the axial drive bar 200 and the firing trigger 140 to the starting position. Thereafter, the surgeon may withdraw the modular surgical instrument 10 from the patient.

Figure 10:
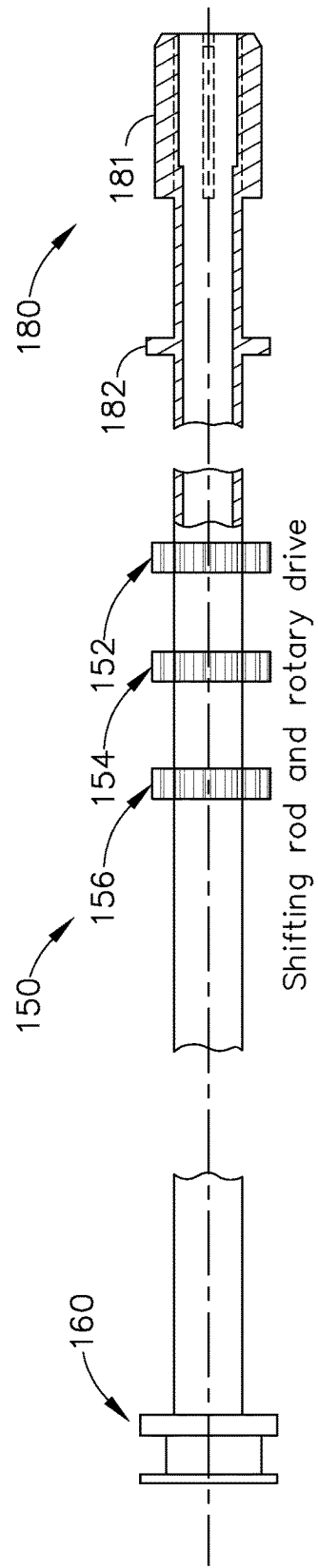
FIG. 10 is a partial side view of one rotary drive shaft embodiment of the present invention.
Figure 11:
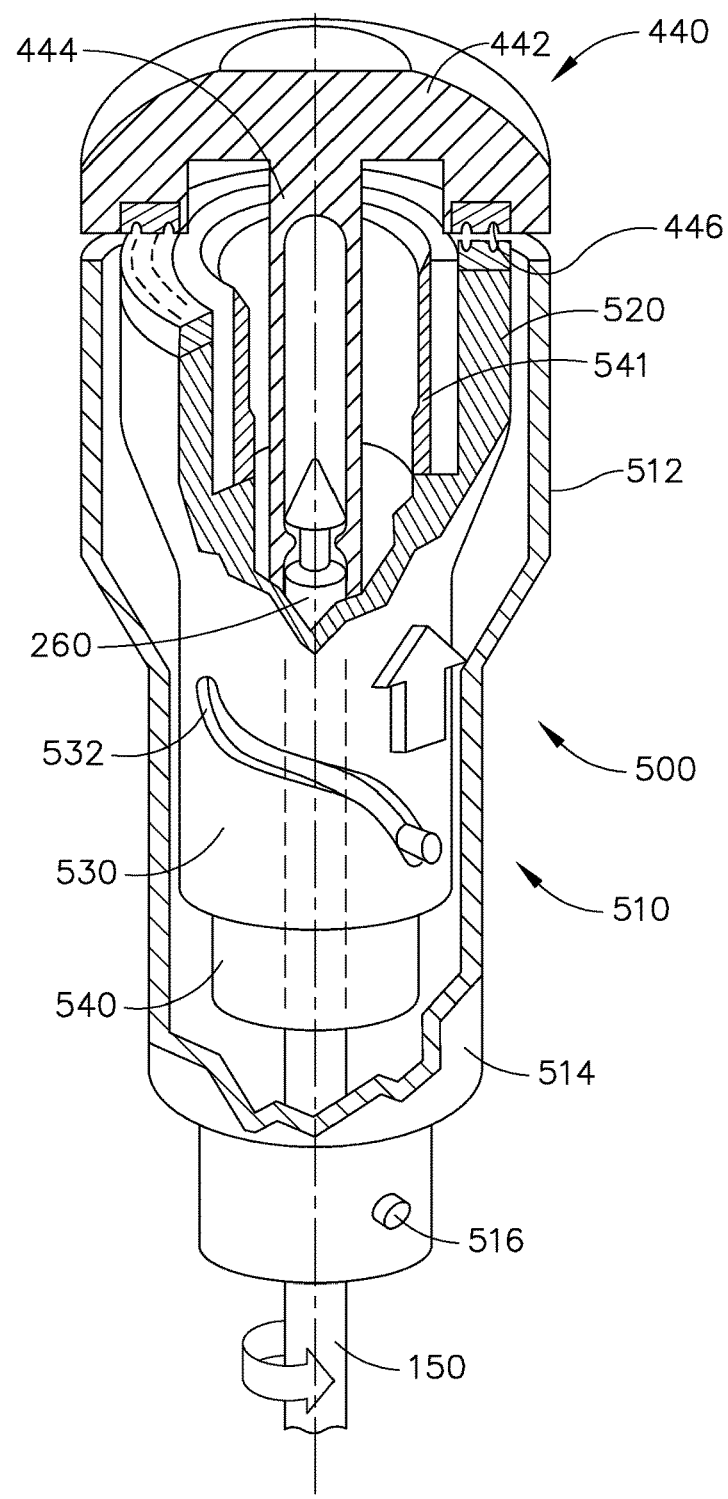
FIG. 11 is a partial cross-sectional perspective view of the surgical tool head depicted in FIGS. 8 and 9.
Figure 12:
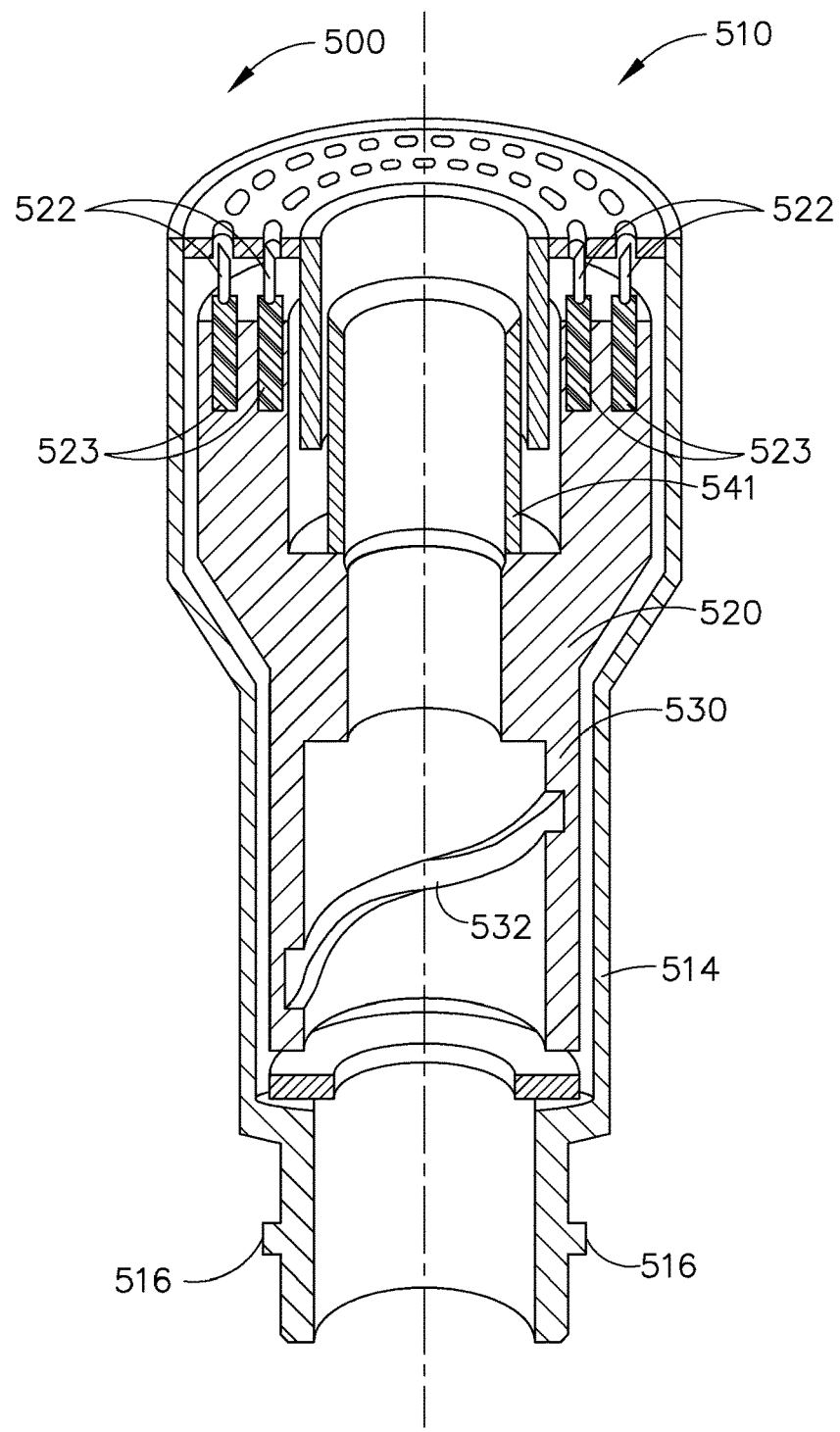
FIG. 12 is a cross-sectional view of the surgical tool head of FIG. 11.
Figure 13:
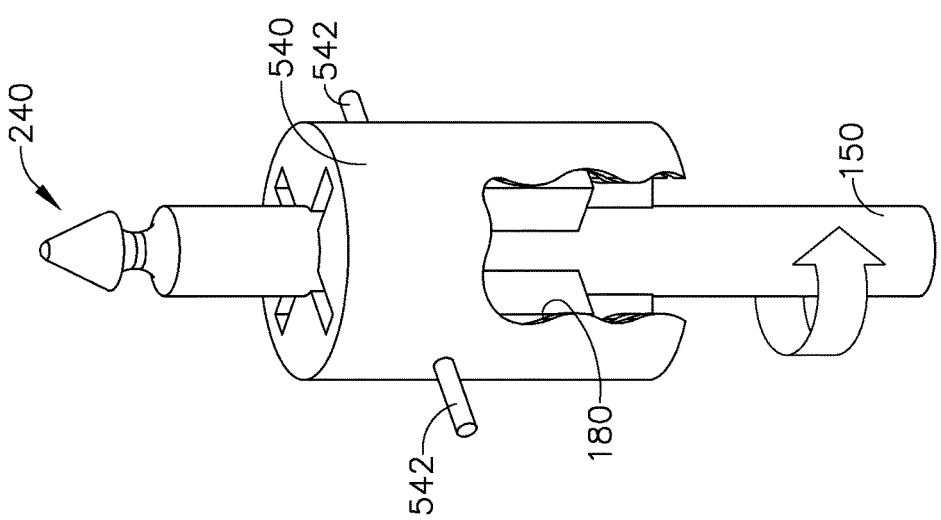
FIG. 13 is a partial perspective view of a portion of the rotary drive shaft and an adapter cap embodiment of the present invention.

FIGS. 8, 9, 11, and 12 illustrate another surgical tool head 500 that may be effectively used in connection with the various embodiments of the modular surgical instrument 10 of the present invention. In this embodiment, the surgical tool head 500 comprises another form of circular stapler head 510. This surgical tool head embodiment requires the application of a rotary drive motion thereto to cause the surgical tool head to cut and staple tissue. As can be seen in FIGS. 8, 9, 11, and 12, the circular stapler head 510 has an outer casing 512 that has an attachment stem portion 514 that is sized to be seated into the distal end 76 of the outer shaft casing 70. Attachment pins 516 protrude from the attachment stem 514 and are configured to be received within the bayonet slots 377 in the outer shaft casing 70. A circular staple driver 520 is movably supported within the outer casing 512. The staple driver 520 operably supports a plurality of surgical staples 522 therein on driver 520 or support members 523 in a known fashion. A tissue cutting member 541 is concentrically attached to the staple driver 520. As can also be seen in FIGS. 11 and 12, the staple driver 520 has a stem portion 530 that has at least one and preferably a pair of helical drive slots 532 therein. The drive slots 532 are configured to receive corresponding drive pins 542 therein that protrude from an adapter cap 540. As can be seen in FIG. 10, the distal end 180 of the rotary drive shaft 150 has a splined outer surface 181 or is fitted with fins for non-rotatably interfacing with the adapter cap 540. Thus, when the user inserts the attachment stem 514 into the distal end 76 of the outer shaft casing 70, the adapter cap 540 slides over the distal end portion 180 of the rotary drive shaft 150 such that rotation of the rotary drive shaft 150 results in rotation of the adapter cap 540. See FIG. 13.

Use of the surgical tool head 500 will now be described. Prior to installing the surgical tool head 500 onto the shaft assembly 60 of the modular surgical instrument 10, the user may bias the first drive selector switch 130 on the handle assembly 20 to move the gear plate 110 out of driving engagement with the rotary drive shaft 150. The attachment stem 514 of the surgical tool head 500 is inserted into the distal end 76 of the outer shaft casing 70 and is affixed thereto in the manner described above. Thus, when the attachment stem 514 of the surgical tool head 500 is inserted into the distal end 76 of the outer shaft casing 70, in at least one embodiment, the rotary drive shaft 150 may be biased axially in the proximal direction without regard to the meshing alignment between the pinion gears 152, 154, 156 and the gear racks 114, 116, 118. In such circumstances, the stem 514 of the tool head 500 can contact the flange 182 extending from the rotary drive shaft 150 and push the drive shaft 150 axially against the biasing force applied by spring 164, as described above. In certain other embodiments, the rotary drive shaft 150 may be biased axially in the proximal direction by the attachment stem 514 without moving the gear plate 110 out of driving engagement with the gears 152, 154, 156. In at least one such embodiment, the proximal end and/or distal end of each gear 152, 154, 156 may each include a beveled and/or radiused surface which can facilitate the alignment and/or realignment of the gears 152, 154, 156 with their respective gear racks 114, 116, 118, as appropriate, when the rotary drive shaft 150 is displaced relative to the gear plate 110. In this embodiment, the circular stapling head 510 may require a ½ rotary turn, for example, to cut and staple tissue. Thus, in this embodiment, the attachment stem 514 is sized to position the rotary drive shaft 150 such that the pinion gear 154 is in alignment with gear rack 116. In the event that the gear plate 110 had been previously displaced by the selector switch 130, the surgeon may move the selector switch 130 to bring the gear rack 116 into meshing engagement with the pinion gear 154. Prior to or after securing the surgical tool head 500 to the shaft assembly 60, similar to the above, the user may rotate the control knob 248 to distally advance the distal end 250 of the adjustment shaft 240 and to enable the user to install a trocar shaft extension 260 thereto. The trocar shaft extension 260 is configured to removably snap onto the distal end 250 of the adjustment shaft 240.

The anvil 440, for example, is then attached to the trocar shaft extension 260 and is brought into confronting relationship with the staple driver 520 as described above. Once the surgeon has moved the anvil head 442 into the final position, the user then squeezes the firing trigger 140 which rotates the rotary drive shaft 150 and the adapter cap 540 thereon. As the adapter cap 540 rotates, the pins 542, by virtue of their engagement with the slots 532 in the staple driver 520, drive the staple driver 520 distally. Such axial motion causes the surgical staples 422 to be driven into forming engagement with the underside 446 of the anvil head 442 and the cutting knife 541 to be driven through the captured tissue. Once the cutting and stapling action has been completed, the user may release the firing trigger 140 to permit the springs 142, 222 to return the axial drive bar 200 and the firing trigger 140 to the starting position. Thereafter, the surgeon may withdraw the modular surgical instrument 10 and surgical tool head 500 from the patient.

Figure 16:
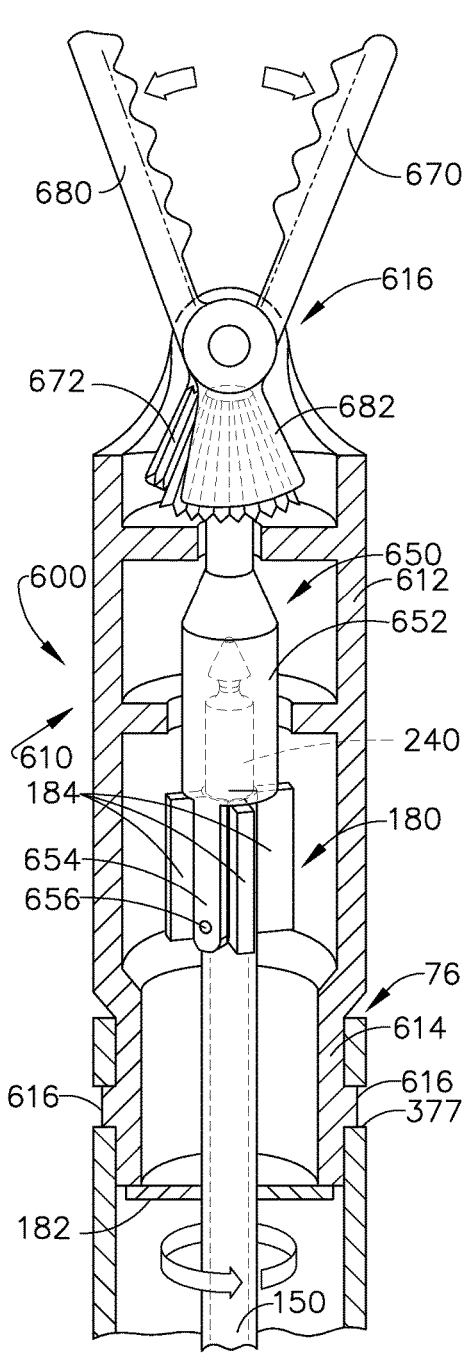
FIG. 16 is a partial cross-sectional view of another surgical tool head embodiment of the present invention with the movable jaws thereof in an open position.
Figure 17:
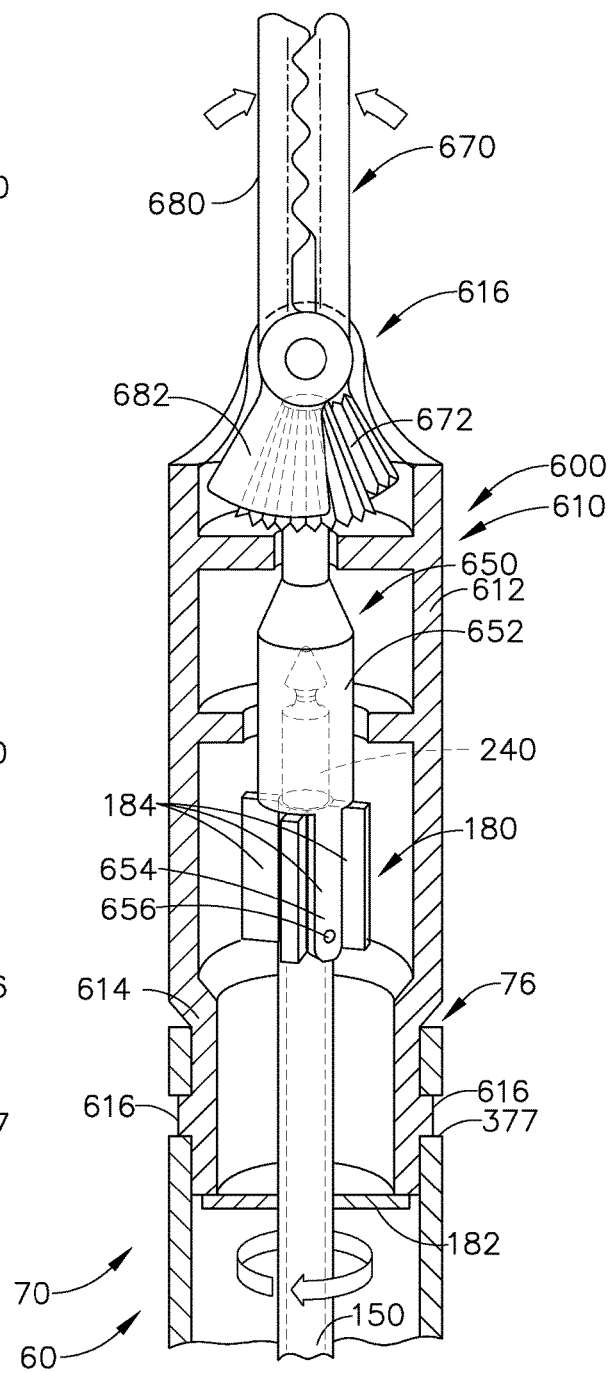
FIG. 17 is another partial cross-sectional view of the surgical tool head embodiment of FIG. 16 with the movable jaws thereof in a closed position.

FIGS. 16 and 17 illustrate another surgical tool head embodiment 600 that may be effectively used in connection with various embodiments of the modular surgical instruments 10 of the present invention. In this embodiment, the surgical tool head 600 comprises a grasper head 610. This embodiment requires the application of a rotary drive motion to actuate the two movable jaws 670, 680 thereof. As can be seen in those Figures, the grasper head 610 has an outer casing 612 that has an attachment stem portion 614 that is sized to be seated into the distal end 76 of the outer shaft casing 70. Attachment pins 616 protrude from the attachment stem 614 and are configured to be received within the bayonet slots 377 in the outer shaft casing 70. The first and second movable jaws 670, 680 are pivotally pinned to the distal end 616 of the casing 612 for pivotal travel about a common pivot axis between an open position (FIG. 16) and a closed position (FIG. 17). The first movable jaw 670 has a first gear portion 672 and the second movable jaw 680 has a second gear portion 682.

Figure 15:
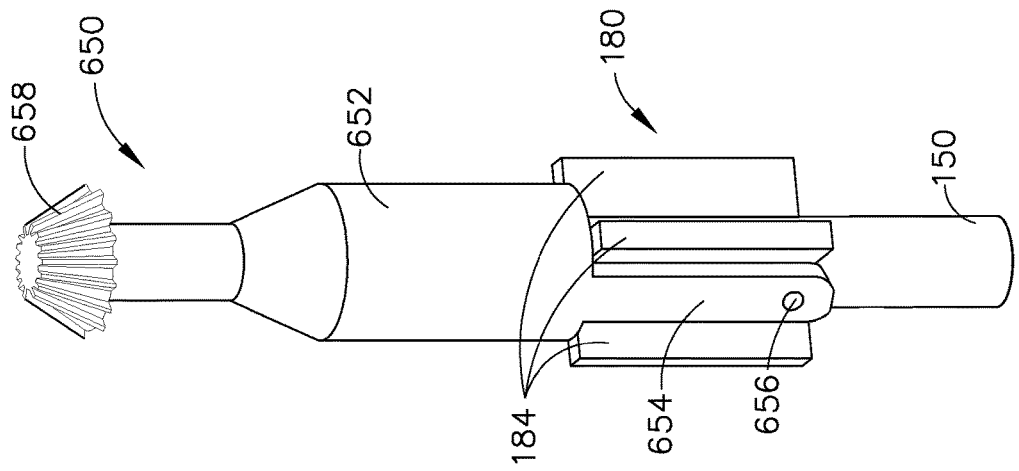
FIG. 15 is an assembled view of the rotary drive shaft and gear drive adapter shaft embodiment of FIG. 14.
Figure 14:
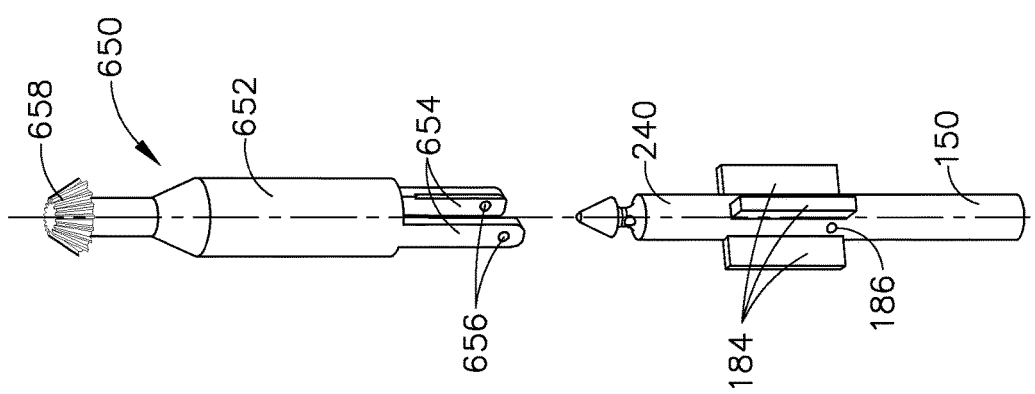
FIG. 14 is an exploded perspective view of a rotary drive shaft embodiment and a gear drive adapter shaft embodiment of the present invention.

As can be seen in FIG. 14, the distal end 180 of the rotary drive shaft 150 has a plurality of (four) fins 184 protruding therefrom for attachment with a gear drive adapter shaft 650. As can be seen in FIGS. 14 and 15, the gear drive adapter shaft 650 has a body portion 652 that has two attachment arms 654 protruding therefrom. Each attachment arm 654 has a hole or dimple 656 therein that is adapted to retainingly engage a corresponding detent 186 formed on the distal end portion 180 of the rotary drive shaft 150. In addition, the distal end of the gear drive adapter shaft 650 has a drive gear 658 formed thereon adapted to meshingly engage the gear portions 672 and 682 on the first and second movable jaws 670, 680 respectively.

Use of the surgical tool head 600 will now be described. Prior to installing the surgical tool head 600 onto the shaft assembly 60 of the modular surgical instrument 10, the user may bias the first drive selector switch 130 on the handle assembly 20 to move the gear plate 110 to a neutral position out of driving engagement with the rotary drive shaft 150. The attachment stem 614 of the surgical tool head 600 is inserted into the distal end 76 of the outer shaft casing 70 and is affixed thereto in the manner described above. In this embodiment, to move the jaws 670, 680 between the open and closed positions, the gear drive adapter shaft 650 may require a ¼ rotary turn, for example. Thus, the attachment stem 614 is sized to position the rotary drive shaft 150 such that the pinion gear 154 is in alignment with gear rack 116.

Thereafter the surgeon may move the first drive selector switch 130 to bring the gear rack 116 into meshing engagement with the pinion gear 154. However, as indicated above, the rotary drive shaft 150 may also be moved axially relative to the gear plate 110 without first moving the gear plate 110 to the neutral position. Prior to securing the surgical tool head 600 to the shaft assembly 60, the user rotates the control knob 248 on the proximal end of the handle assembly 20 to proximally advance the distal end 250 of the adjustment shaft 240 to its proximal-most position. When the attachment stem 614 is inserted into the distal end 76 of the outer shaft casing 70, the gear drive adapter shaft 650 is coupled to the distal end 180 of the rotary drive shaft 150 in the above described manner. The user may then rotate the gear drive adapter shaft 650 to move the jaws 670, 680 to the closed position by squeezing the firing trigger 140. When the user releases the firing trigger, a reverse rotary motion will be applied to the gear drive adapter shaft 650 to pivot the jaws 670, 680 to the open position.

FIGS. 18-20 illustrate another surgical tool head embodiment 700 that may be effectively used in connection with the various embodiments of the modular surgical instruments 10 of the present invention. In this embodiment, the surgical tool head 700 comprises a grasper head 710. This embodiment requires the application of a rotary drive motion to actuate the two movable jaws 770, 780 thereof. As can be seen in those Figures, the grasper head 710 has an outer casing 712 that has an attachment stem portion 714 that is sized to be seated into the distal end 76 of the outer shaft casing 70. Attachment pins 716 protrude from the attachment stem 614 and are configured to be received within the bayonet slots 377 in the outer shaft casing 70. The first and second movable jaws 770, 780 are pivotally pinned to the distal end 716 of the casing 712 for pivotal travel about a common pivot axis between an open position (FIG. 18) and a closed position (FIG. 19). The first movable jaw 770 has a first actuator rod 772 protruding therefrom and the second movable jaw 780 has a second actuator rod 782 protruding therefrom.

This embodiment employs a rotary adapter member 790 that has a central aperture 792 shaped to non-rotatably receive the distal end portion 180 of the rotary drive shaft 150 therein. See FIG. 20. When installed as shown in FIGS. 18 and 19, the first actuator rod 772 extends into a first arcuate actuation slot 794 and the second actuator rod 782 extends into a second arcuate actuation slot 796 in the rotary adapter member 790. Thus, when the user rotates the rotary drive shaft 150 in the above-described manners, the rotary adapter 790 is also rotated which drives the first and second movable jaws 770, 780 to the closed position by virtue of the interaction between the first and second actuator rods 772, 782 and their respective actuation slots 784, 796, respectively. When the user releases the firing trigger a reverse rotary motion will be applied to the rotary adapter 790 to pivot the jaws 770, 780 to the open position.

FIG. 21 illustrates another surgical tool head embodiment 800 that may be effectively used in connection with the various embodiments of the modular surgical instruments 10 of the present invention. In this embodiment, the surgical tool head 800 comprises a circular stapler head 810 that has an outer casing 812 that supports a circular staple cartridge 820 therein. The anvil has been omitted from the Figure for clarity. However, the reader will understand that, except for the differences noted below, the circular stapler head 810 may otherwise operate in the same manner as the stapling heads described above. The circular staple cartridge 820 movably supports an outer circular array 822 of staple drivers 824 and an inner circular array 826 of staple drivers 827. Each staple driver 824, 827 supports one or more surgical staples 828 thereon. This embodiment requires the application of a rotary drive motion to a rotary drive assembly 830 that is rotatably supported within the circular staple cartridge 820 and non-rotatably attached to the distal end 180 of the rotary drive shaft 150 in the above-mentioned manners. The rotary drive assembly 830 includes a driver member 832 that is attached thereto that supports an outer driver wedge 834 configured to drivingly engage the drivers 824 and an inner driver wedge 836 configured to drivingly engage the drivers 826 as the rotary drive assembly 830 is rotated. Once the stapler head 810 has been attached to the shaft assembly 60 in the above-described manner, the user may apply rotary motion to the rotary drive shaft 150 and rotary drive assembly 830. This embodiment requires a full turn of rotary motion. Thus, the attachment stem 814 of the circular stapler head 810 is sized to move the rotary drive shaft 150 such that the pinion gear 152 is brought into meshing alignment with the gear rack 114. Rotary motion is then applied to the rotary drive shaft 150 and rotary drive assembly 830 by depressing the firing trigger 140. As the rotary drive assembly 830 is rotated about the longitudinal axis LA-LA, the outer drive wedge 834 sequentially contacts the outer drivers 824 to sequentially drive the surgical staples 828 supported thereon axially into forming contact with the anvil (not shown). Likewise, as the rotary drive assembly 830 is rotated about the longitudinal axis LA-LA, the inner drive wedge 836 sequentially contacts the inner drivers 826 to sequentially drive the surgical staples 828 supported thereon axially into forming engagement with the anvil. FIG. 22 illustrates a surgical tool head 800' that comprises a circular stapler head 810' that is substantially the same as the circular stapler head 810, except in that embodiment, the drive wedges 834', 836' are integrally formed in the rotary drive adapter 830'.

FIG. 23 illustrates surgical staples 828 that have been driven "horizontally" through an elastomeric retainer ring 850. In this context, the term "horizontally" means that the staples are driven in directions that are substantially transverse to the longitudinal axis LA-LA. During at least one surgical technique, the rectal tissue R can be pulled proximally into the distal end 76 of the outer shaft casing 70 and positioned along the inner sidewall thereof. In various circumstances, a grasper can be inserted upwardly through the outer shaft casing 70 and engaged with the rectal tissue R such that the rectal tissue can then be pulled downwardly into the shaft casing 70. In certain applications, the grasper can include an expandable portion, such as those described herein, for example, which is configured to expand outwardly and engage the rectal tissue. Once engaged with the tissue, the expandable portion of the grasper can be retracted inwardly prior to and/or as the expandable portion is being pulled into the outer shaft casing 70. Once the rectal tissue R has been suitably positioned, a tool head attached to the surgical instrument 10 can be inserted upwardly through the outer shaft casing 70 and positioned relative to the rectal tissue. In various embodiments, the tool head can comprise an annular staple cartridge including staple cavities and staple drivers which can be configured to eject the staples 828 laterally. In at least one such embodiment, the staples 828 and the staple drivers can be horizontally supported around the circumference of the staple cartridge and, likewise, the drive wedge(s) of the tool head and/or staple cartridge can be orientated horizontally to drivingly contact the staple drivers as the drive assembly is rotated.

Further to the above, in various embodiments, the staple cartridge can further comprise the elastomeric retainer ring 850 positioned around the outer surface of the staple cartridge wherein, as the staples 828 are deployed from the staple cartridge, the staples 828 can penetrate the retainer ring 850. In various other embodiments, the ring 850 can be positioned relative to the rectal tissue R before the tool head of the surgical instrument is positioned within the outer shaft casing 70. Once the tool head and staple cartridge are positioned, though, the staples 828 can be driven through the elastomeric retainer ring 850 into the distal end 76 of the outer shaft casing 70 and formed thereby. In at least one such embodiment, the distal end portion 76 of the outer shaft casing 70 may include a hardened anvil insert against which the staples can be deformed. In certain embodiments, the tool head and/or staple cartridge can comprise one or more drive wedges which are rotated about an axis in order to sequentially deploy the staples 828 from the staple cartridge. In certain other embodiments, the tool head and/or staple cartridge can include a cone shaped, or frustoconical, drive wedge which can be displaced distally along an axis and cam, or displace, the staple drivers and the staples 828 simultaneously. In any event, the arrangements described herein can deploy staples within a plane that is substantially perpendicular or substantially transverse to the longitudinal tool axis, although other embodiments are envisioned in which the staples are deployed within any other suitably-oriented plane, for example.

Further to the above, referring now to FIG. 24, a surgical instrument configured to deploy staples horizontally, laterally, radially, or traversely relative to the instrument axis may be used with or without a retaining ring. In such embodiments, the staples 828 can be deployed directly into the rectal tissue R. Whether or not a retaining ring is utilized, referring now to FIG. 25, a stiffening ring can be utilized to at least temporarily stiffen the staple rectal tissue. In various embodiments, a rigid ring 852 can be inserted through the outer shaft casing 70, for example, and fitted within the rectal tissue adjacent to the staple line in order to hold the overall shape of the rectum. In at least one embodiment, the rigid ring 852 can be comprised of metal, for example. Once the rigid ring 852 is no longer needed, a removal tool can be inserted through the rectum to pull the rigid ring 852 out of the surgical site.

Figure 28:
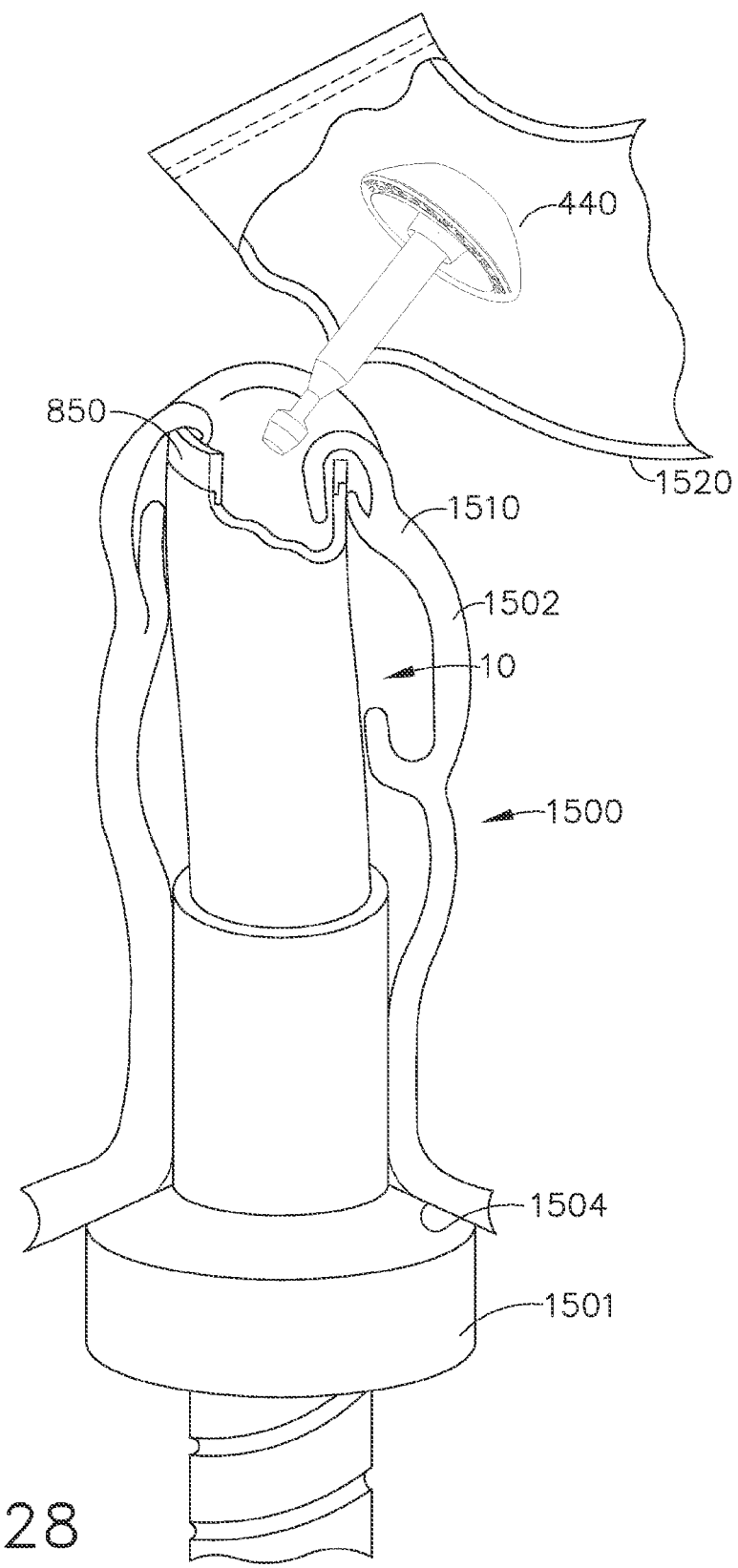
FIG. 28 is a partial perspective view of portions of a patient's colon after the diseased portion has been removed through a port installed in the rectum.

FIG. 26 depicts a diseased specimen 1508 of the colon 1500 after the elastomeric rings 850 have been stapled into each end of the specimen 1508 and the metal rings (if used) have been removed. As can be seen therein, the elastomeric rings 850 serve to bunch up the ends of the diseased specimen 1508 which can reduce the likelihood of depositing diseased cells from inside of the specimen 1508 as it is being removed through the rectum. FIG. 27 illustrates use of a grasper head 900 to pull the diseased colon specimen 1508 through a tube 902 inserted into the rectum. FIG. 28 depicts the colon segments 1502 and 1520 after the specimen or diseased portion 1508 of the colon has been removed. As can be seen in that Figure, a conventional anvil 440 has been inserted through a distal portion 1520 of the colon 1500. The surgical instrument 10 with a horizontal stapling head of the type described above has been inserted through a port 1501 installed into the patient's anus 1504.

Various embodiments of the modular surgical instrument 10 may be used in connection with other forms of surgical tool heads that may be employed to uniformly grip and acquire portions of the colon which facilitates better visualization of the portion of the colon to be transected. Such devices may also be used to ensure that the transection is made substantially perpendicular to the colon. In one embodiment, the surgical tool head 1000 comprises an expandable universal port 1010. See FIGS. 29-32. The universal port 1010 includes an outer shaft portion 1012 that has an attachment stem 1014 that is configured to be attached to the distal end 76 of the outer shaft casing 70 of a modular surgical instrument 10 of the various types and constructions described above. See FIG. 29. However, in other embodiments, the outer shaft portion 1012 may comprise a portion of a dedicated installation tool. In one embodiment, a rotary drive shaft extension 1020 is non-rotatably attached to the distal end portion 180 of the rotary drive shaft 150 in the various manners described above. The rotary drive shaft extension 1020 has a rotary drive gear 1022 attached to its distal end. In this embodiment, only a small amount of rotation may be required to actuate the first and second ring stages of the universal port 1010. Thus, the attachment stem portion 1014 may be sized relative to the flange 182 on the rotary drive shaft 150 such that the pinion gear 156 and gear rack 118 may be brought into meshing alignment and remain in meshing alignment as the rotary drive shaft 150 is axially moved in the distal direction. Such axial movement brings the rotary drive gear 1022 of the rotary drive shaft extension 1020 into meshing engagement with each of the three ring stages of the universal port 1010 as will be described in further detail below.

Figure 29:
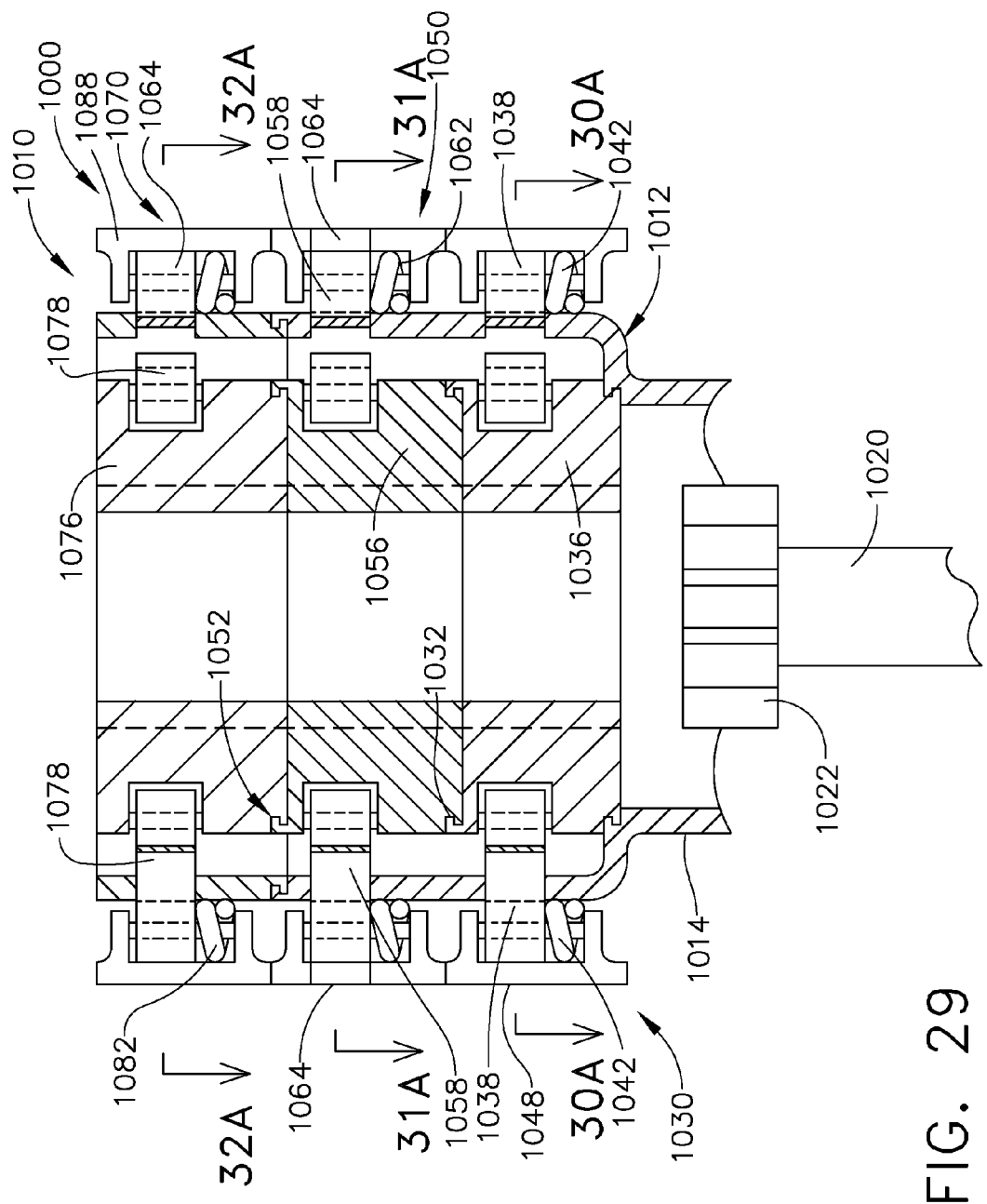
FIG. 29 is a partial cross-sectional view of a universal port member embodiment of the present invention.
Figure 30A:
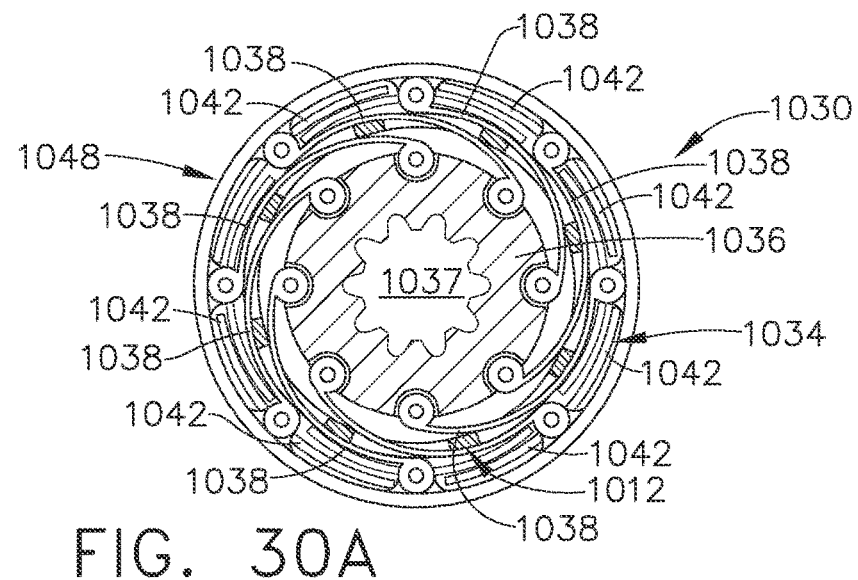
FIG. 30A is a top cross-sectional view of a first ring stage of the universal port member of FIG. 29 taken along line 30A-30A in FIG. 29.
Figure 30B:
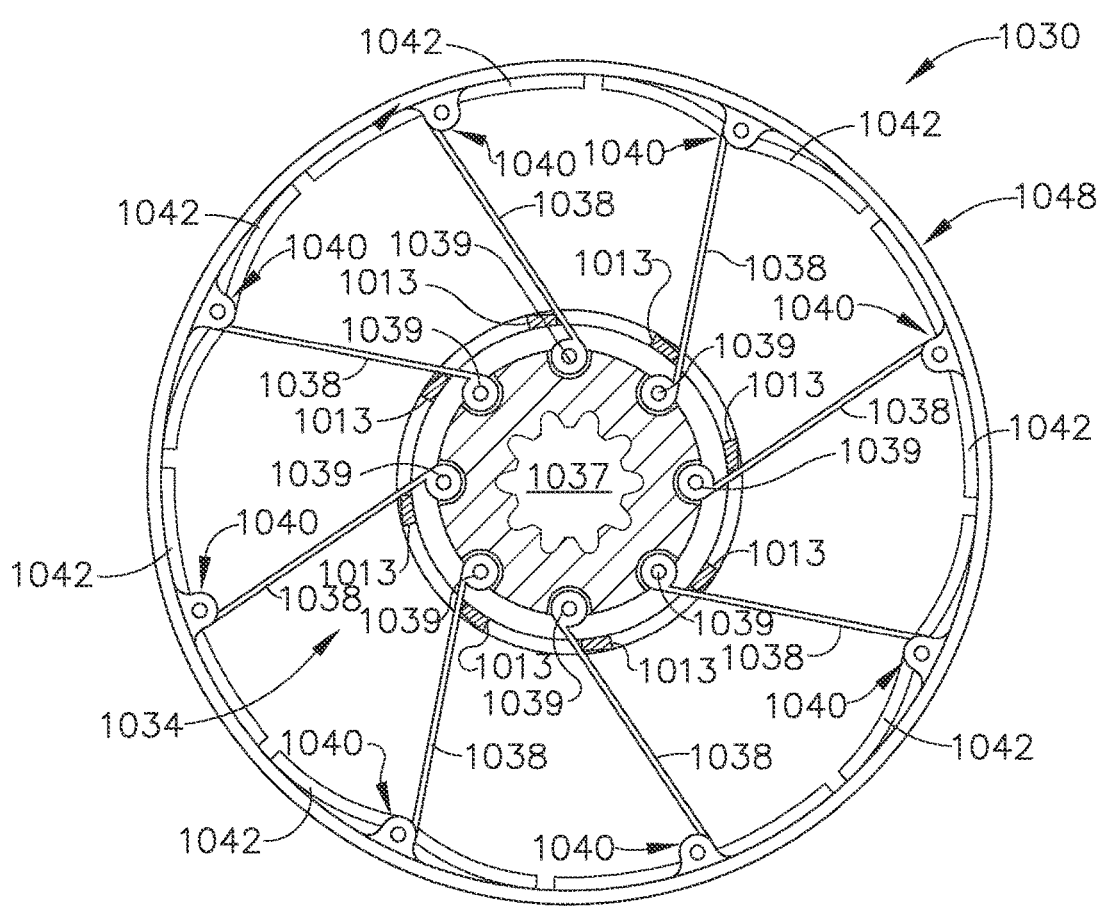
FIG. 30B is another top cross-sectional view of the first ring stage of FIG. 30A in an expanded orientation.

As can be seen in FIG. 29, the universal port 1010 has a first ring stage 1030 that is coupled to a second ring stage 1050 with an attachment feature 1032 that permits relative rotation between the first ring stage 1030 and the second ring stage 1050. The universal port 1010 further has a third ring stage 1070 that is coupled to the second ring stage 1050 by an attachment feature 1052 that permits relative rotation of those components. In at least one embodiment, the first ring stage 1030 is intended to expand the colon. In the depicted embodiment, the first ring stage 1030 includes an expandable first hub assembly 1034 that has an elastomeric outer ring 1048 supported thereon. As can be seen in FIGS. 30A and 30B, the first hub assembly 1034 includes a first central gear hub 1036 that has central gear-receiving aperture 1037 therein that is configured to receive the drive gear 1022 therein. Attached to the first central gear hub 1036 are a plurality of radially extending first spring arms 1038. Each spring arm 1038 has an inner end 1039 that is pivotally pinned to the first central gear hub 1036 and extends through a corresponding opening 1013 in the outer shaft portion 1012. See FIG. 30B. As can be further seen in FIG. 30B, each spring arm 1038 has an outer end 1040 that has a spring member 1042 pivotally pinned thereto. FIG. 30A illustrates the first hub assembly 1034 in a collapsed orientation. Upon application of a rotary motion thereto, the hub assembly 1034 opens to the deployed or expanded orientation depicted in FIG. 30B.

Figure 31A:
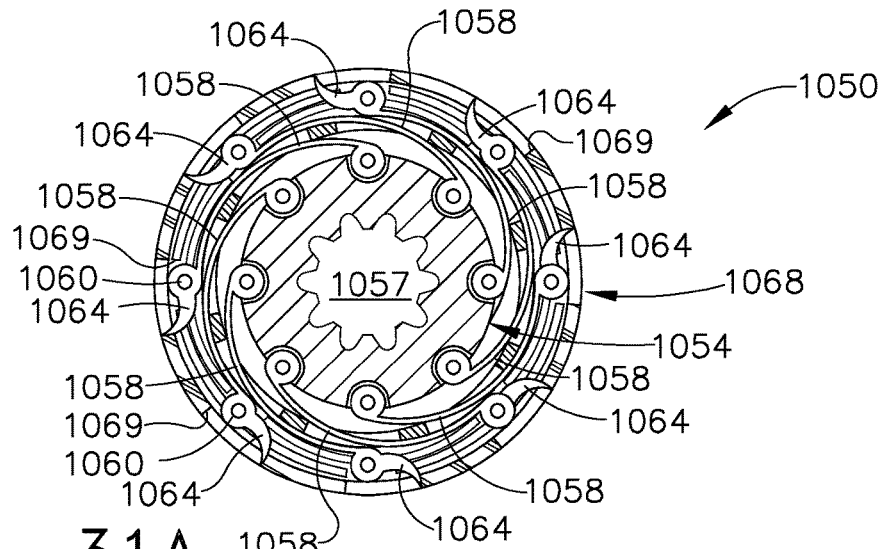
FIG. 31A is a top cross-sectional view of a second ring stage of the universal port member of FIG. 29 taken along line 31A-31A in FIG. 29.
Figure 31B:
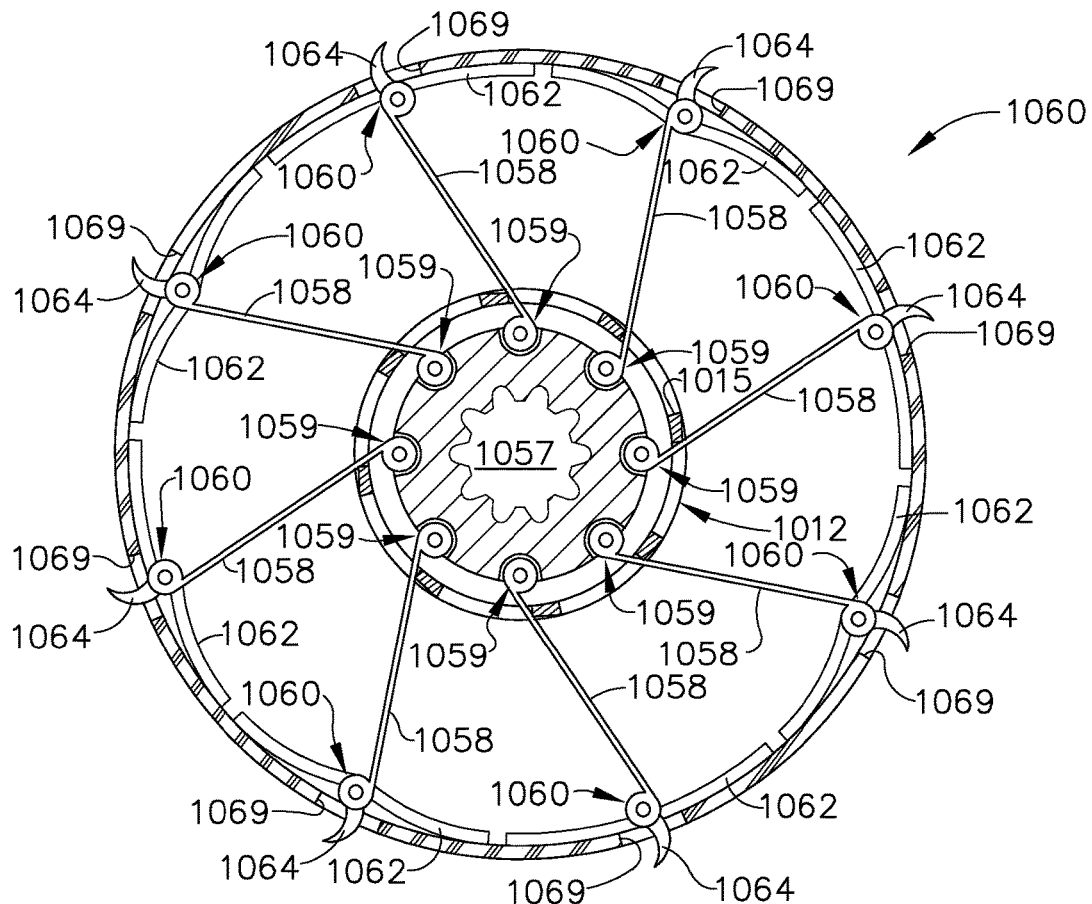
FIG. 31B is another top cross-sectional view of the second ring stage of FIG. 31A in an expanded orientation.

As indicated above, the second ring stage 1050 is attached to the first ring stage 1030 by attachment feature 1032 that permits rotation of the second ring stage 1050 relative to the first ring stage 1030. In the depicted embodiment, the second ring stage 1050 includes an expandable second hub assembly 1054 that has a second elastomeric outer ring 1068 supported thereon. As can be seen in FIGS. 31A and 31B, the second hub assembly 1054 includes a second central gear hub 1056 that has central gear-receiving aperture 1057 therein that is configured to receive the drive gear 1022 therein. Attached to the second central gear hub 1056 is a plurality of radially extending second spring arms 1058. Each second spring arm 1058 has an inner end 1059 that is pivotally pinned to the second central gear hub 1056 and extends through a corresponding opening 1015 in the outer shaft portion 1012. See FIG. 31B. As can be further seen in FIG. 31B, each spring arm 1058 has an outer end 1060 that has a spring member 1062 pivotally pinned thereto. In addition, each spring arm 1058 has a tissue gripping barb 1064 attached thereto that, when deployed, extend through openings 1069 in the second elastomeric outer ring 1068. FIG. 31A illustrates the second hub assembly 1054 in a collapsed orientation. Upon application of a rotary motion thereto, the second hub assembly 1054 opens to the deployed or expanded orientation depicted in FIG. 31B. As the spring arms 1058 move to the expanded orientation, the barbs 1064 are caused to rotate outward.

Figure 32A:
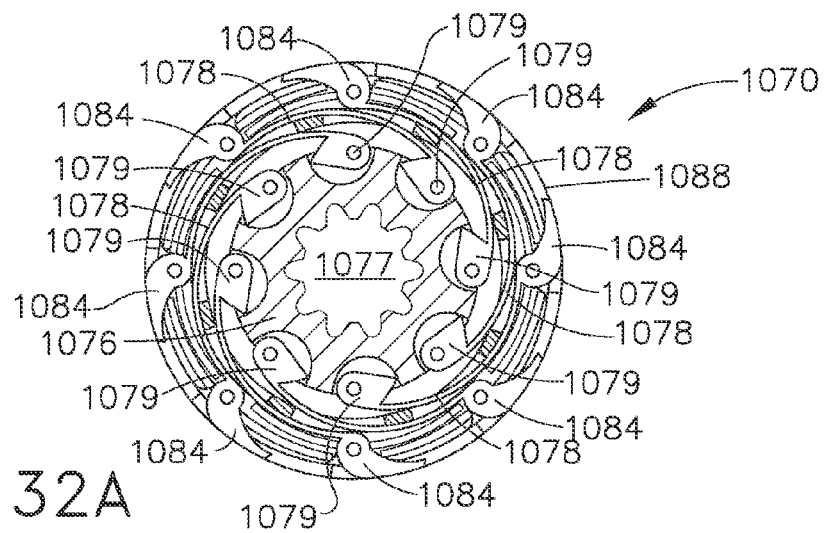
FIG. 32A is a top cross-sectional view of a third ring stage of the universal port member of FIG. 29 taken along line 32A-32A in FIG. 29.
Figure 32B:
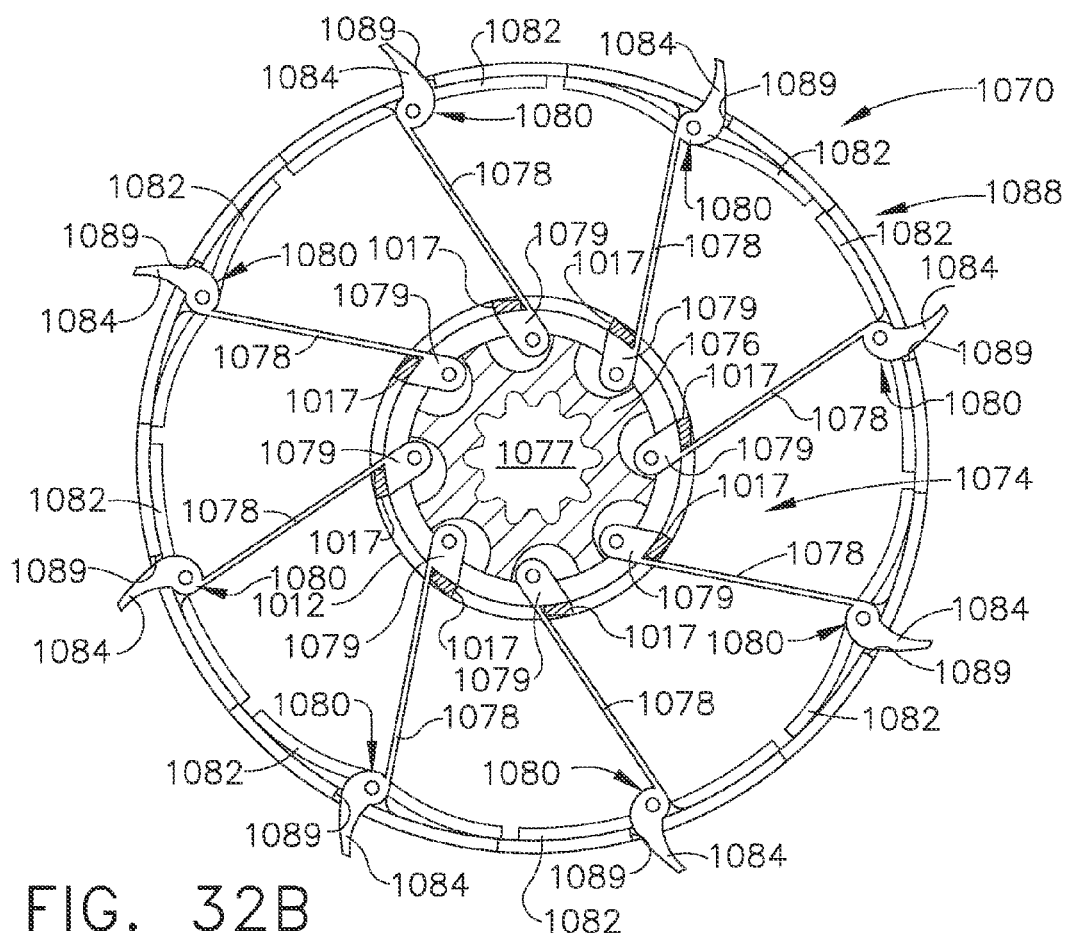
FIG. 32B is another top cross-sectional view of the third ring stage of FIG. 32A in an expanded orientation.

As indicated above, the third ring stage 1070 is attached to the second ring stage 1050 by attachment feature 1052 that permits rotation of the third ring stage 1070 relative to the second ring stage 1050. In the depicted embodiment, the third ring stage 1070 includes an expandable third hub assembly 1074 that has a third elastomeric outer ring 1088 supported thereon. As can be seen in FIGS. 32A and 32B, the third hub assembly 1074 includes a third central gear hub 1076 that has central gear-receiving aperture 1077 therein that is configured to receive the drive gear 1022 therein. Attached to the third central gear hub 1076 is a plurality of radially extending third spring arms 1078. Each third spring arm 1078 has an inner end 1079 that is pivotally pinned to the second central gear hub 1076 and extends through a corresponding opening 1017 in the outer shaft portion 1012. See FIG. 32B. As can be further seen in FIG. 32B, each spring arm 1078 has an outer end 1080 that has a spring member 1082 pivotally pinned thereto. In addition, each spring arm 1078 has a tissue cutting blade 1084 attached thereto that, when deployed, extend through openings 1089 in the third elastomeric outer ring 1088. FIG. 32A illustrates the third hub assembly 1074 in a collapsed orientation. Upon application of a rotary motion thereto, the third hub assembly 1074 opens to the deployed or expanded orientation depicted in FIG. 32B. As the spring arms 1078 move to the expanded orientation, the cutting blades 1084 are caused to rotate outward through the openings 1089. The inner end 1079 of each spring arm 1078 is configured to lockingly engage the shaft 1012 through the corresponding opening 1017 when in the expanded position, such that upon application of a rotary motion thereto (in a counterclockwise direction in FIG. 32B), the spring arms 1078 lock in the extended position and do not collapse when the tissue cutting blades 1084 engage the tissue to be severed.

Operation of the universal port 1010 will now be described. When used in connection with an embodiment of the surgical instrument 10, the surgeon may rotate the control knob 248 to distally advance the distal end 250 of the adjustment shaft 240 to enable the user to install the rotary drive shaft extension 1020 thereon. The rotary drive shaft extension 1020 is configured to removably snap onto or otherwise removably engage the distal end 250 of the adjustment shaft 240. After the rotary drive shaft extension 1020 has been attached, the universal port 1010 is attached to the distal end 76 of the outer shaft casing 70. In particular, the attachment stem 1014 is seated in the outer shaft casing 70 and locked in position using the bayonet-type connection arrangement described above. Prior to inserting the attachment stem 1014 into the distal end 76 of the outer shaft casing 70, the first drive selector switch 130 is moved to disengage the gear plate 110 out of driving engagement with the rotary drive shaft 150 in the manner described above. When the attachment stem 1014 is fully seated within the shaft assembly 60, the rotary drive gear 1022 on the distal end of the rotary drive shaft extension 1020 is brought into meshing engagement with the opening 1037 in the first hub portion 1036. Once the universal port 1010 has been attached to the shaft assembly 60, the first drive selector switch 130 is actuated to bring the gear rack 118 into meshing engagement with the pinion gear 156. The universal port 1010 may then be introduced into the rectum portion 1502 of the colon 1500 through the patient's anus 1504 to the desired deployment position.

Once the universal port 1010 has been positioned in the desired location within the colon 1500, the surgeon may then expand the first ring stage 1030 by squeezing the firing trigger 140. Such action will apply a first rotary motion to the first hub assembly 1034 causing it to move to the expanded orientation shown in FIG. 30B to thereby expand the first outer ring 1048 into expanding contact with the corresponding inner wall portion of the colon 1500. Once the first ring stage 1030 has been expanded, the user may then slide the second axial drive switch 230 to move the rotary drive shaft 150 distally to bring the drive gear 1022 into meshing engagement with the second hub portion 1056 of the second ring stage 1050. Such movement of the rotary drive shaft 150 does not disengage the pinion gear 156 from the rack gear 118. Once the drive gear 1022 has meshingly engaged the second hub portion 1056, the surgeon may once again squeeze the firing trigger 140 to impart a second rotary drive motion to the second hub portion 1056. Such action will apply a second rotary motion to the second hub assembly 1056 causing it to move to the expanded orientation shown in FIG. 31B to thereby expand the second outer ring 1068 and deploy the barbs 1064 into retaining engagement with the corresponding portion of the colon 1500 to retain the universal port 1010 in that location. Thereafter, the user may then slide the second axial drive switch 230 to move the rotary drive shaft 150 distally to bring the drive gear 1022 into meshing engagement with the third hub portion 1076 of the third ring stage 1070. Such movement of the rotary drive shaft 150 does not disengage the pinion gear 156 from the rack gear 118. Once the drive gear 1022 has meshingly engaged the third hub portion 1076, the surgeon may once again squeeze the firing trigger 140 to impart a third rotary drive motion to the third hub portion 1076. Such action will apply a third rotary motion to the third hub assembly 1076 causing it to move to the expanded orientation shown in FIG. 32B to thereby expand the third outer ring 1088 and deploy the cutting blades 1064 outwardly through the adjacent colon tissue. As the third ring stage 1070 is rotated, the cutting blades 1064 sever the colon at that location. While the above-described operation of the universal port 1010 employs the use of the modular surgical instrument 10 of various embodiments of the present invention, other embodiments may employ a dedicated tool for actuation of the ring stages of the universal port in the manners described above without departing from the spirit and scope of various embodiments of the present invention.

Figure 33:
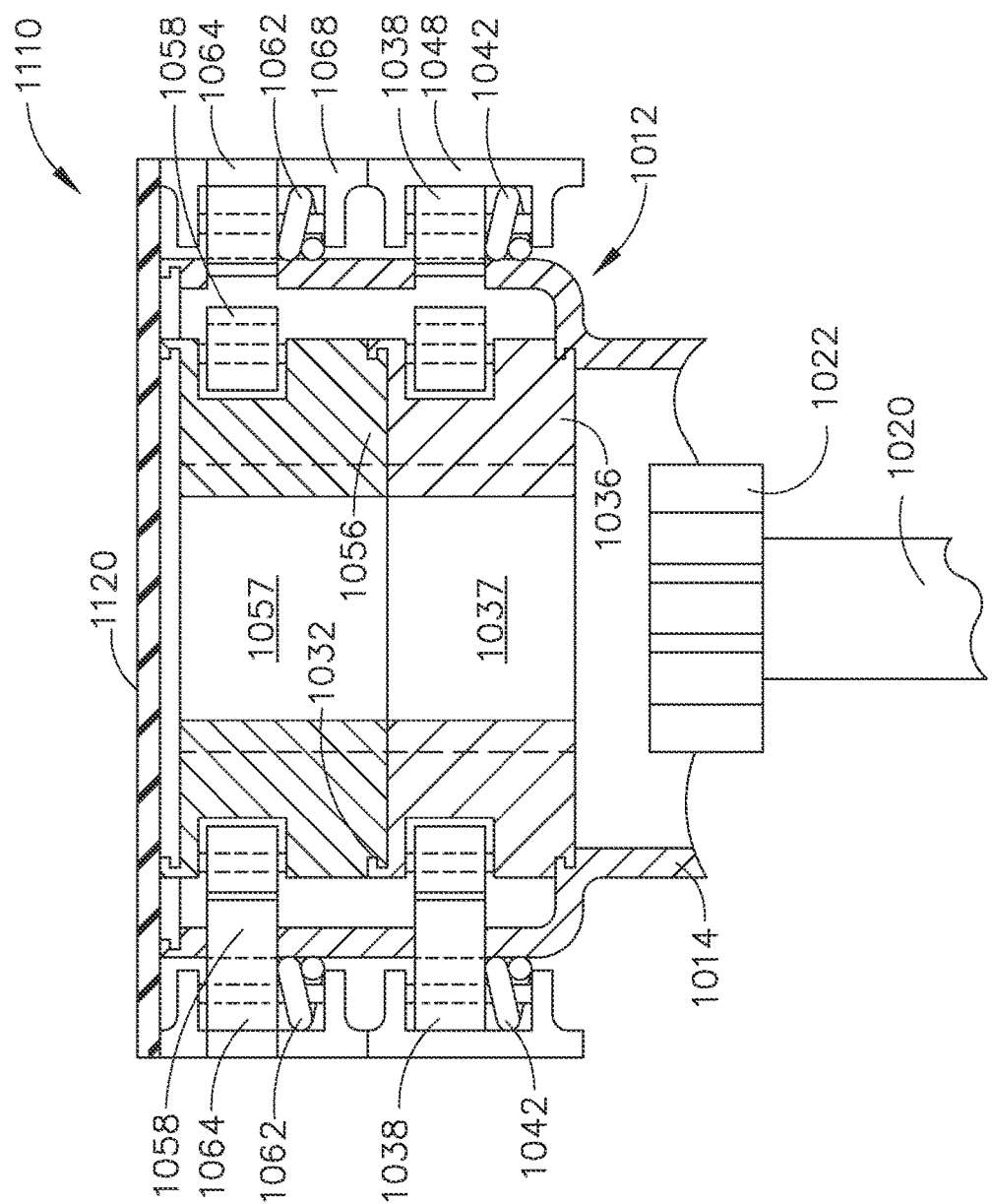
FIG. 33 is a cross-sectional view of another universal port embodiment of the present invention.

FIG. 33 illustrates another universal port embodiment 1110 that only employs two of the ring stages employed by universal port 1010. For example, as shown, the embodiment 1110 illustrates use of the first and second ring stages 1030, 1050 that operate in the same manner described above. However, other embodiments contemplate use of the second and third ring stages 1050, 1070. In either case, the universal port 1110 may be fitted with an occlusion cover to prevent infiltration of tissue into the portion of the colon in which the universal port 1110 has been installed. For example, in one embodiment, the distal-most ring stage (either 1050 or 1070) has a diaphragm assembly 1120 attached thereto. FIG. 33A illustrates a centrally disposed segmented diaphragm assembly 1120. In alternative embodiments, a cover or cap 1121 may be attached to the distal-most ring stage (either 1050 or 1070) as shown in FIG. 33B.

Figure 34:
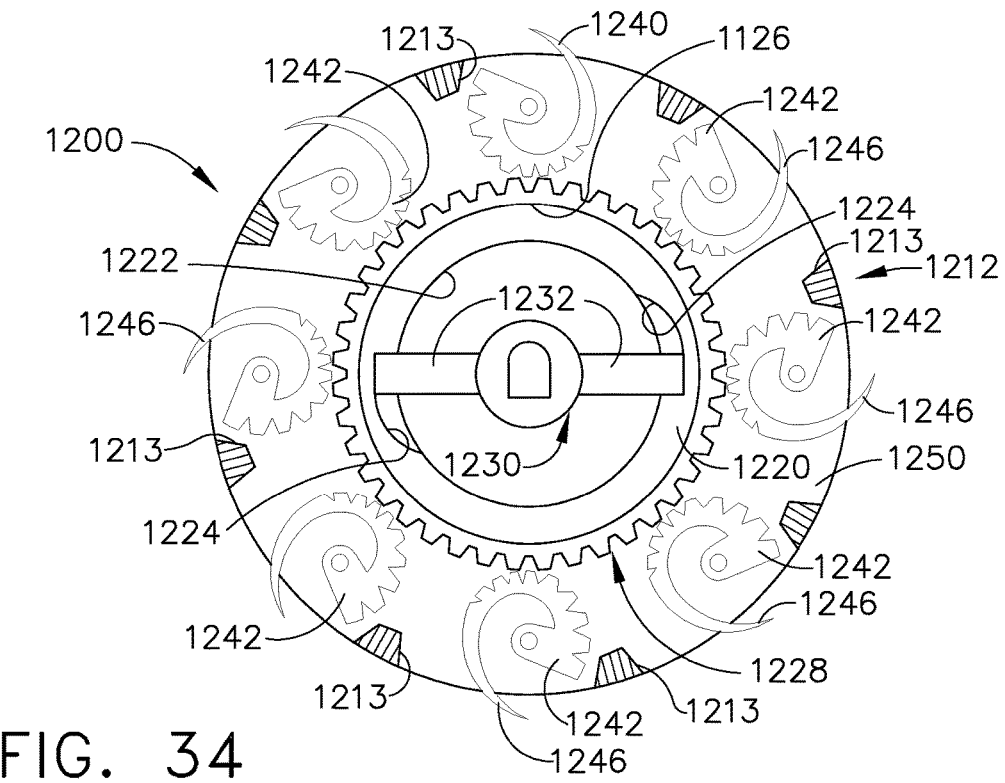
FIG. 34 is a top cross-sectional view of another surgical tool head embodiment of the present invention.
Figure 35:
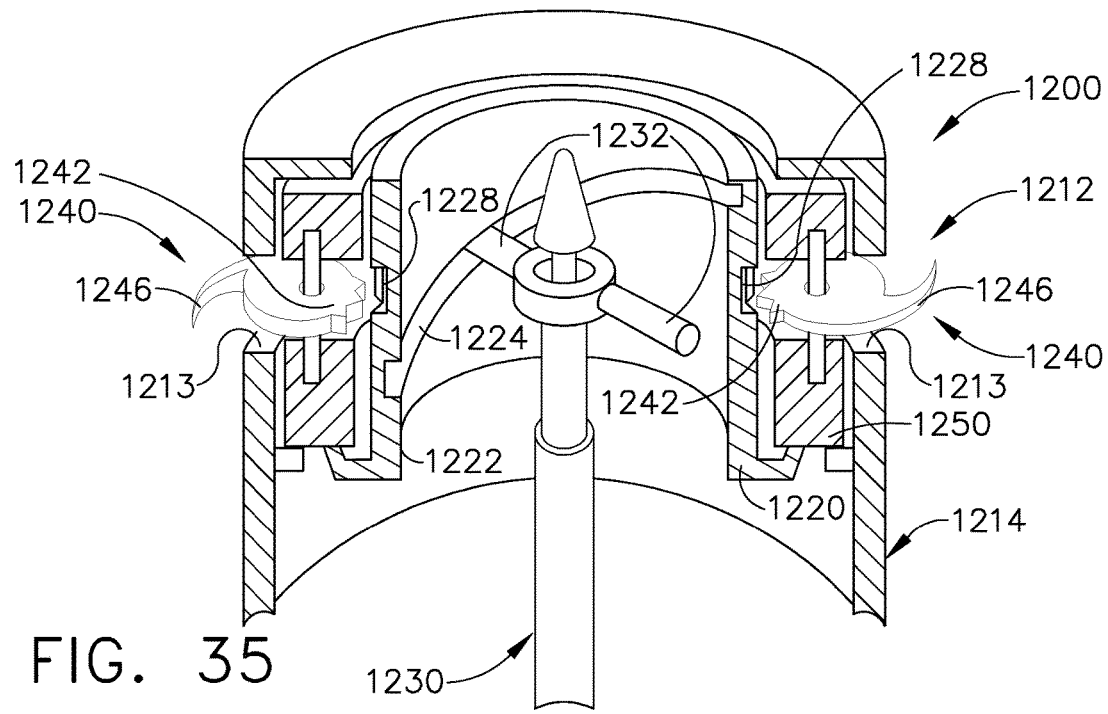
FIG. 35 is a partial cross-sectional elevational view of the surgical tool head embodiment of FIG. 34.

FIGS. 34 and 35 illustrate yet another universal port embodiment 1200 of the present invention that may be used in connection with the surgical instrument 10 or with another dedicated instrument capable of applying axial actuation motions thereto. In the depicted embodiment, the universal port 1200 includes an annular port body or outer casing 1212 that has a stem portion 1214 that is configured for removable attachment to the distal end 76 of the outer shaft casing 70 of an embodiment of the surgical instrument 10 in the above-described manner. A deployment drive assembly in the form of a rotary drive hub 1220 is rotatably supported within the outer casing 1212. As can be seen in FIG. 34, the rotary drive hub 1220 has an inner bore wall 1222 that has a pair of helical slots 1224 therein. The slots 1224 are configured to receive a corresponding actuator pin 1232 that is attached to a drive shaft extension 1230 that is attached to the adjustment shaft 240 employing any of the above-described or similar attachment arrangements. Thus, by distally advancing the drive shaft extension 1230 by rotating the control knob 248, the rotary drive hub 1220 is rotated about the longitudinal axis LA-LA by virtue of the interaction between the actuator pins 1232 and helical slots 1224.

As can be seen in FIGS. 34 and 35, a drive gear 1228 is formed around the outer circumference 1126 of the rotary drive hub 1220. The drive gear 1228 is supported to meshingly engage with a gear portion 1242 on a plurality of tissue barb assemblies 1240 that are each rotatably supported on an annular support ring 1250 as shown. The tissue barb assemblies 1240 have a hook portion 1246 thereon that are adapted to hookingly engage the colon when the universal port 1200 has been deployed therein. Each hook portion 1246 is configured to protrude through a corresponding opening 1213 in the outer casing 1212. Thus, application of the axial drive motion to the adjustment shaft 240 ultimately causes the rotary drive hub 1220 to rotate and deploy the hook portions 1246 into the adjacent colon tissue.

Figure 36:
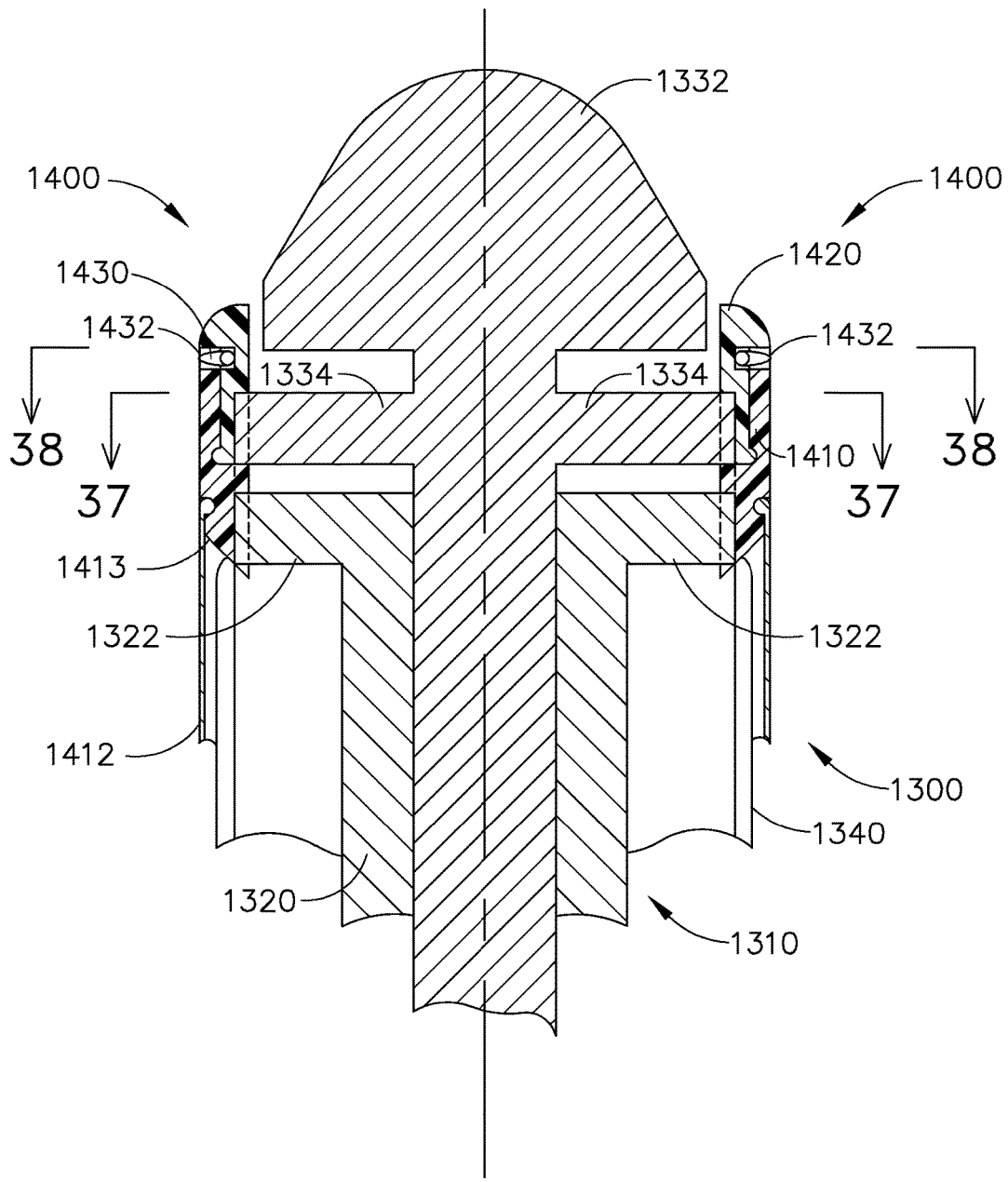
FIG. 36 is a partial cross-sectional view of another universal port embodiment of the present invention in connection with an installation tool.
Figure 37:
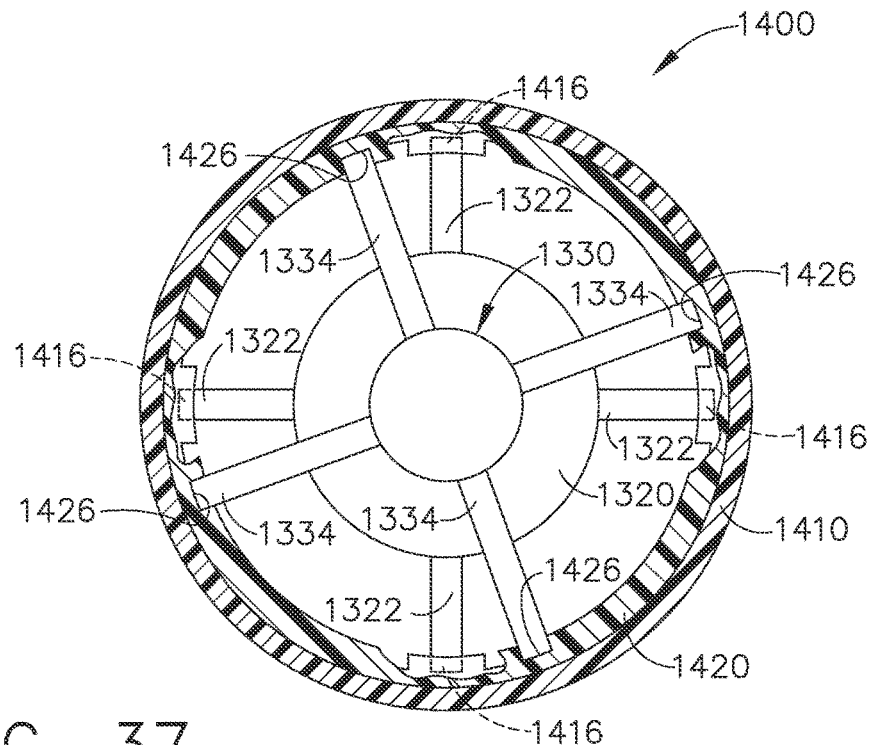
FIG. 37 is a top cross-sectional view of the universal port and installation tool embodiments of FIG. 36 taken along line 37-37 in FIG. 36.
Figure 38:
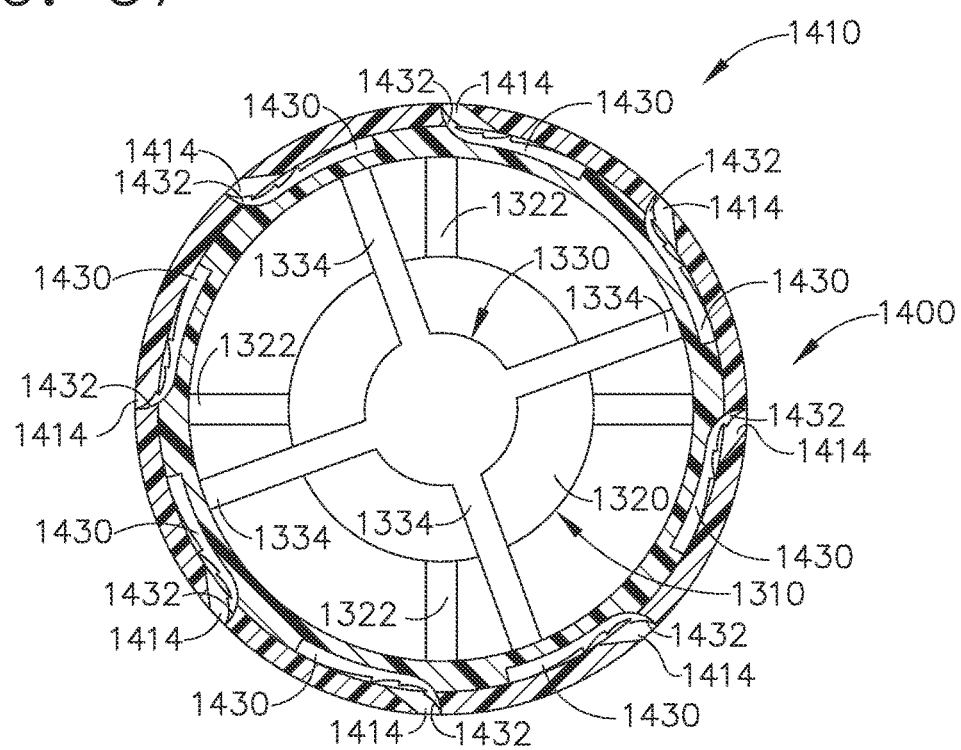
FIG. 38 is a top cross-sectional view of the universal port and installation tool embodiments of FIGS. 36 and 37 taken along line 38-38 in FIG. 36.
Figure 39:
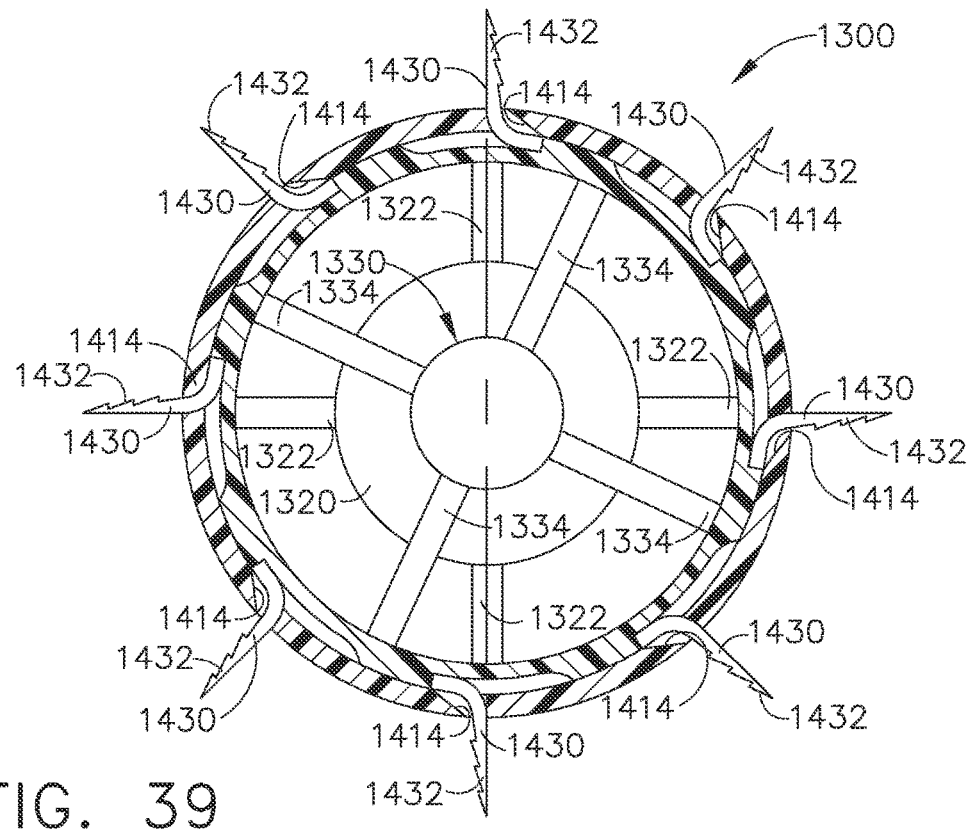
FIG. 39 is a top cross-sectional view of the universal port and installation tool embodiments of FIGS. 36-38 with the tissue retaining barbs in a deployed position.
Figure 40:
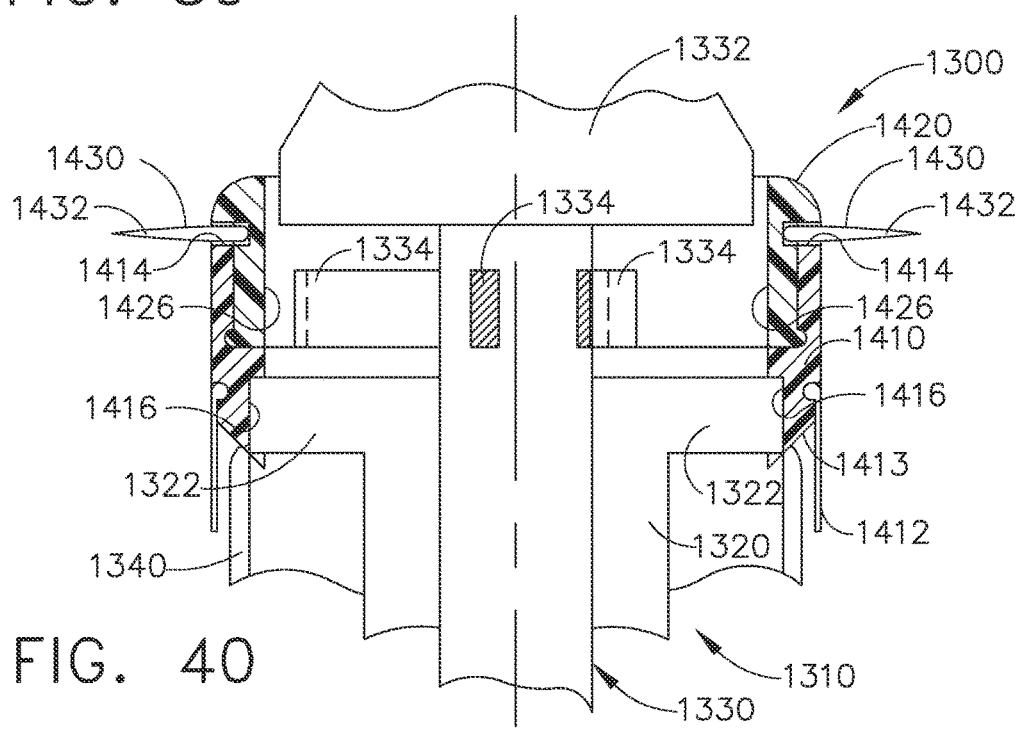
FIG. 40 is a side cross-sectional view of the universal port and installation tool embodiments as depicted in FIG. 39.

FIGS. 36-40 illustrate another universal port embodiment 1400 of the present invention that may be used in connection with an embodiment of the modular surgical instrument 10 or with a dedicated instrument 1310 that has a hollow support shaft 1320 that rotatably supports a rotary drive shaft assembly 1330 therein. Additionally, FIGS. 36 and 40 illustrate use the surgical instrument 1310 with a hollow support or stiffening tube 1340, the purpose of which will be discussed in further detail below. As can be seen in FIGS. 36-40, the hollow support shaft 1320 has a plurality of first support arms 1322 protruding therefrom. The rotary drive shaft assembly 1330 has a substantially blunt distal end 1332 and a plurality of second arms 1334 radially extending therefrom. The drive shaft assembly 1330 is rotatably supported within the support shaft 1320 and is configured to interface with a handle or other source of rotary motion.

In various embodiments, the universal port 1400 has first annular port body in the form of an outer ring portion 1410 and a second annular port body in the form of an inner ring portion 1420. In at least one form, the inner and outer ring portions 1410, 1420 are fabricated from a rigid polymer or other suitable material and are attached together as shown to enable the outer ring 1410 to rotate relative to the inner ring 1420. A flexible sleeve 1412 is attached to the outer circumference of the first ring stage 1410 and extends beyond the proximal end 1413 thereof as shown and preferably is long enough to protrude out of the patient's anus. As will become further apparent as the present Detailed Description proceeds, the sleeve 1412 forms a passageway extending from the universal port 1400 which can make repeated insertions of various surgical instruments into the rectum easier and simpler and may also serve as a wound protector and shield for preventing contact between the extracted specimen and the rectum. Thus, the sleeve 1412 may minimize the likelihood of "seeding" and makes extraction of the diseased specimen easier. In various embodiments, the sleeve 1412 is fabricated from a puncture-resistant weave. In other embodiments, the sleeve has a plastic reducing spiral built therein which could provide the sleeve with "funnel-like" attributes to further the passage of large masses of tissue therethrough.

As can be seen in FIGS. 38 and 39, the inner ring 1420 has a plurality of barbed sutures 1430 spaced equally around its outer circumference. Each tissue barb 1430 has an end portion 1432 that extends into a corresponding slot 1414 in the outer ring portion 1410. The slots 1414 are shaped such that when the universal port 1400 is in the un-deployed or insertion state, the end portion 1432 is substantially completely contained within the slot 1414 and when the inner ring 1420 is rotated relative to the outer ring 1410, the suture barbs 1430 are deployed therefrom as shown in FIGS. 39 and 40.

Figure 41A:
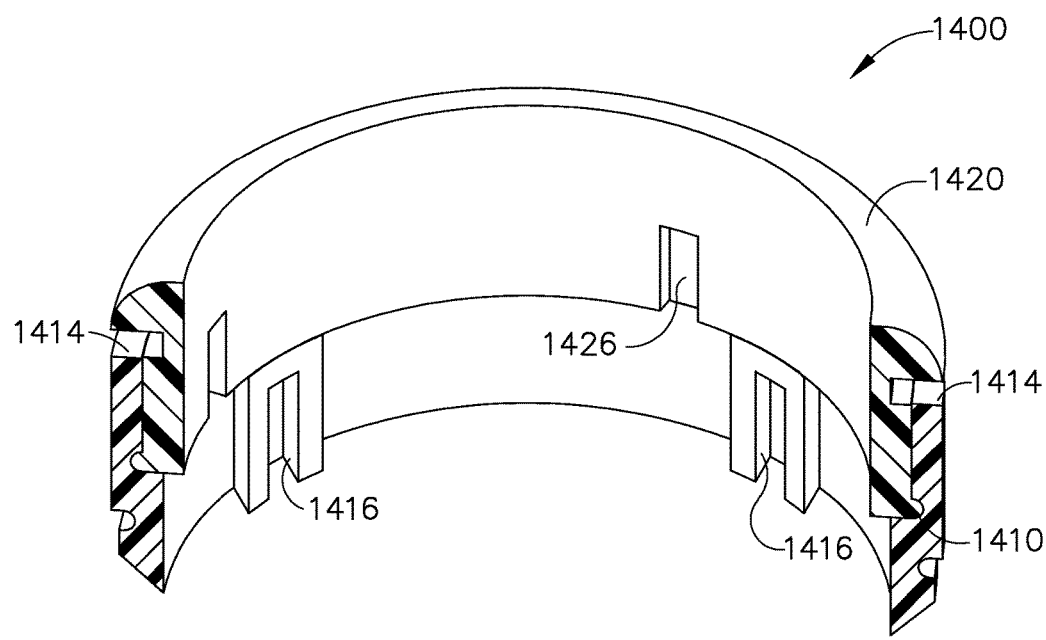
FIG. 41A is a cross-sectional view of the universal port of FIGS. 36-40.
Figure 41B:
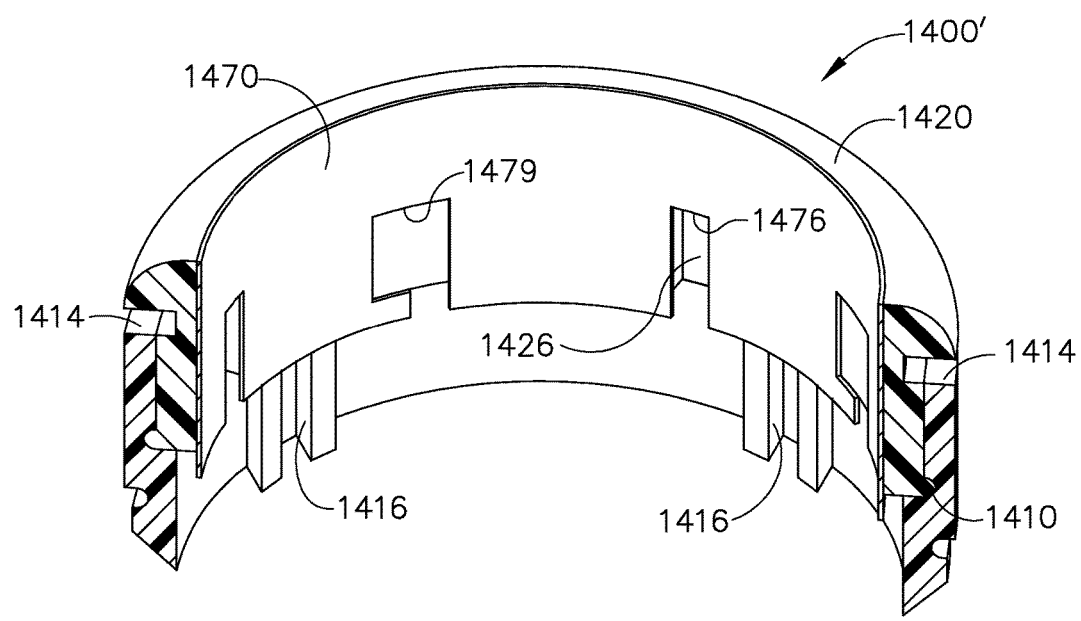
FIG. 41B is a cross-sectional view of a universal port in accordance with at least one alternative embodiment.

As indicated above, the hollow support shaft 1320 has a plurality of first support arms 1322 radially protruding therefrom and the rotary drive shaft assembly 1330 has a plurality of second support arms 1334 protruding therefrom. As can be seen in FIGS. 40 and 41A-B, the ends of the first support arms 1322 are adapted to be received within corresponding closed end slot formations 1416 formed along the inner circumference of the outer ring 1410. Likewise, the ends of the second support arms 1334 are adapted to be received within corresponding closed end slot formations 1426 formed along the inner circumference of the inner ring 1420.

Figure 42:
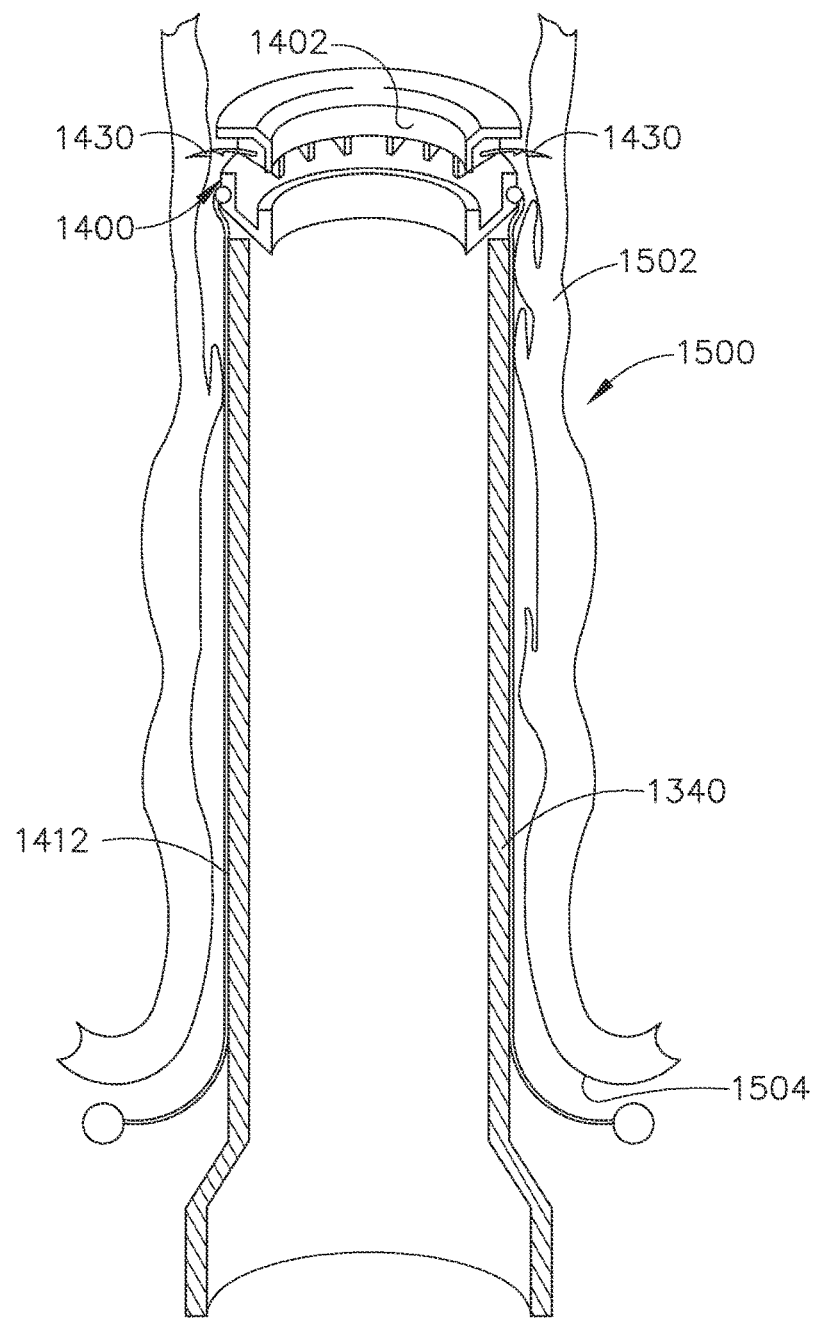
FIG. 42 is a partial cross-sectional view of a universal port embodiment of the present invention and insertion tube embodiment of the present invention positioned within the rectum.
Figure 43:
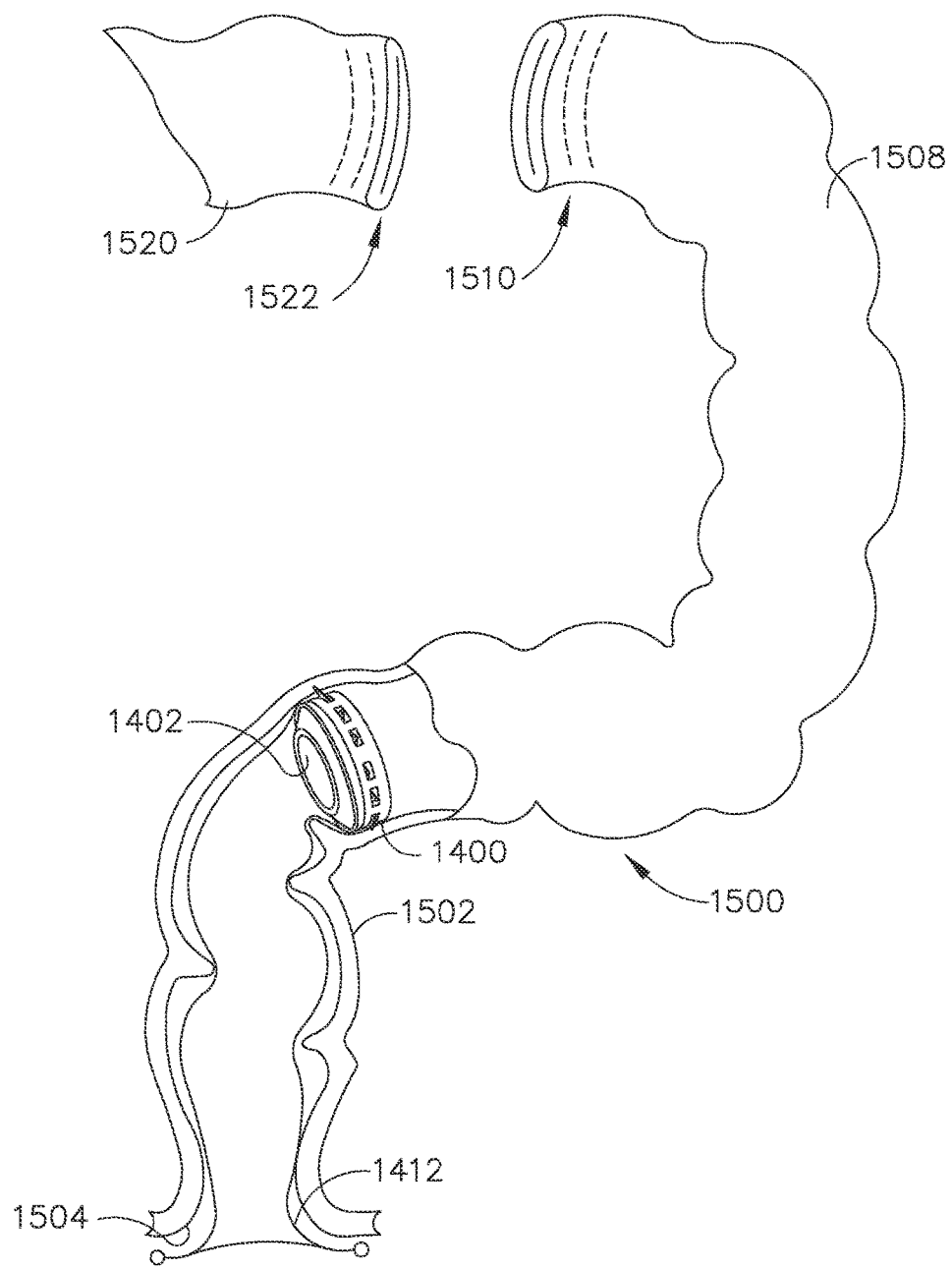
FIG. 43 illustrates a universal port embodiment of the present invention installed in the rectum and wherein a diseased portion of the colon has been severed from a distal portion of the colon.
Figure 44:
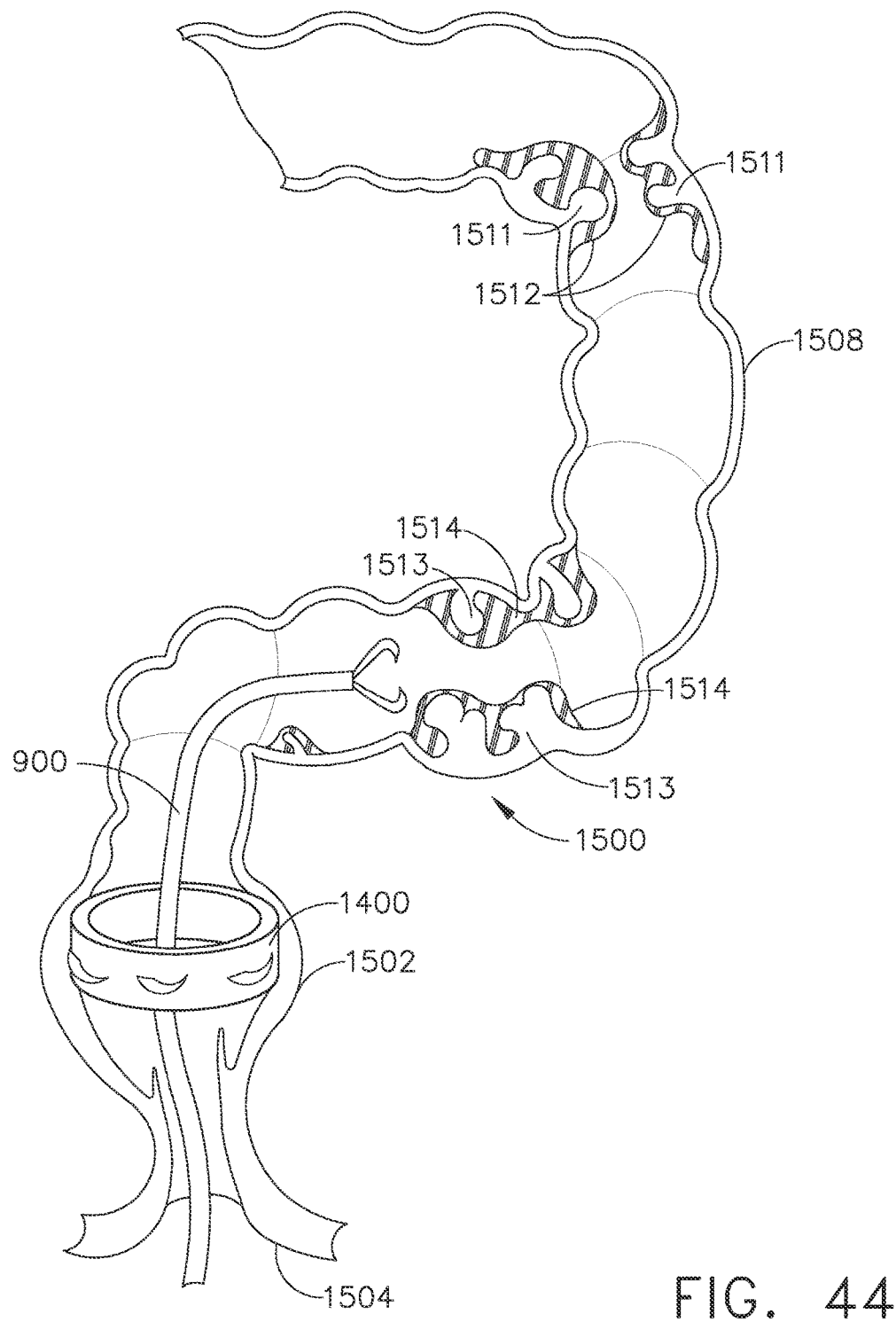
FIG. 44 illustrates use of a grasping instrument through a universal port embodiment of the present invention.

Use of the universal port 1400 will now be explained. Prior to insertion into the colon, the universal port 1400 is installed onto the tool 1310. In at least one embodiment, the support shaft 1320 and rotary drive shaft assembly 1330 are axially advanced into the open center area 1402 in the universal port 1400 such that the first support arms 1322 are seated in corresponding slot formation 1416 in the outer ring 1410 and the second support arms 1334 are seated in corresponding slot formations 1426 in the inner ring 1420. The hollow stiffening tube 1340 may be inserted over the support shaft 1320 to engage the bottom surface of the outer ring 1413. Once the universal port 1400 has been installed onto the tool 1310 and the stiffening tube 1340 installed as shown, the surgeon may then insert the assembly into the rectum portion 1502 of the colon 1500 through the anus 1504 to bring the universal port 1400 into the desired location within the rectum portion 1502. See FIG. 42. Once the surgeon has determined that the universal port 1400 is located in the desired position, a rotary actuation motion is applied to the rotary drive shaft assembly 1330 which rotates the inner ring 1420 relative to the outer ring 1410 and thereby deploys the suture barbs 1430 into the adjacent colon wall to affix the universal port 1400 thereto. Thereafter, the surgeon may then withdraw the surgical tool 1310 out through the stiffening tube 1340 leaving the universal port 1400 and stiffening tube 1340 in position as shown in FIG. 42. As can be seen in FIG. 42, the end of the flexible sleeve 1412 extends around the stiffening tube 1340 and out through the patient's anus 1504. The surgeon may then insert other instruments up through the stiffening tube 1340 (if retained in place) or through the flexible sleeve 1412 (if the stiffening tube 1340 has been removed) and through the opening 1402 in the universal port 1400 to gain access to the colon portions beyond. FIGS. 43 and 44 illustrate the universal port 1400 installed in the rectum 1502 after the stiffening tube 1340 has been removed. In FIG. 43, the diseased colon portion 1508 has been cut from the distal colon portion 1520. Both the end 1510 of the diseased portion 1508 and the end 1522 of the distal colon portion 1520 have been stapled shut. Those processes may be performed using the various surgical tools, stapling heads and anvil arrangements of various embodiments of the present invention or they could have been performed using a separate endocutter (not shown) that was inserted through additional ports or openings provided through the abdominal wall.

Figure 45:
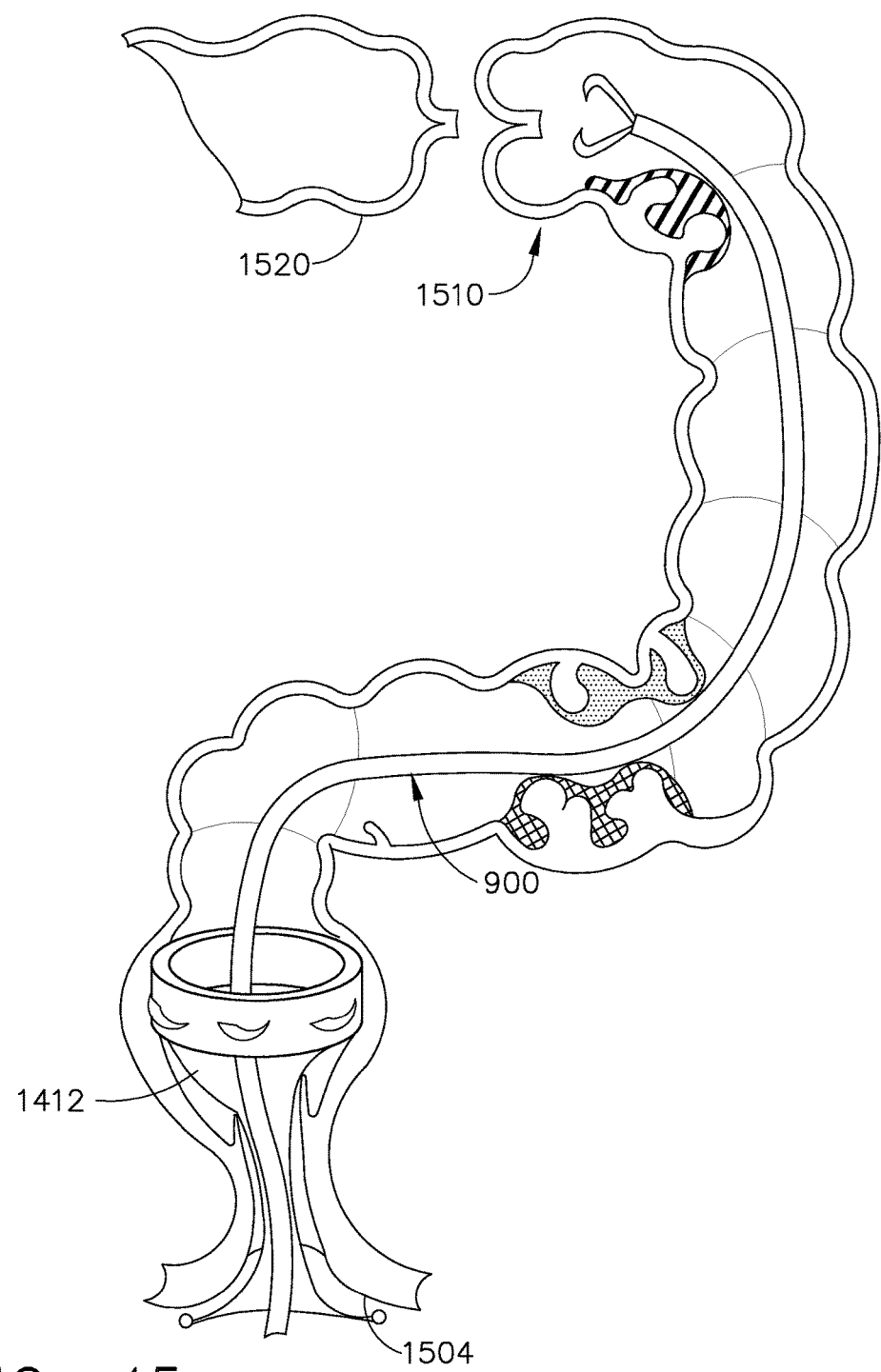
FIG. 45 is another view of the universal port and grasping instrument depicted in FIG. 44.
Figures 46, 47:
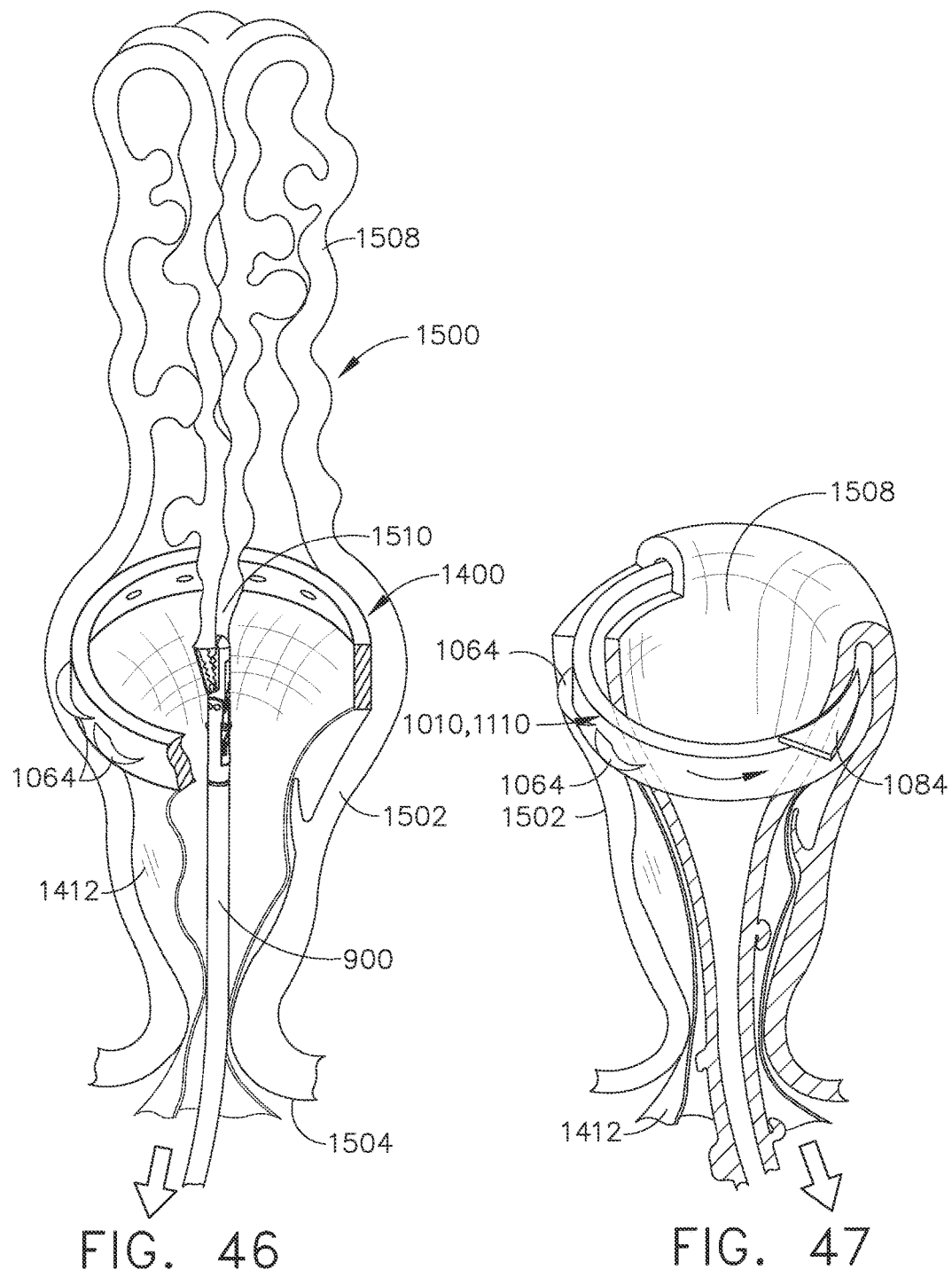
FIG. 46 is another view of the universal port of FIGS. 44 and 45 wherein the grasping instrument is being used to draw the diseased colon portion through the universal port.
FIG. 47 illustrates use of another universal port embodiment of the present invention within a colon wherein a diseased portion has been drawn therein and the tissue cutting members of the port have been deployed to sever the diseased portion from the rectum.

FIG. 44 illustrates use of a grasping instrument 900 in connection with the universal port 1400 that has been attached within the rectum 1502 of the colon 1500. In this Figure, the diseased portion 1508 of the colon 1500 has been cut from the distal portion and wax or other suitable material 1512 has been injected over some of the lesions 1511 and a web like covering material 1514 has been placed over other lesions 1513 to prevent seeding. FIG. 45 illustrates use of the grasping device to grab the end 1510 of the diseased portion 1508 to pull it back through the universal port 1400 as shown in FIG. 46. Thereafter, the diseased portion 1508 may be severed from the rectum 1502 by a conventional tissue cutting instrument that is inserted through another port or opening in the abdominal wall. FIG. 47 illustrates, in somewhat diagrammatic format, a similar arrangement wherein a universal port 1010 or 1110 has been used and the diseased portion 1508 has been pulled down therethrough. In that instance, the surgeon reattaches the surgical instrument 10 or installation tool to the universal port to activate the tissue cutting members 1084 thereof to sever the diseased portion 1508 from the rectum.

Figure 48:
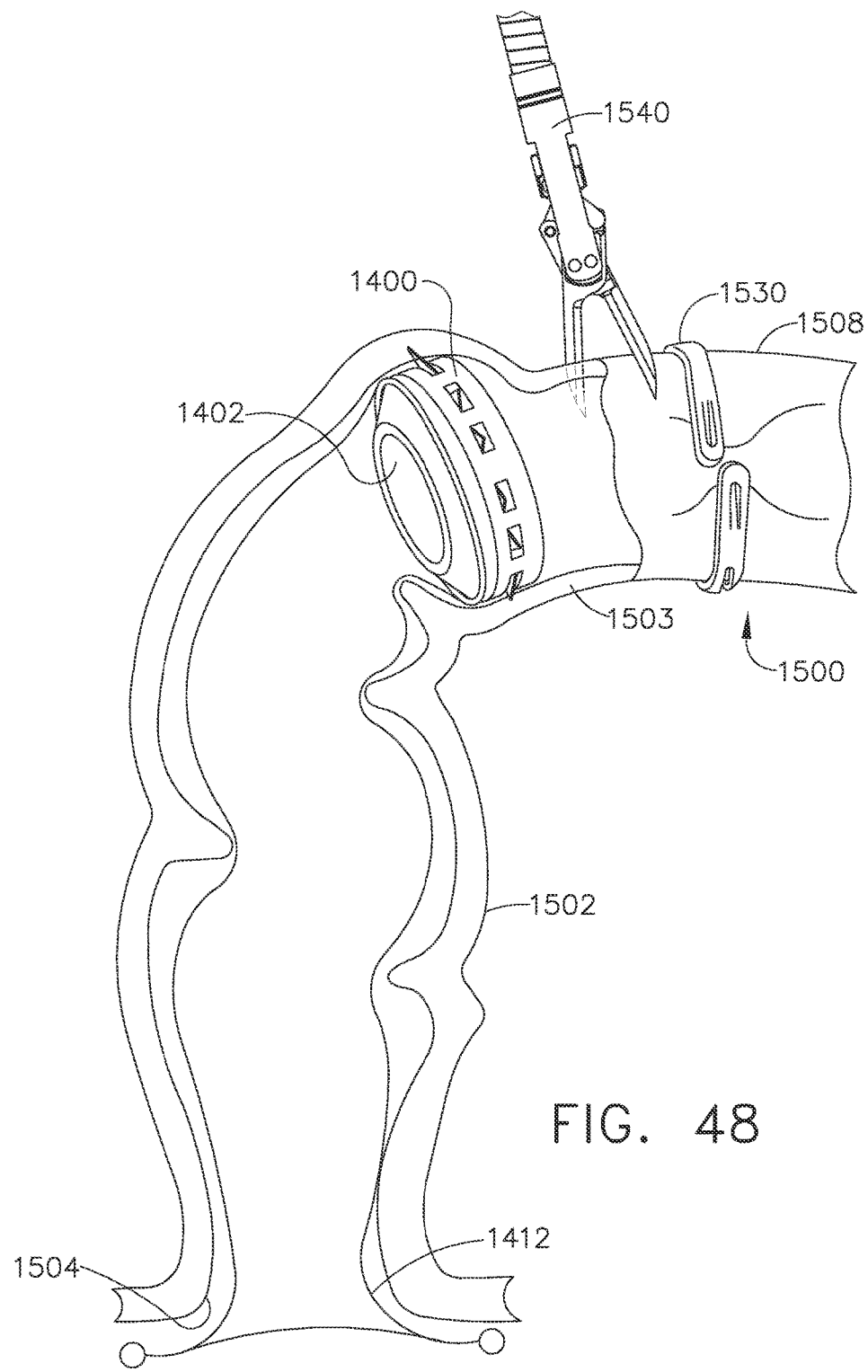
FIG. 48 is another view of a portion of a colon with a universal port embodiment of the present invention installed therein.
Figure 49:
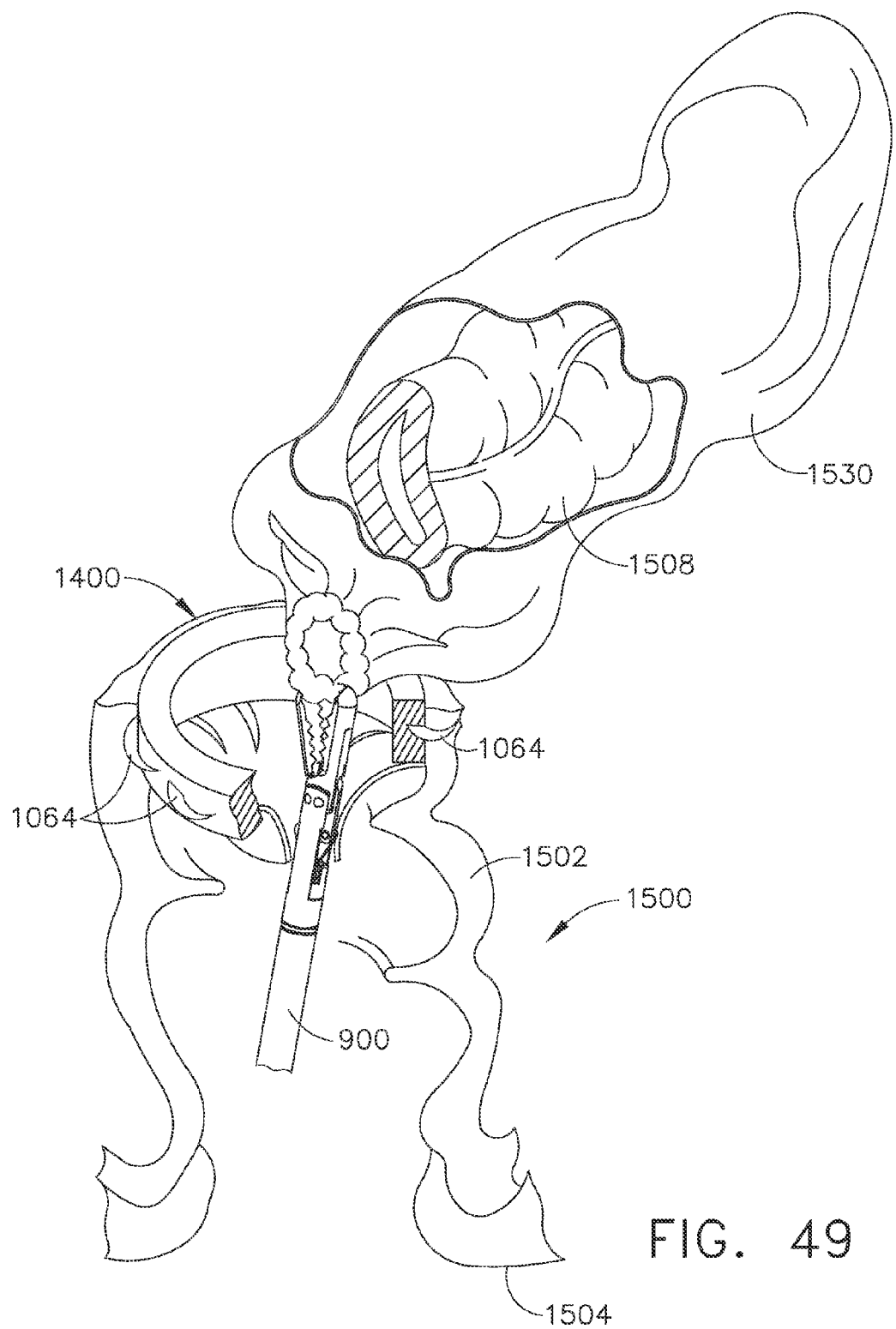
FIG. 49 is another view of the colon and universal port of FIG. 47 wherein a severed diseased portion has been inserted into a collection bag that is being drawn through the port with a grasping instrument.

In FIG. 48, a conventional metal clamp 1530 has been installed between the rectum portion 1502 and the diseased portion 1508. In the depicted embodiment, the surgeon is using a cutting instrument 1540 to cut the portion 1503 of the colon 1500 located between the universal port 1400 and the clamp 1530. Once the diseased portion 1508 has been separated from the rectum portion 1502, the surgeon may withdraw the severed diseased portion 1508 through the hole 1402 in the universal port 1400. The sleeve 1412 prevents the diseased portion 1508 from contaminating the rectum portion 1502 as it is removed through the anus 1504. Once the diseased portion 1508 of the colon 1500 has been removed, the surgical tools and tool heads disclosed herein may be inserted through the anus 1504 to re-attach the colon portion 1520 to the rectum 1502. In FIG. 49, the diseased portion 1508 has been placed into a pouch 1530 that was inserted through the universal port 1400.

Figure 50:
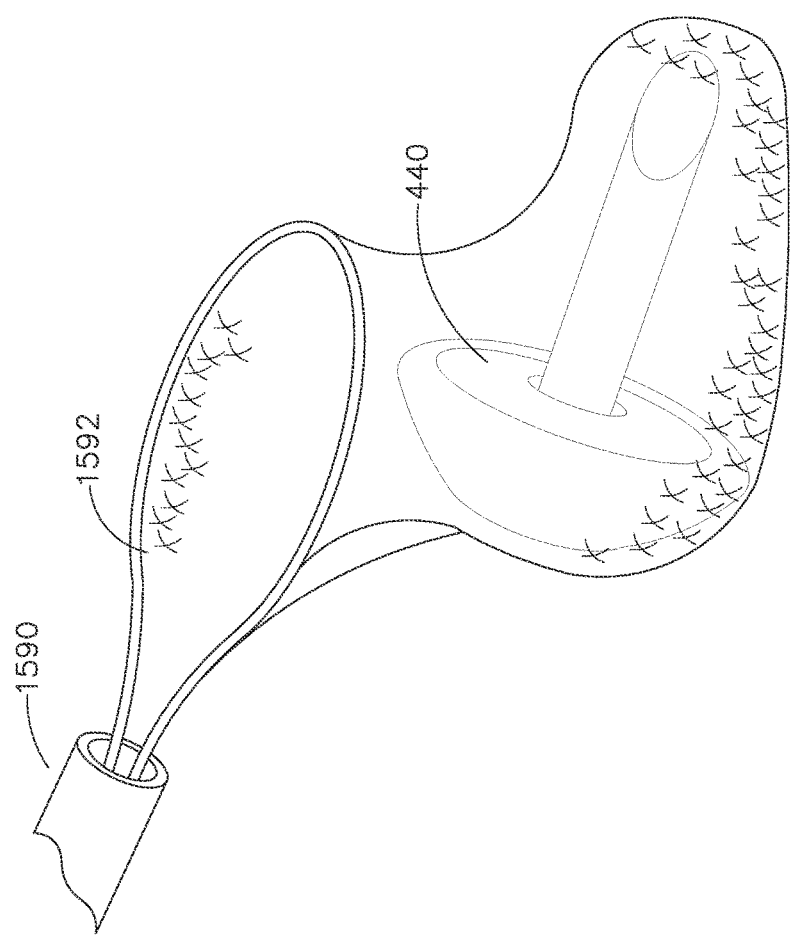
FIG. 50 is a partial perspective view of a retrieval instrument used to retrieve an anvil from the surgical site.

FIG. 50 illustrates one method of removing an anvil 440 from the surgical site after use. In this method, a retrieval instrument 1590 that has a deployable pouch portion 1592 is inserted through another opening or port provided through the abdominal wall. However, those or ordinary skill in the art will appreciate that the surgeon may introduce and remove an anvil 440 through the universal port 1400. In particular, it will be further appreciated that the various collapsible anvil arrangements disclosed in the previously incorporated patent applications are well-suited for this purpose.

Figure 51:
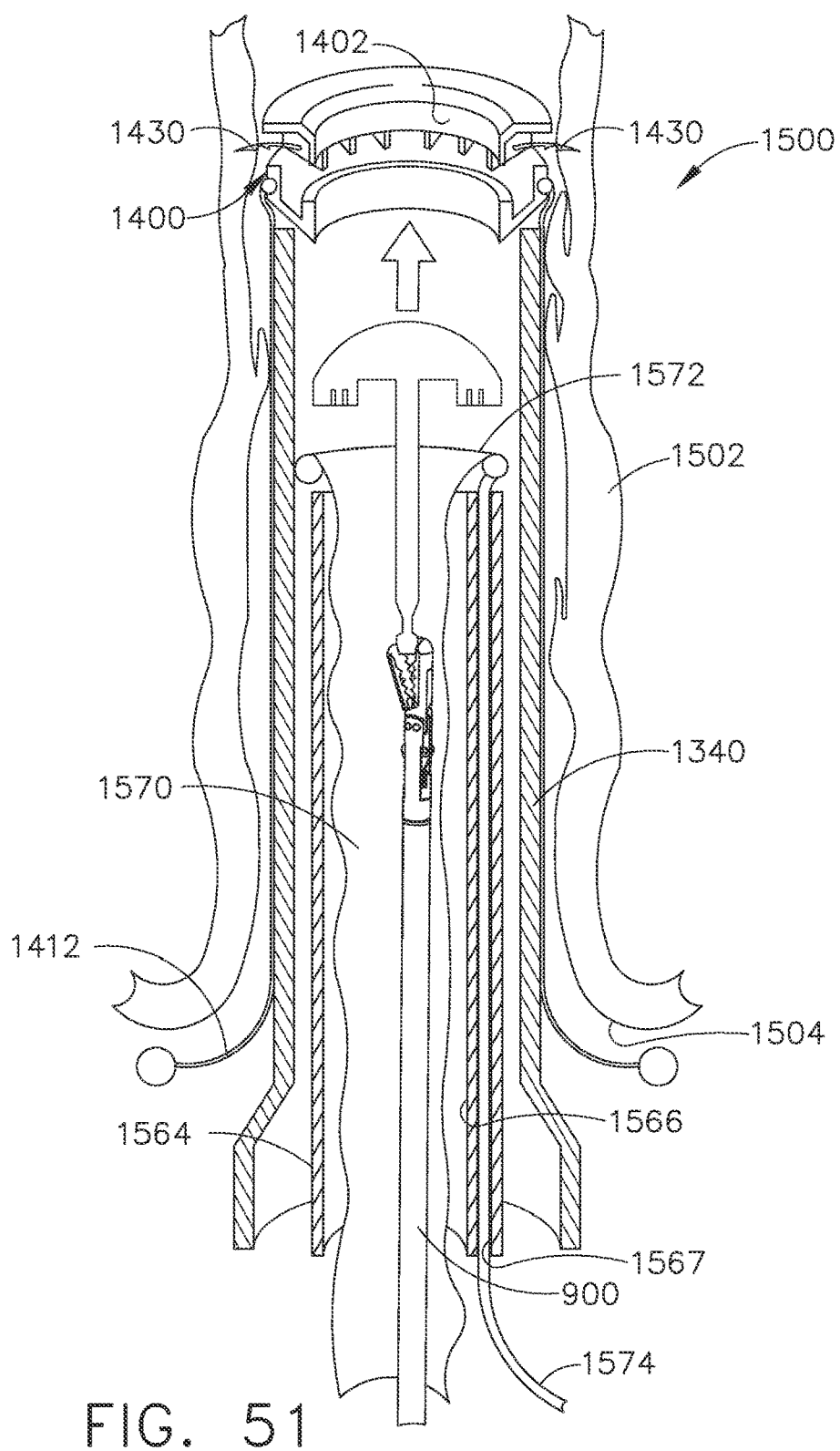
FIG. 51 is a partial cross-sectional view of a universal port embodiment of the present invention and insertion tube embodiment of the present invention positioned within the rectum with a retrieval tool embodiment of the present invention inserted therein to introduce an anvil into the surgical site.
Figure 52:
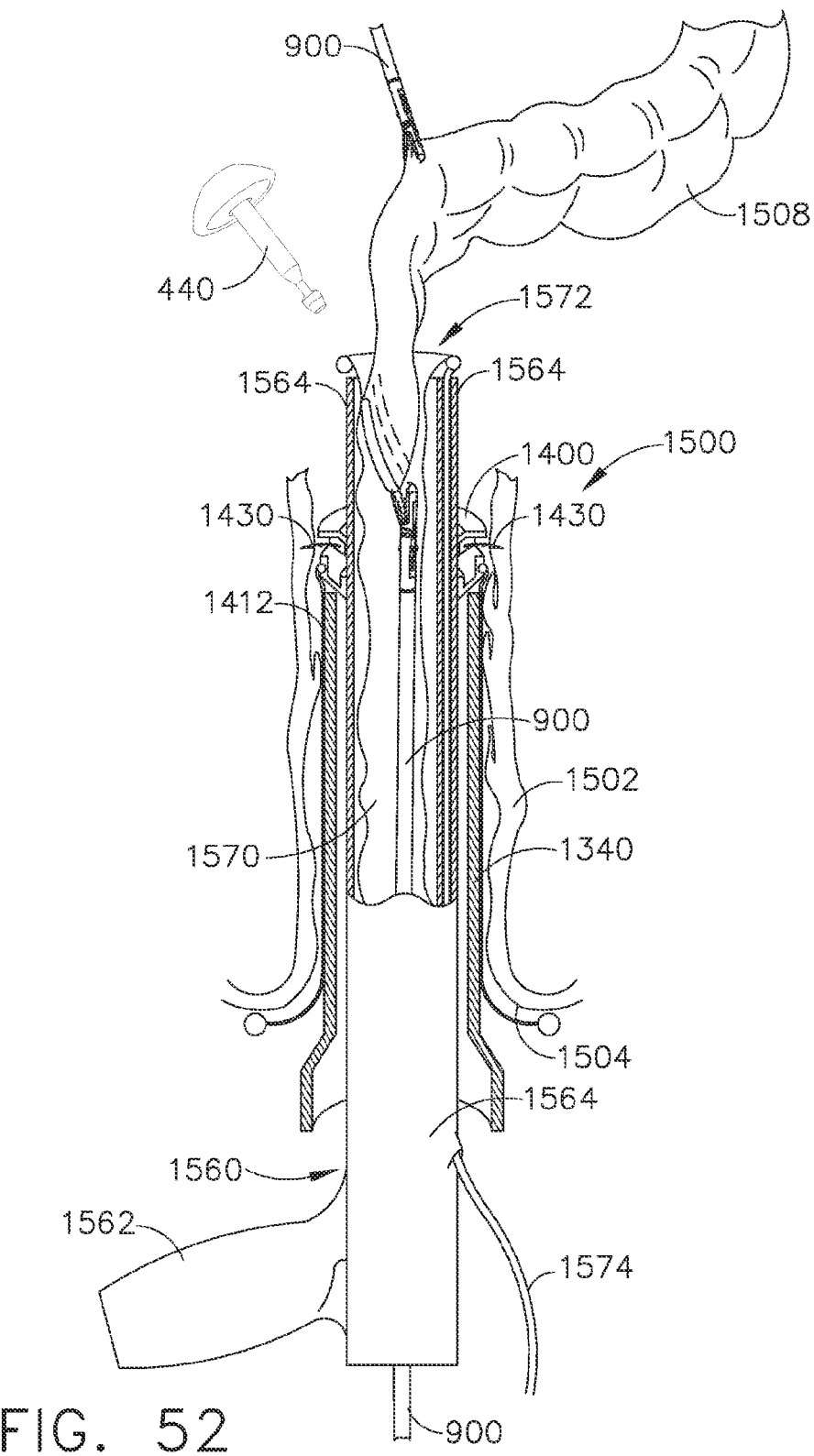
FIG. 52 is another view of the universal port, insertion tube and retrieval tool as depicted in FIG. 51 and wherein a diseased portion of the colon is being drawn into the retrieval tool by a grasping instrument inserted therethrough.

Turning to FIGS. 51 and 52, the universal port 1400 and the stiffening tube 1340 are particularly well-suited for use with a retrieval tool embodiment 1560 of the present invention. In various forms, the retrieval tool 1560 comprises a handle portion 1562 that has a hollow retrieval tube 1564 protruding therefrom that defines a conduit passage 1566 extending through the tool to facilitate the passage of tools therethrough. FIGS. 51 and 52 illustrate the passage of a grasping instrument 900 therethrough. Various embodiments further include a flexible sleeve 1570 that has a cinchable distal opening 1572 that is positioned on the distal end 1565 of the retrieval tube 1564. A cinch cord 1574 is attached to around the cinchable opening and extends through a passage 1567 in the retrieval tube 1564 as shown in FIG. 51. FIG. 51 also illustrates use of the retrieval tool 1560 and universal port 1400 for introducing an anvil 440 into the surgical site with a grasping instrument 900. FIG. 52 illustrates the withdrawal of the diseased specimen 1508 into the sleeve 1570 in the retrieval tool 1560. Once the specimen 1508 has been received within the sleeve 1570, the surgeon may cinch the opening 1572 closed by pulling on the cinch cord 1574.

Figure 53:
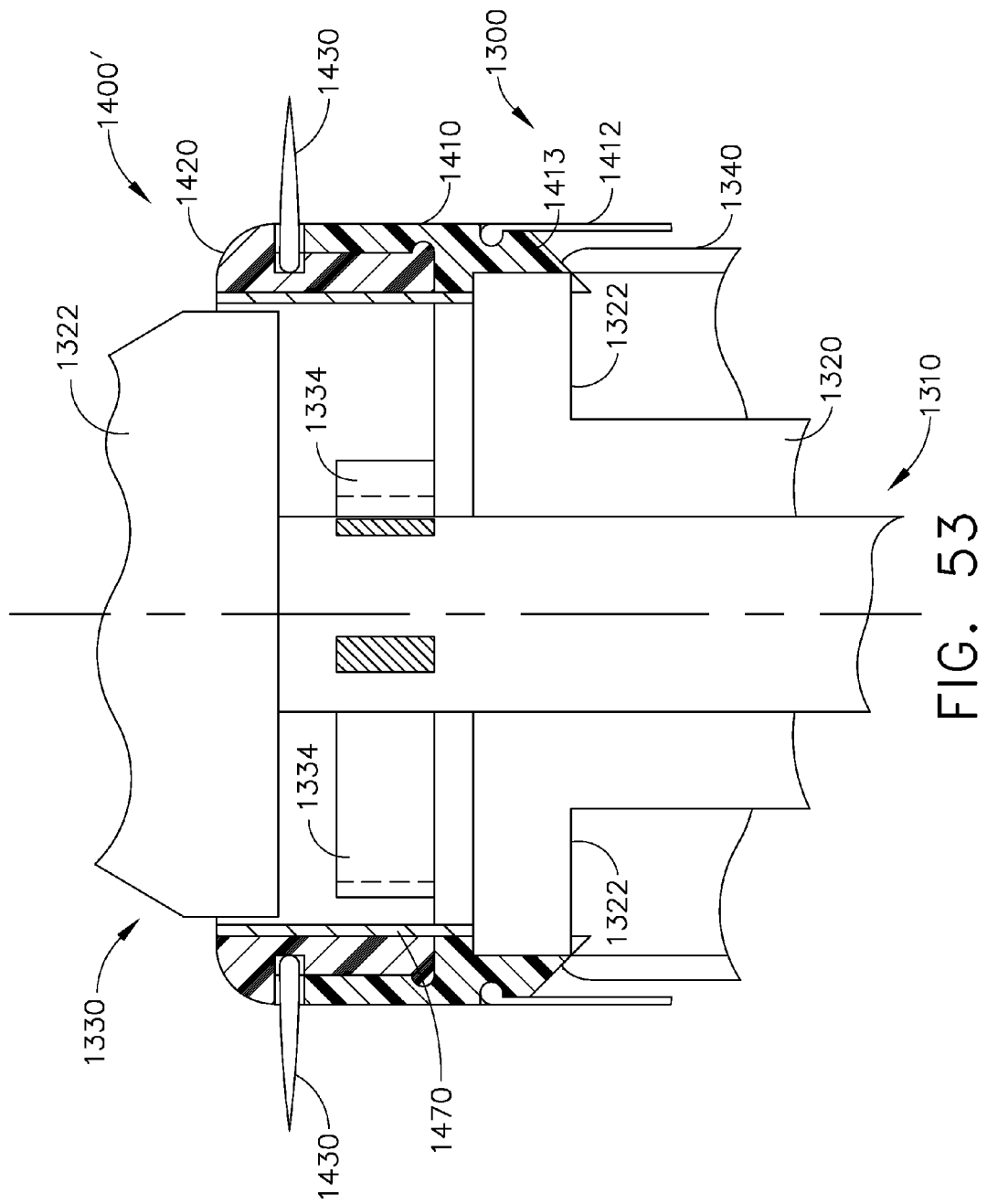
FIG. 53 is a partial cross-sectional view of another universal port embodiment of the present invention.

Referring again to FIG. 36, the outer ring portion 1410 and/or the inner ring portion 1420 of the universal port arrangement 1400 can be comprised of a rigid material. In at least one embodiment, the ring portion 1410 and/or the ring portion 1420 can be comprised of plastic, for example. FIG. 53 illustrates an alternative universal port arrangement 1400' that is substantially similar to universal port 1400, except that the inner and/or the outer ring portions 1410, 1420 are fabricated from an elastic material such as, for example, rubber. In such an embodiment, a rigid ring 1470 can be positioned within the universal port 1400' to retain the port 1400' in an expanded orientation during installation. In at least one embodiment, referring now to FIG. 41B, the rigid ring 1470 can be comprised of metal, for example, and can comprise slots 1476 which are sufficiently aligned with the slots 1426 defined in the inner ring 1420 such that the second arms 1334 of the tool 1310 can extend trough the slots 1476 into the slots 1426. In at least one such embodiment, the rigid ring 1470 can be sized and configured such that it is closely received within the inner ring portion 1420 in order to hold the ring portions 1410, 1420 in their configurations when the universal port arrangement 1400' is being positioned within the patient's rectum. Thereafter, the rigid ring 1470 can be removed from the port arrangement 1400. In at least one such embodiment, referring again to FIG. 41B, the rigid ring 1470 can comprise a slot 1479 which can be configured to be engaged by a withdrawal tool. In certain embodiments, the surgeon may insert a grasping instrument up through the patient's rectum and grasp the rigid ring 1470 once the tool 1310 has been disengaged and removed from the port arrangement 1400' and it is no longer desirable to pass objects through the universal port 1400'. In any event, once the rigid ring 1470 has been removed from the universal port 1400', the flexible rings 1410, 1420 can flex inwardly and assume a collapsed position, for example. See e.g., FIG. 26.

FIGS. 54-60 illustrate another port 1600 embodiment of the present invention. As can be most particularly seen in FIGS. 55 and 56, the port 1600 has a body portion 1602 that is fabricated from a plurality of flexible slat member 1604. Each slat member 1604 has a distal end 1606 that is journaled on a distal ring 1620. Likewise, each slat member 1604 has a proximal end 1608 that is journaled on a proximal ring 1622. The proximal end portions 1608 are configured to releasably engage a distal end 1662 of a stiffening tube 1660. In particular, in at least one embodiment, a collection of bayonet-type slots 1664 are formed around the outer circumference of the distal end 1662 of the stiffening tube 1660. Such bayonet-type arrangement facilitates releasable attachment of the port 1600 by aligning the proximal end portions 1608 of the slat members 1604 with the slots 1664 and inserting the end portions 1608 and twisting to seat them in the slots 1664. FIG. 55 illustrates the port 1600 in its collapsed state. When in that state, the port 1600 has an outer diameter "OD" and when in an expanded state (FIG. 56), the port 1600 has an overall outer diameter "OD1". The ends of the member have an outer diameter of OD2. In one embodiment, for example, OD may be approximately 20 mm, OD1 may be approximately 65 mm and OD2 may be approximately 40 mm. However, other sizes may be employed.

Figure 54:
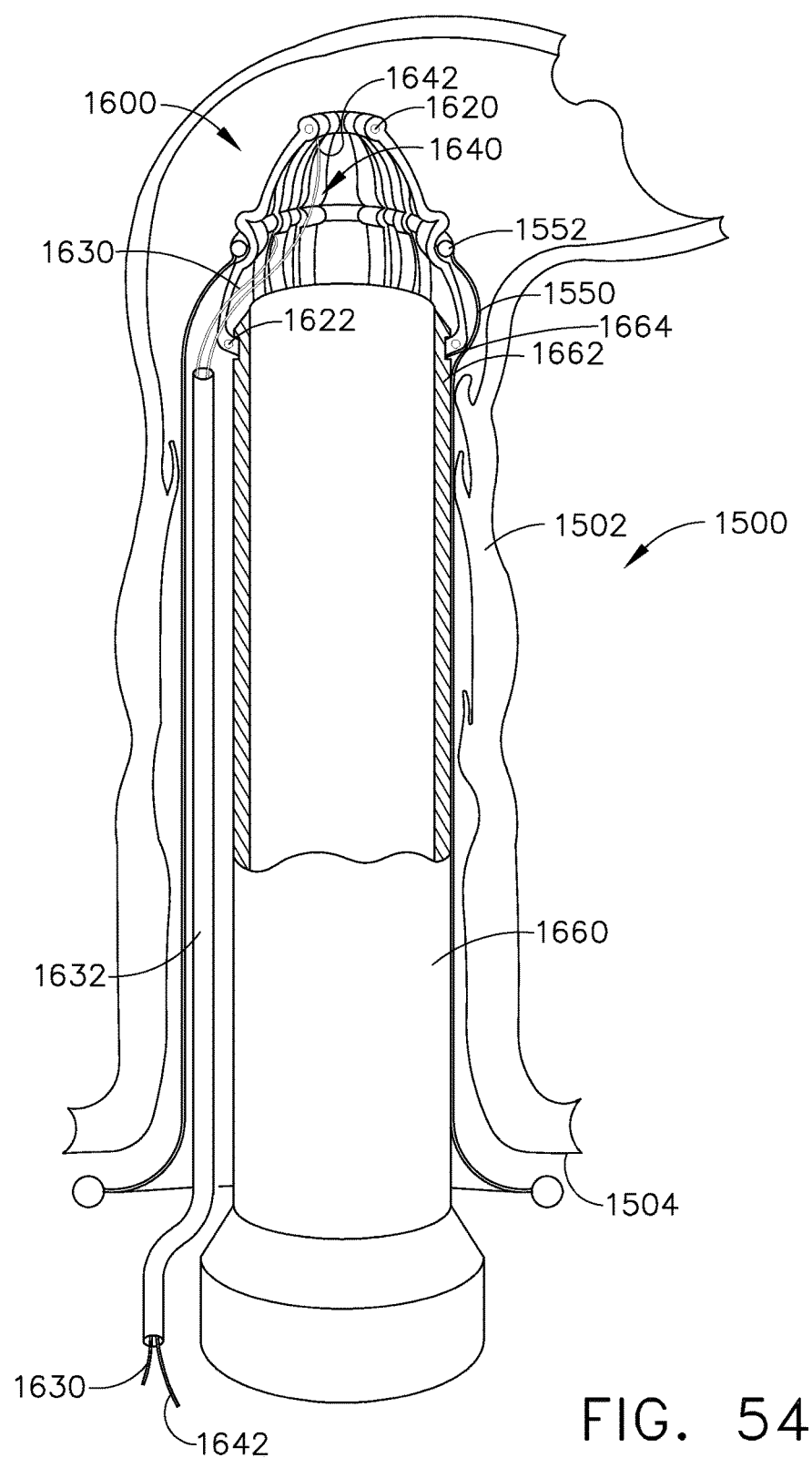
FIG. 54 is a partial cross-sectional view of another port embodiment of the present invention and insertion tube embodiment of the present invention positioned within the rectum.

As can be seen in FIGS. 55 and 56, each slat 1604 has a central portion 1610 that has a slight radius area formed therein and which has a barb deployment hole 1612 therethrough. A barbed surgical suture 1630 extends through each barb deployment hole 1612. The sutures 1630 extend through an actuator conduit 1632 as shown in FIG. 54. An actuator 1640, in the form of a tension cable 1642, is attached to the distal ring 1620. Also various embodiments employ a flexible sleeve 1650 that extends around the port body 1602 and is retained in position by an elastic band or ring 1552.

FIG. 54 illustrates use of the port 1600 and the hollow stiffening tube 1660. After the port 1600 has been attached to the distal end of the stiffening tube 1660, the sleeve 1550 is deployed to extend over the stiffening tube 1660 and the actuation conduit 1632. The entire device may then be inserted through the anus 1504 into the rectum portion 1502 of the colon 1500 and oriented in a desired position. As can be seen in FIG. 54, the sleeve 1550 also protrudes out through the anus 1504. Once the surgeon has located the port 1600 in the desired position, an actuation motion in the form of tension "T" is applied to the cable 1642 to expand the member 1600. As the port 1600 expands, the relatively stiff suture barbs 1630 protrude through the holes 1612 in the slats 1604 to engage the colon wall and thereby retain the port 1600 in position.

Figure 59:
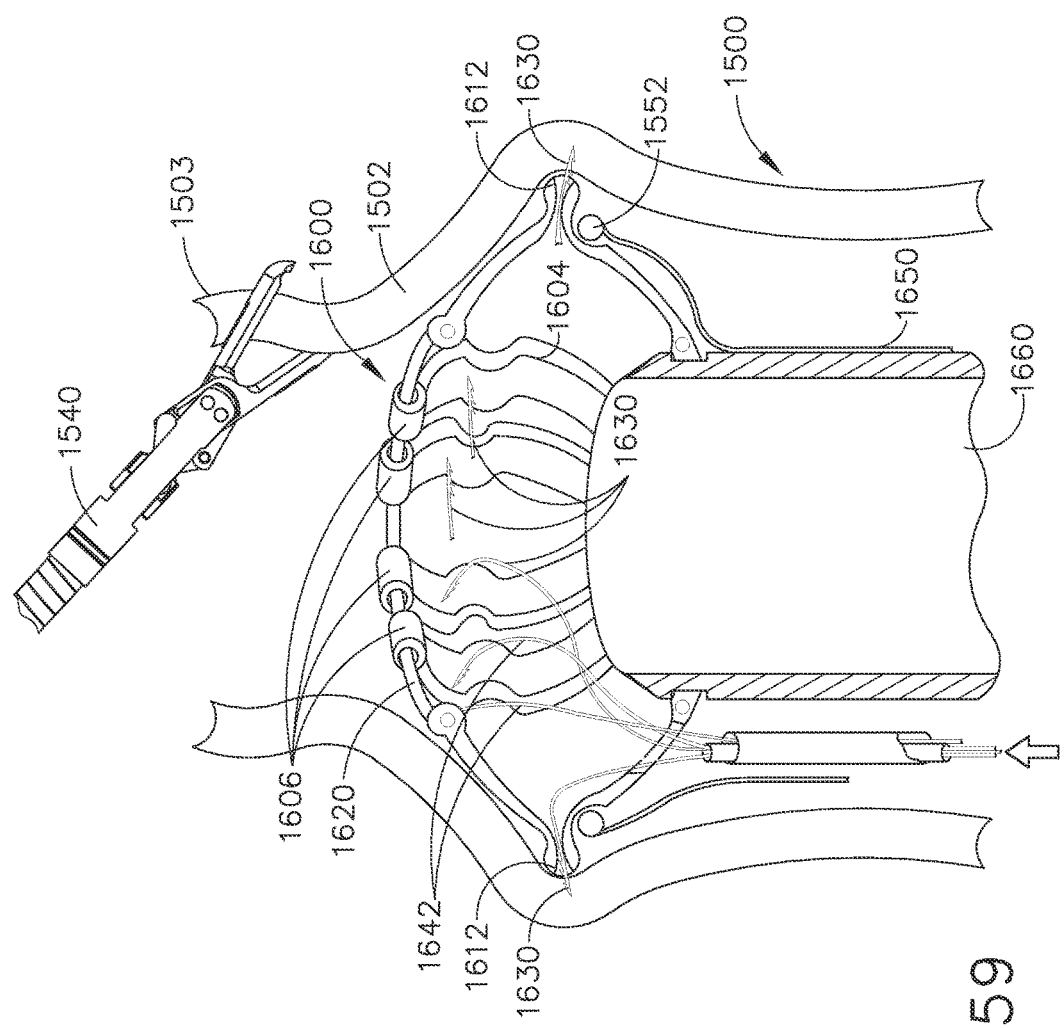
FIG. 59 is another partial cross-sectional view of the port and insertion tube of FIG. 57 deployed in a portion of the rectum and wherein a tissue cutting instrument is cutting a diseased portion of the colon from the rectum.
Figure 60:
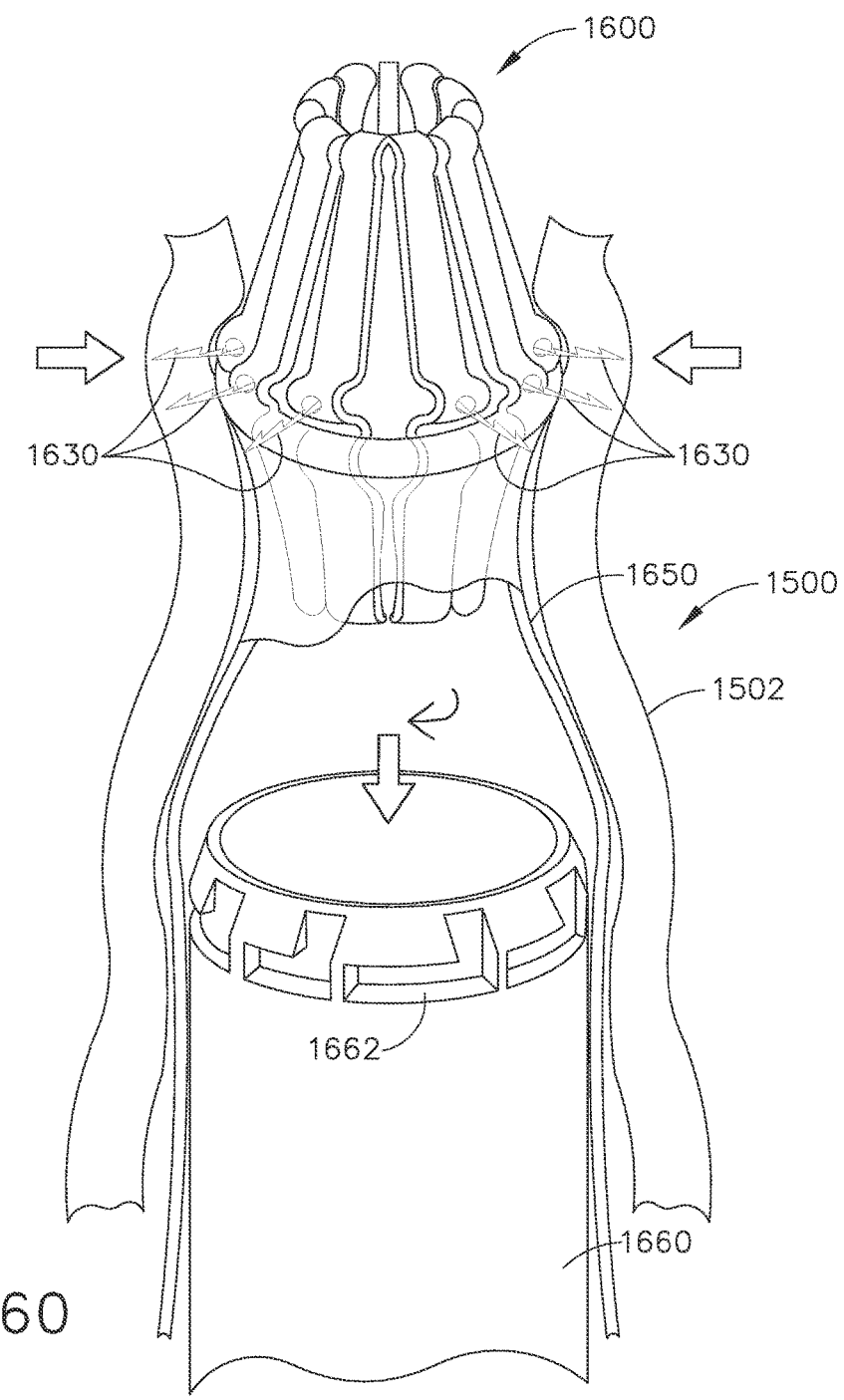
FIG. 60 is another view of the port and insertion tube of FIGS. 54-59 wherein the insertion tube has been detached from the port.

FIG. 59 illustrates use of a tissue cutting instrument 1540 to cut through the colon portion 1503 that extends between a metal clamp (not shown) and the port 1600. The surgeon may then sever the diseased portion in the various manners described above and remove them through the expanded port 1600 and out through the stiffening tube 1660. Thereafter, the surgeon may detach the stiffening tube 1660 from the port 1600 by applying a twisting motion to disengage the bayonet-type connection to enable the stiffening tube to be separated therefrom and pulled out of the anus leaving the sleeve 1650 attached to the port 1600. As can be seen in FIG. 60 the port 1600 is permitted to collapse to enable the rectum 1502 to return down to smaller diameter.

Figure 61:
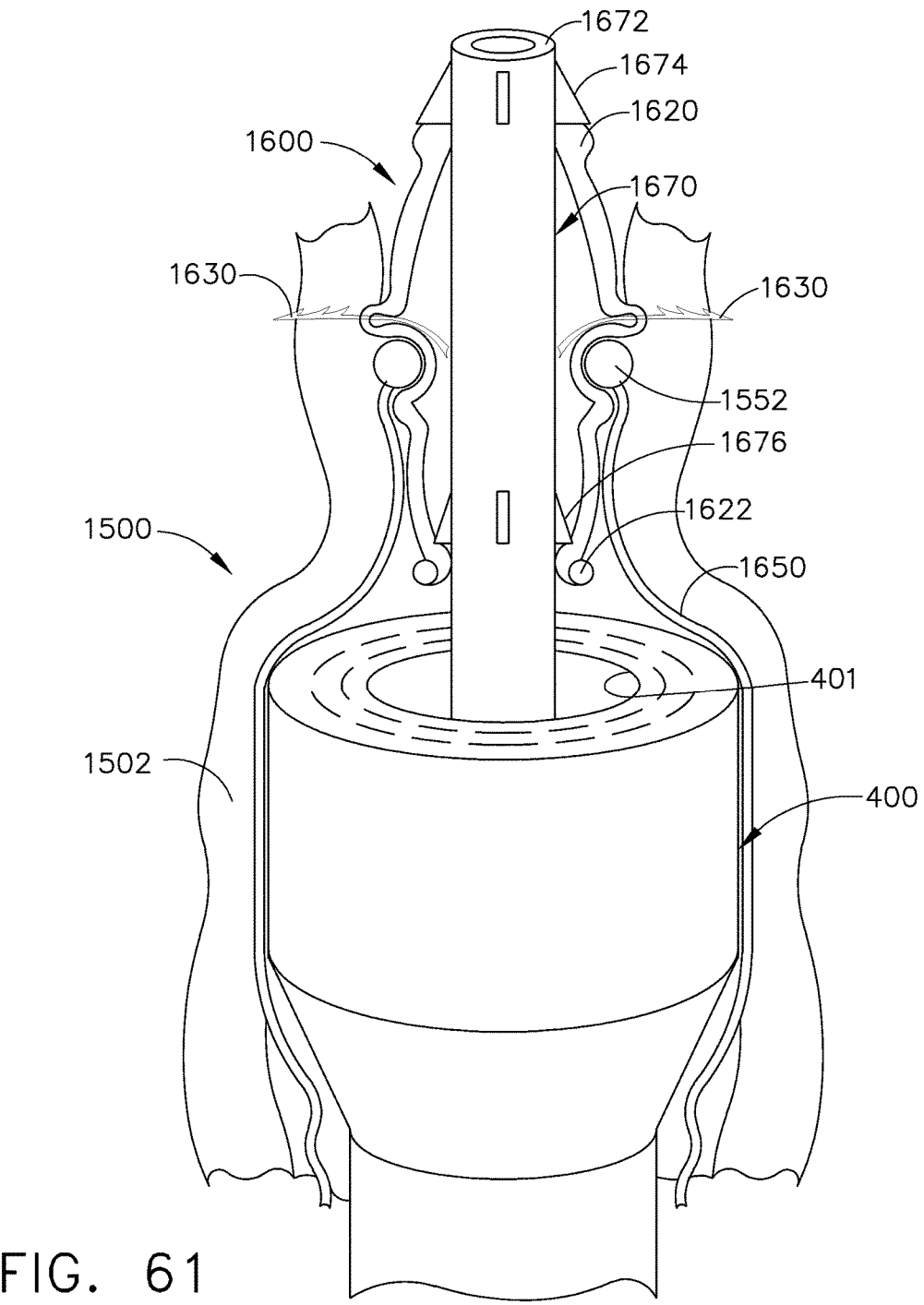
FIG. 61 is another view of the port of FIGS. 54-59 being draw into a circular stapling head embodiment of the present invention.

FIG. 61 illustrates one method of removing the port 1600 using the surgical tool 10 or other surgical circular stapler arrangement. In the depicted embodiment, a retraction adapter shaft 1670 is attached to the distal end 180 of the rotary drive shaft 150 using the various methods described above. The retraction adapter shaft 1670 has a plurality of distal retraction wedges 1674 radially extending from its distal end 1672. In addition, a plurality of proximal retraction wedges 1676 radially extend therefrom as shown in FIG. 61. Once the retraction adapter shaft 1670 has been attached as shown, the surgeon may insert the instrument into the rectum 1502 to the position shown in FIG. 61. As can be seen in that Figure, the distal retraction wedges 1674 are in retracting engagement with the distal ring 1620 and the proximal retraction wedges 1676 engage the proximal ring 1622. The surgeon may then use the slider switch 230 on the handle assembly 20 (FIG. 1) and, if necessary the control knob 248 to axially pull the rotary drive shaft 150 and the retraction adapter shaft 1670 proximally. Prior to pulling the adapter shaft 1670 proximally, the surgeon may attach an anvil onto the retraction adapter shaft 1670, such that the anvil gets pulled into position as the retraction adapter shaft 1670 pulls the port 1600 and attached colon tissue into the central area 401 in the stapling head 400 for example. Those or ordinary skill in the art will appreciate that such arrangement serves to draw the colon tissue into position for cutting and stapling. Thereafter, the stapling head 410 may be actuated as before.

Figure 63:
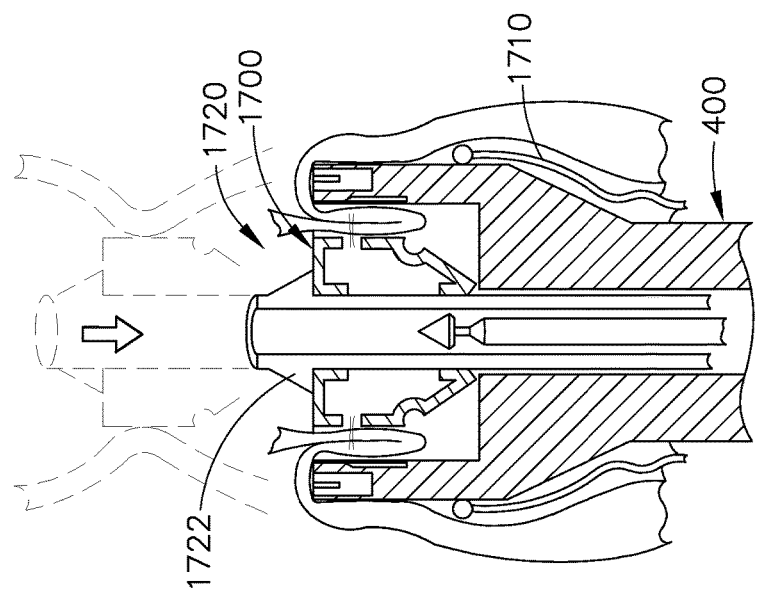
FIG. 63 a partial cross-sectional view of the circular stapling head and universal port of FIG. 62 wherein the universal port has been drawn into the circular stapling head.
Figure 62:
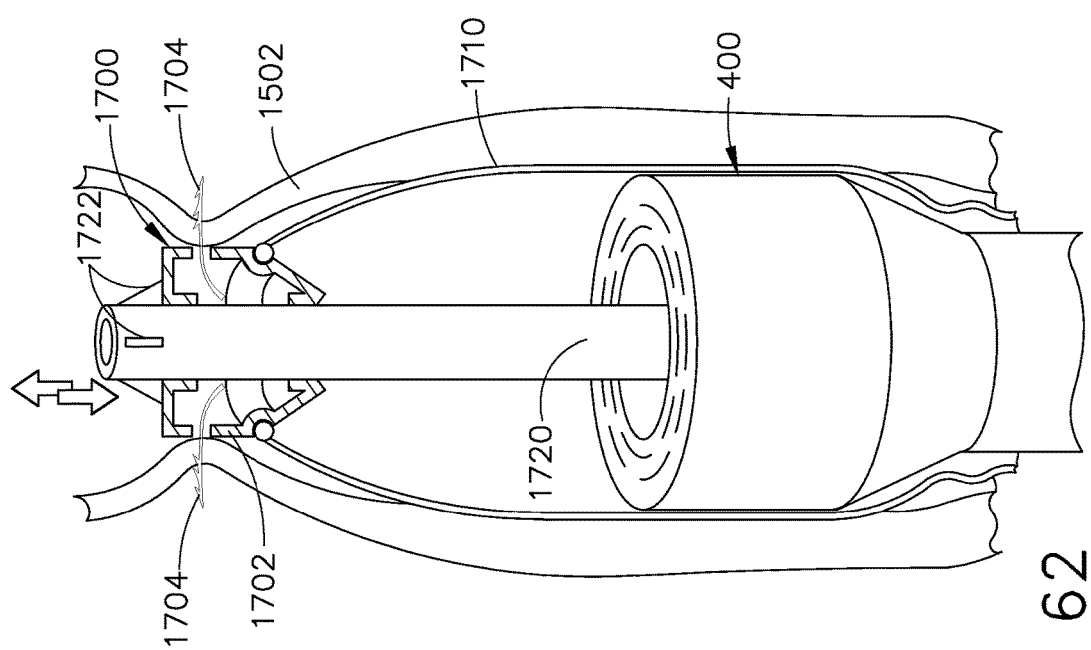
FIG. 62 is a partial perspective view of another universal port embodiment of the present invention installed within the colon and being engaged by a circular stapling head embodiment of the present invention.

FIGS. 62 and 63 illustrate an alternate port 1700 that has a body portion 1702 with a plurality of suture barbs 1704 protruding therefrom that has been attached to the rectum 1502 as shown. The port 1700 also has a flexible sleeve 1710 attached thereto. This embodiment also employs a retraction adapter shaft 1720 that has distal retraction wedges 1722 thereon. The surgical instrument 10 is otherwise used as described above to draw the port 1700 into the stapling head 400 as shown. As the port 1700 is drawn into the stapling head 400, the surgeon pulls on the sleeve 1710 such that it disengages from the port 1700 and assumes a position around the stapling head 400. See FIG. 63.

Figure 64:
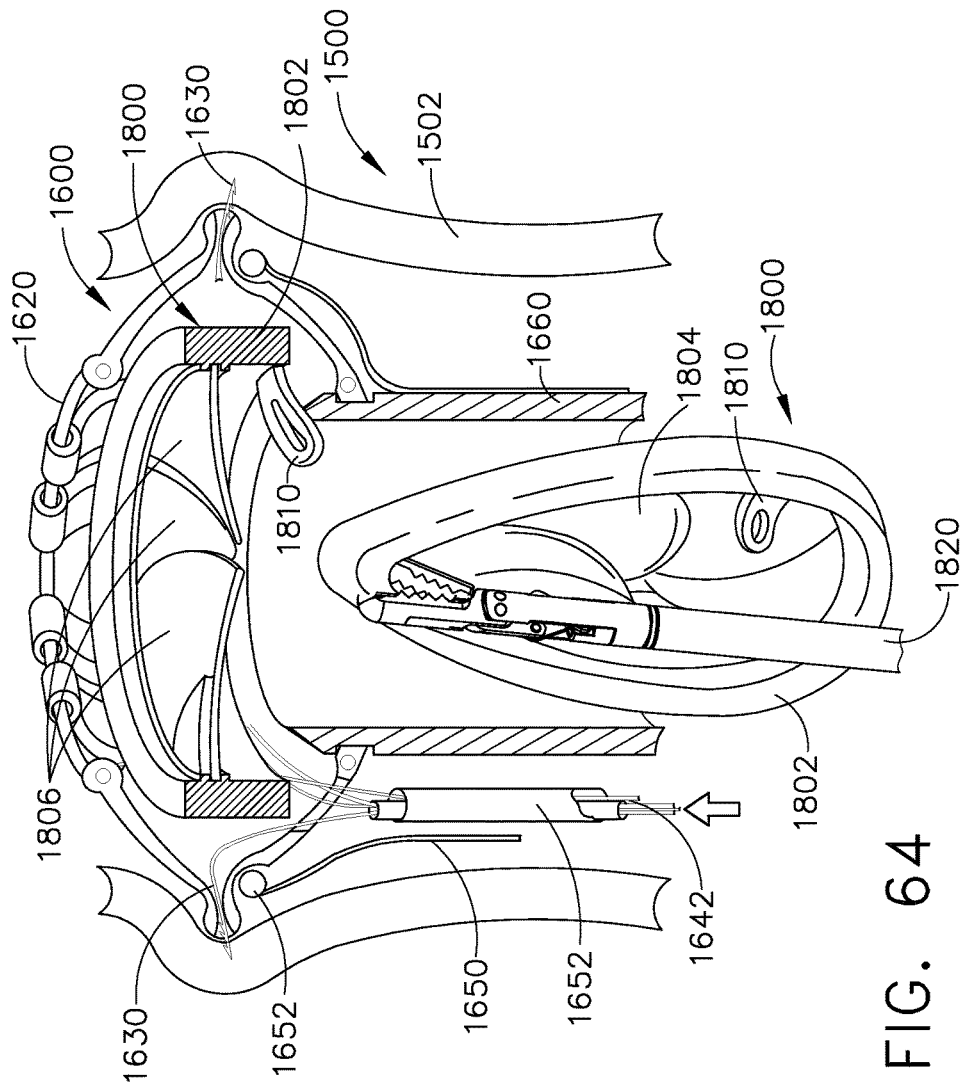
FIG. 64 is another perspective view of a port and insertion tube embodiment of the present invention installed with the colon and wherein a grasping instrument is used to introduce and insert a flexible port member embodiment therein.

FIG. 64 illustrates use of a flexible port member 1800 in connection with a port 1600. As can be see in that Figure, the port member 1800 has a flexible outer ring 1802 that has a plurality of overlapping spirally arranged flaps or petal-like members 1806 that serve to close the central area 1804 defined by the ring 1802, yet permit the passage of objects therethrough. To install the port member 1800 into the port 1600, the surgeon may employ a grasping instrument 1820 to insert the port member 1800 into the stiffener shaft 1660 and into the central area of the expanded port 1600. The port member 1800 may also include a retrieval tab 1810 to enable the surgeon to remove the port member 1800 with the grasping instrument 1820.

One of the challenges facing surgeons when performing colorectal surgery is the difficulty in making the transection in tight and angulated spaces. Limited visualization, as well as the magnitudes of the forces that may generally be required to transect and seal the colon, add to those challenges. Rather than use a mechanical structure to dilate the head of a modular circular stapler, the tissue manipulation device 1900 of the present invention uses a vacuum to draw the colon down to the shaft diameter. With the colon tissue bound to the vacuum shaft, the manipulation of the shaft can then facilitate relative easy movement of the colon for dissection.

Figures 65, 66:
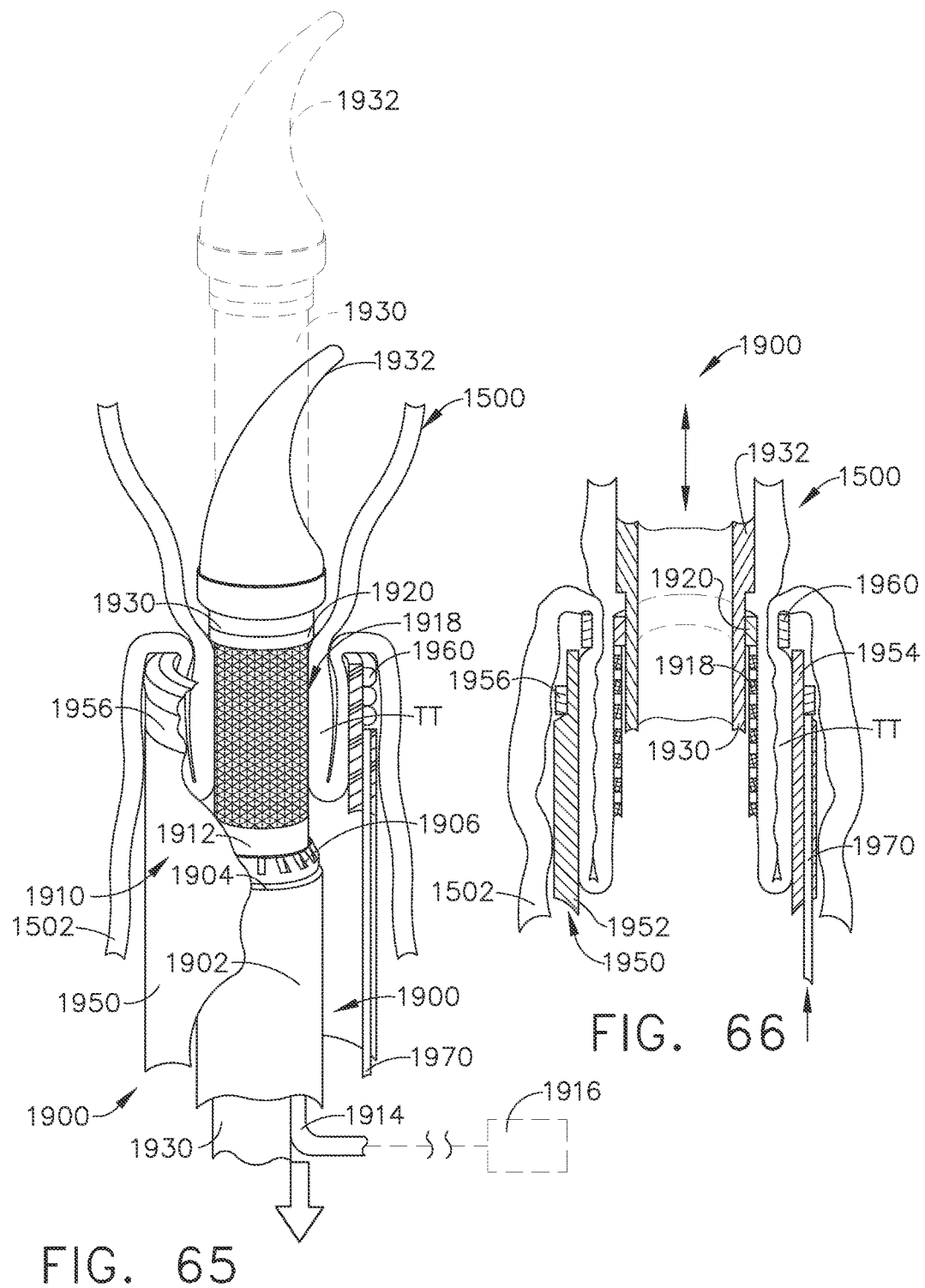
FIG. 65 is a partial cross-sectional perspective view of a tissue manipulation device embodiment of the present invention inserted into the colon and engaging a portion thereof.
FIG. 66 is a cross-sectional view of a portion of the tissue manipulation device and colon of FIG. 65.

As can be seen in FIGS. 65 and 66, the tissue manipulation device 1900, according to at least one embodiment includes a hollow outer shaft 1902 that rotatably supports a vacuum shaft 1910 thereon. The hollow outer shaft 1902 is substantially rigid and is designed to be inserted into the rigid shaft portion 1952 of a ring installation instrument 1950 as will be discussed in further detail below. The vacuum shaft 1910 comprises a proximal attachment collar 1912 that is rotatably affixed to the distal end 1904 of the outer shaft 1902. A seal 1906 is provided between the distal end 1904 of the outer shaft 1902 and the proximal attachment collar 1912. The collar 1912 interfaces with a vacuum supply tube 1914 that is attached to a source of vacuum 1916.

In various embodiments, the vacuum shaft 1910 has a screen section 1918 therein that is attached to the attachment collar 1912. The screen mesh may comprise stainless steel, titanium, etc. mesh. In at least one embodiment, the screen mesh may be constructed of two layers of screen at a 45 degree rotation to one another in an effort minimize any likelihood of clogging with tissue. The distal end of the screen section 1918 is attached to a seal ring 1920 that is configured to establish a sliding and rotating seal with a central drive shaft member 1930. As shown in FIGS. 65 and 66, flexible head member 1932 is attached to the distal end 1931 of the drive shaft 1930. The flexible head 1932 may be fabricated from rubber or other flexible material and have a slight bias as shown. Such arrangement enables the surgeon to better manipulate portions of the colon during installation and positioning of the instrument 1900. However, other head configurations could be use. The drive shaft 1930 extends through the outer shaft 1902 and interfaces with a handle or other arrangement that enables the surgeon to apply rotary and axial motions thereto.

As indicated above, the tissue manipulation device 1900 may be used in connection with a ring installation instrument 1950. As can be seen in FIGS. 65 and 66, the ring installation instrument 1950 includes a shaft 1952 that has a distal end 1954 that is configured to slidably support an elastic anastomosis ring 1960 thereon. The distal end 1954 of the shaft 1952 further includes a ring deployment member 1956 that is attached to a push rod 1970 that extends through the wall of shaft 1952.

The tissue manipulation device 1900 may be used as follows. The surgeon first inserts the ring installation instrument 1950 into the rectum through the patient's anus. Thereafter the tissue manipulation instrument 1900 is inserted through the shaft 1952 and into the colon. The surgeon may then apply an axial motion to the drive shaft 1930 to push a portion of the drive shaft 1930 out of the screened section 1918 to manipulate the colon into a desirable position. The vacuum shaft 1910 is also advanced distally out of the shaft 1952 to enable the target tissue "TT" to be retrieved. Once the screen section 1918 is positioned adjacent to the target tissue "TT", the surgeon may then apply the vacuum thereto to draw the target tissue "TT" onto the screen section 1918. Thereafter the vacuum shaft 1910 is drawn back into the outer shaft 1902 and the shaft 1952 of the ring installation instrument 1950. Such action causes the target tissue "TT" to fold over between the screen section 1918 and the inner wall of the shaft 1952 as shown. Once the target tissue "TT" is positioned between the screen section 1918 the shaft 1952, the surgeon may then apply a pushing motion to the push rod 1970 to axially advance the ring deployment member in the distal direction to push the anastomosis ring 1960 off of the distal end of the shaft 1952 as shown in FIG. 66.

Figure 67:
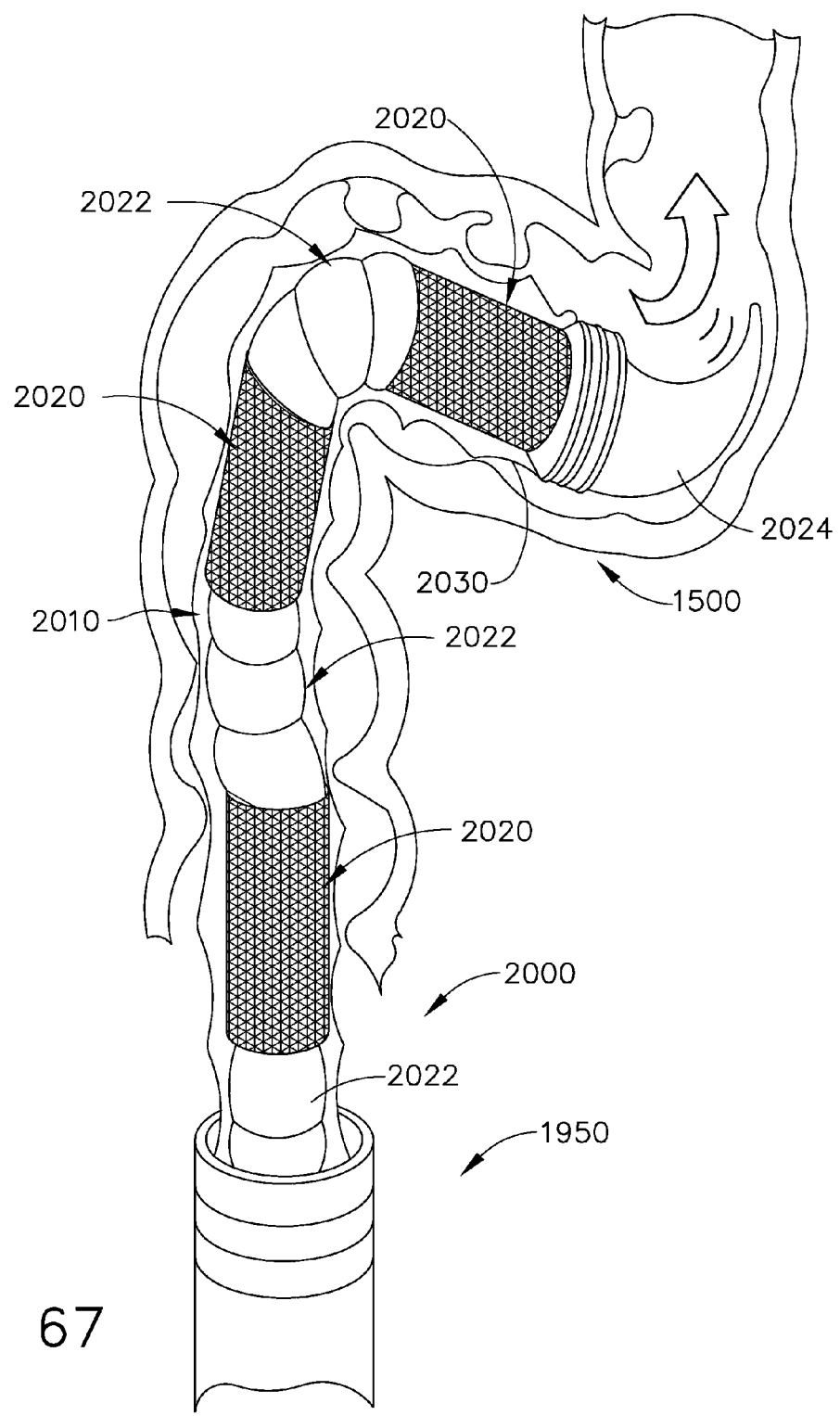
FIG. 67 is a partial perspective view of another tissue manipulation device embodiment of the present invention inserted into the colon.

FIG. 67 illustrates another vacuum shaft embodiment 2000 of the present invention. In at least one form, the vacuum shaft 2000 has a central shaft portion 2010 that has three screen sections 2020 that are interconnected by flexible joints 2022. The distal end of the shaft portion 2010 has a flexible head portion 2024. An outer sleeve 2030 may be employed to facilitate ease of insertion and when the shaft 2000 has been properly located the user may withdraw the sleeve 2030 from the device exposing the screen sections 2020. The screen sections communicate with a source of vacuum as was described above to enable the portions of the colon 1500 to be drawn into engagement therewith to facilitate better manipulation of the colon 1500.

FIG. 68 illustrates a vacuum shaft embodiment 2000' that employs spirally arranged screen sections 2020' that communicate with a source of vacuum. As the tissue is drawn into contact with the screen sections 2020' the air in the colon is permitted to exit out the vacuum shaft 2000'.

The various embodiments of the present invention represent a vast improvement over prior surgical methods and devices used to perform colorectal surgery. While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical instrument, comprising:
   an actuation system;
   a drive system coupled to the actuation system, wherein the drive system comprises:
      a rotatable shaft which defines a longitudinal axis; and
      an outer casing surrounding the rotatable shaft; and
   a tool head coupled to the drive system, wherein the tool head comprises:
      an annular cartridge comprising a plurality of staples; and
      a pliable bunchable ring surrounding the annular cartridge, wherein the surgical instrument is configured to drive the staples through the pliable bunchable ring in a direction which is transverse to the longitudinal axis, and wherein the outer casing is configured to deform the staples driven through the pliable bunchable ring.

2. The surgical instrument of claim 1, wherein the actuation system comprises a movable gear plate which defines a rack.

3. The surgical instrument of claim 2, wherein the drive system further comprises a pinion gear coupled to the rotatable shaft, wherein the pinion gear is configured to meshingly engage with the rack.

4. The surgical instrument of claim 2, wherein the actuation system further comprises an actuator coupled to the movable gear plate.

5. The surgical instrument of claim 4, wherein the actuator is a trigger.

6. The surgical instrument of claim 1, wherein the pliable bunchable ring comprises an elastomeric material.

7. The surgical instrument of claim 1, wherein the tool head further comprises a rotatable drive assembly coupled to the rotatable shaft, wherein the rotatable drive assembly is configured to drive the staples through the pliable bunchable ring substantially transverse to the longitudinal axis as the rotatable shaft is rotated.

8. The surgical instrument of claim 7, wherein the rotatable drive assembly is non-rotatably coupled to the rotatable shaft.

9. The surgical instrument of claim 7, wherein the rotatable drive assembly comprises a staple drive member configured to drive the staples from the annular cartridge as the rotatable shaft is rotated.

10. A surgical instrument, comprising:
    a pliable bunchable ring; and
    a stapler head surrounded by the pliable bunchable ring, wherein the stapler head comprises:
       a plurality of radial openings;
       a plurality of staples; and
       an actuatable drive assembly configured to drive the staples through the openings and through the pliable bunchable ring as the actuatable drive assembly is actuated, wherein the actuatable drive assembly comprises a rotatable driver configured to rotate within the stapler head.

11. The surgical instrument of claim 10, wherein the pliable bunchable ring is comprised of an elastomeric material.

12. The surgical instrument of claim 10, wherein the pliable bunchable ring is removably stored around the stapler head in a stretched condition.

13. The surgical instrument of claim 10, wherein the pliable bunchable ring is aligned with the radial openings.

14. An end effector of a surgical instrument for fastening a lumen, the end effector comprising:
    an annular cartridge body;
    an annular row of fasteners removably stored in the annular cartridge body;
    an actuatable drive assembly comprising a rotatable driver configured to rotate within the end effector; and
    a cinching member extending around the annular cartridge body, wherein the fasteners implant the cinching member to the lumen when the fasteners are ejected from the annular cartridge body.

15. The end effector of claim 14, further comprising an anvil configured to deform the fasteners.

16. The end effector of claim 14, wherein the cinching member is aligned with the annular row of fasteners.

17. The end effector of claim 14, wherein the cinching member is removably stored around the annular cartridge body in a stretched state.

18. The end effector of claim 17, wherein the cinching member is comprised of an elastomeric material.

* * * * *